United States Patent
Pflueger et al.

(10) Patent No.: US 9,387,116 B2
(45) Date of Patent: *Jul. 12, 2016

(54) APPARATUS AND METHODS FOR TREATING SLEEP APNEA

(71) Applicant: Quiescence Medical, Inc., San Juan Capistrano, CA (US)

(72) Inventors: D. Russell Pflueger, San Juan Capistrano, CA (US); Christopher Paul Thompson, Austin, TX (US)

(73) Assignee: QUIESCENCE MEDICAL, INC., San Juan Capistrano, CA (US)

( * ) Notice: Subject to any disclaimer, the term of this patent is extended or adjusted under 35 U.S.C. 154(b) by 613 days.

This patent is subject to a terminal disclaimer.

(21) Appl. No.: 13/629,237

(22) Filed: Sep. 27, 2012

(65) Prior Publication Data

US 2013/0112209 A1    May 9, 2013

Related U.S. Application Data

(63) Continuation-in-part of application No. 13/324,764, filed on Dec. 13, 2011, now Pat. No. 9,265,649.

(60) Provisional application No. 61/422,578, filed on Dec. 13, 2010, provisional application No. 61/521,662, filed on Aug. 9, 2011, provisional application No. 61/541,974, filed on Sep. 30, 2011.

(51) Int. Cl.
*A61F 5/56* (2006.01)
*A61B 5/00* (2006.01)
*A61B 5/107* (2006.01)
*A61B 17/064* (2006.01)

(52) U.S. Cl.
CPC ............... *A61F 5/56* (2013.01); *A61B 5/0031* (2013.01); *A61B 5/107* (2013.01); *A61F 5/566* (2013.01); *A61B 5/1072* (2013.01); *A61B 5/1075* (2013.01); *A61B 5/1077* (2013.01); *A61B 17/064* (2013.01); *A61B 2017/0649* (2013.01)

(58) Field of Classification Search
USPC ............ 128/848, 859–862; 433/6–7; 602/902
See application file for complete search history.

(56) References Cited

U.S. PATENT DOCUMENTS

| | | | |
|---|---|---|---|
| 8,146,600 B2 * | 4/2012 | Pflueger et al. ............... | 128/848 |
| 8,776,799 B2 * | 7/2014 | Gillis et al. ................... | 128/848 |
| 2008/0035158 A1 * | 2/2008 | Pflueger et al. ............... | 128/848 |
| 2011/0226263 A1 * | 9/2011 | Gillis ........................ | A61F 2/00 |
| | | | 128/848 |

\* cited by examiner

*Primary Examiner* — Ophelia A Hawthorne
(74) *Attorney, Agent, or Firm* — William A. English; Vista IP Law Group LLP

(57) ABSTRACT

Apparatus and methods are provided for treating sleep apnea, snoring, and the like using an implant within an oropharyngeal region adjacent an anterior longitudinal ligament. The implant may include a central region between first and second outer regions. In one embodiment, one of the outer regions is compressible to allow the outer region to be directed through or behind the ligament such that the central region is disposed within or behind the ligament, the outer region being resiliently expandable after passing through or behind the ligament. In another embodiment, the implant may include one or more tines or other features that may be directed into adjacent tissue, e.g., the anterior longitudinal ligament and/or vertebra to secure the implant within the oropharyngeal region.

15 Claims, 34 Drawing Sheets

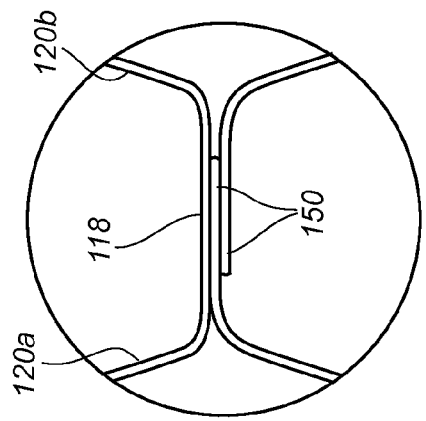
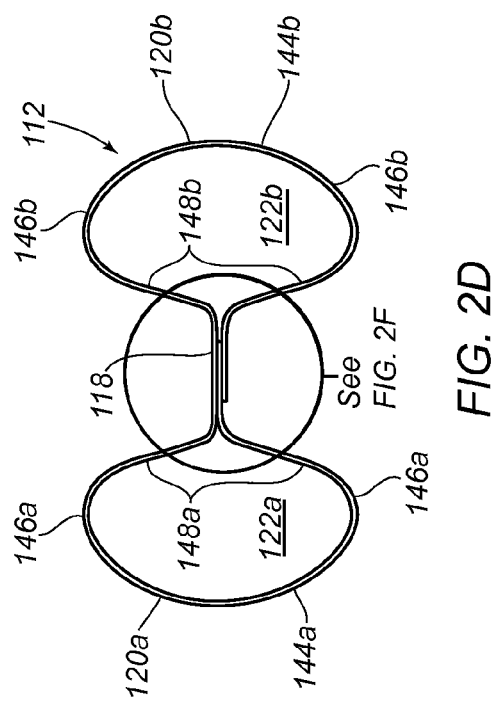
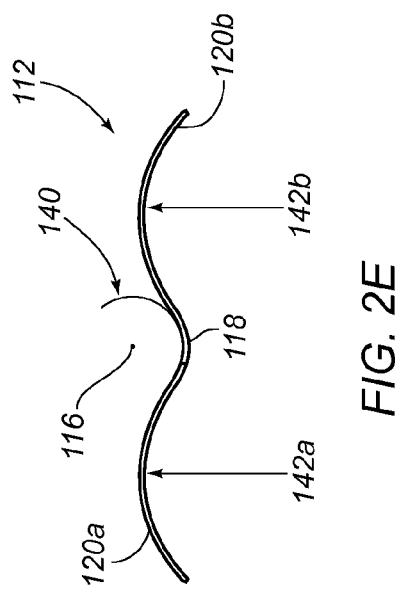

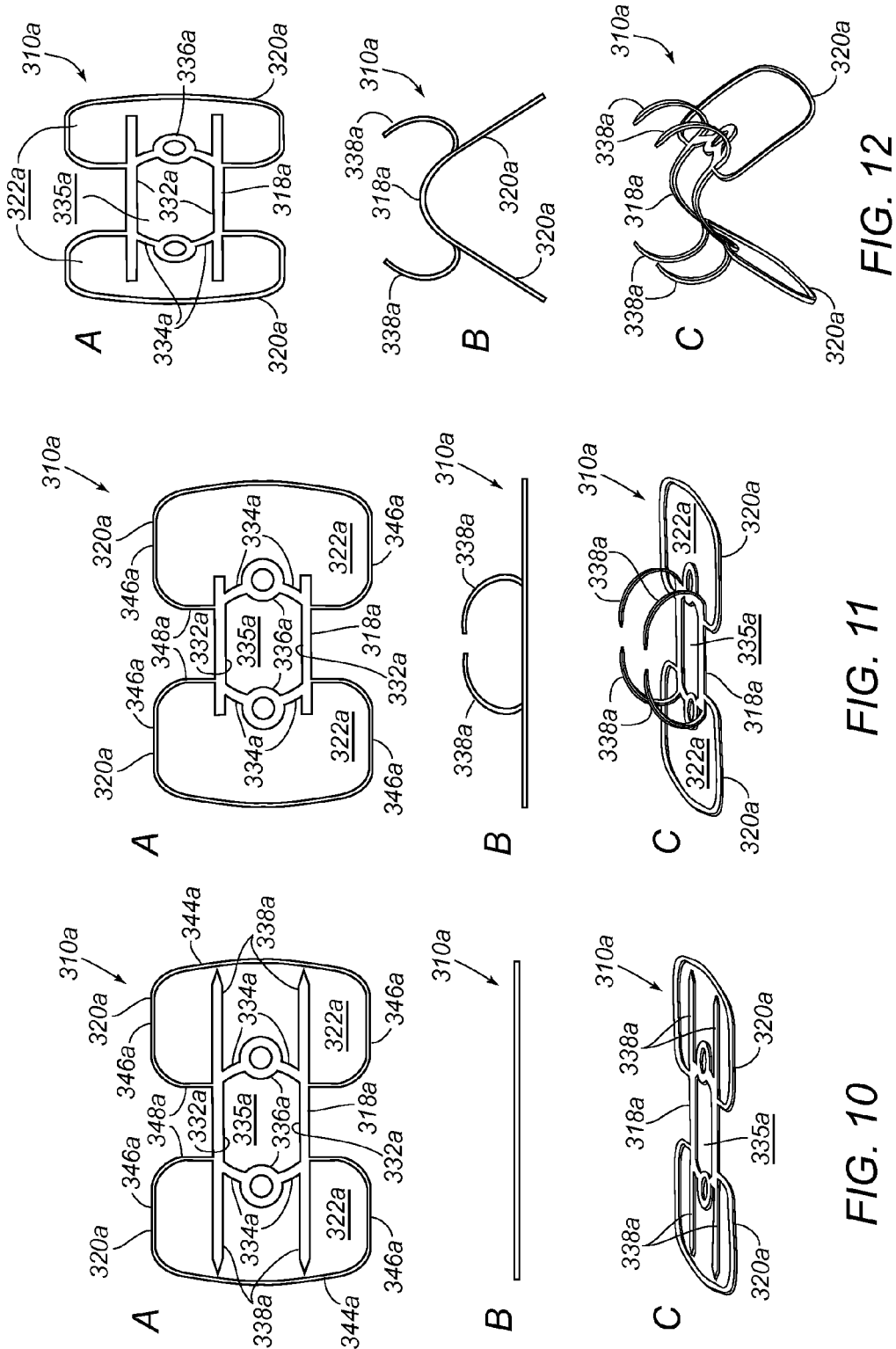

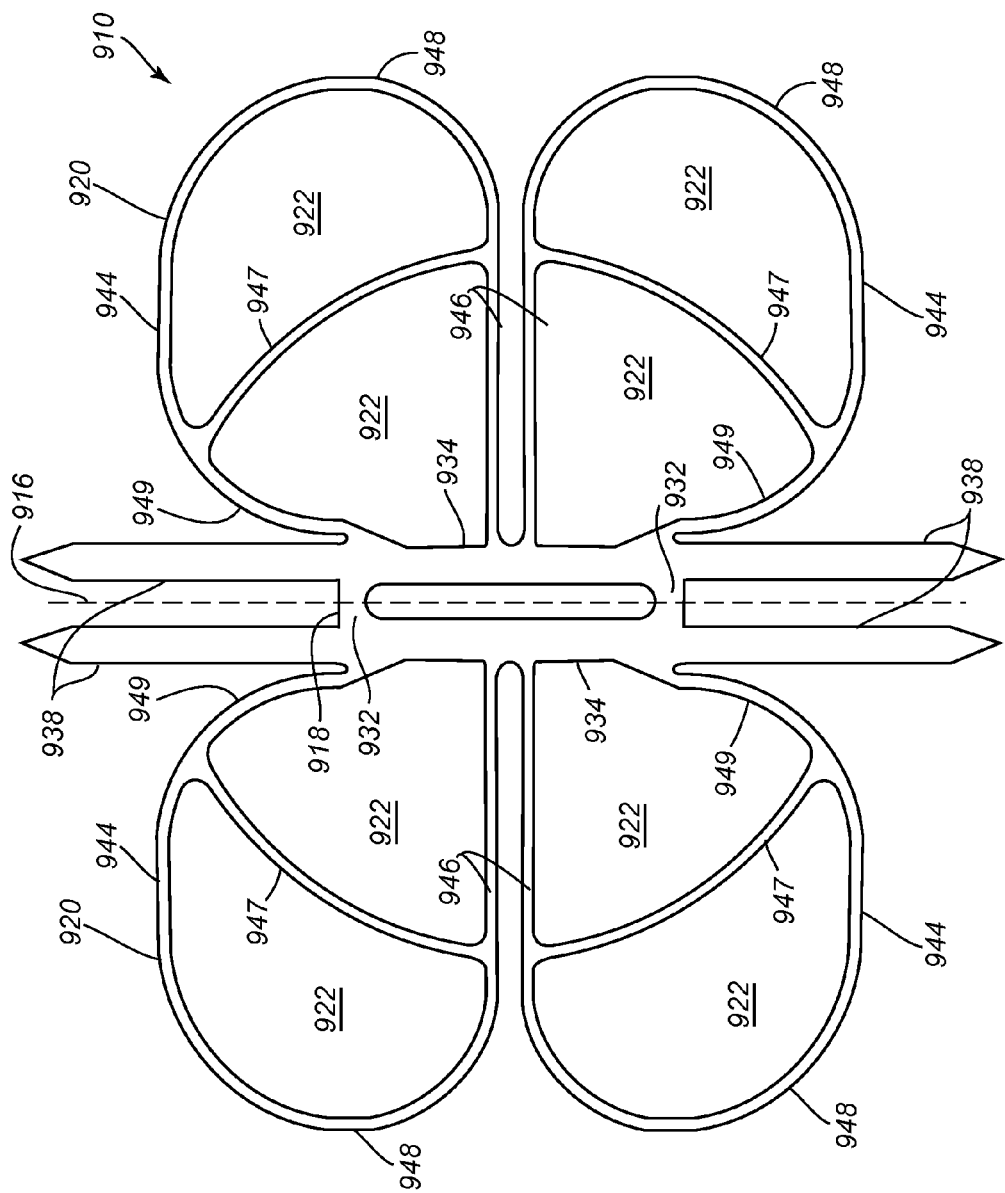

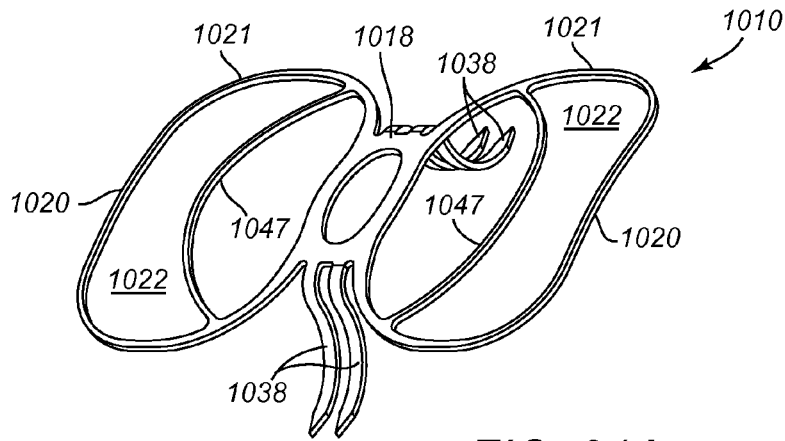
FIG. 21A
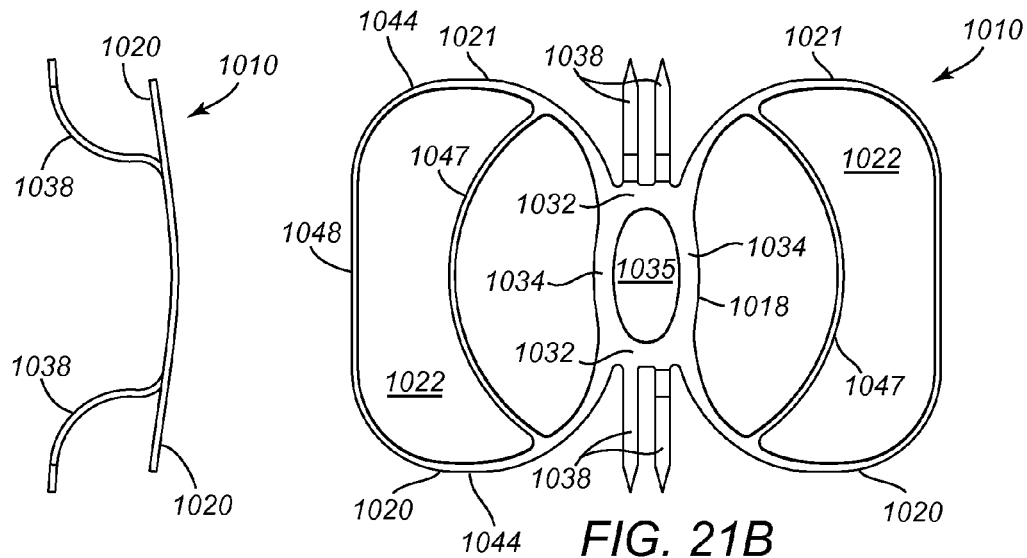
FIG. 21D
FIG. 21B
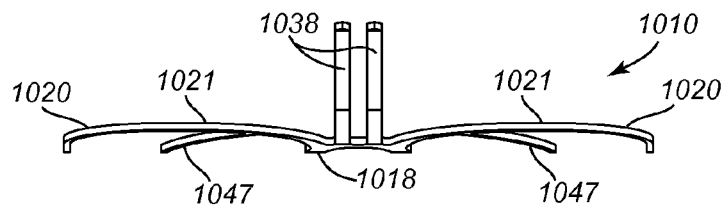
FIG. 21C

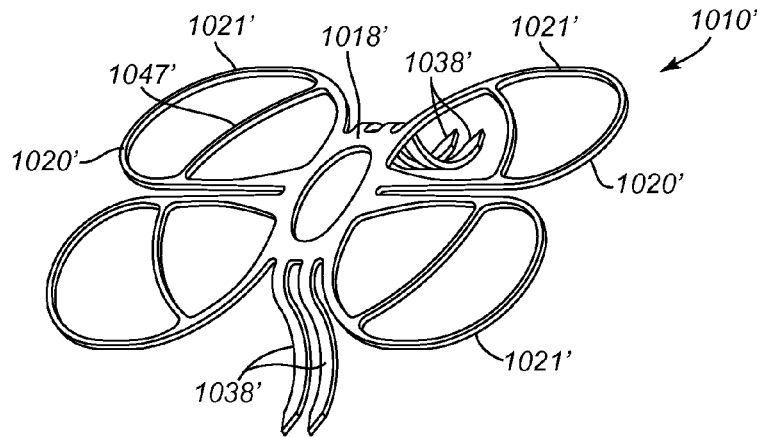
FIG. 22A
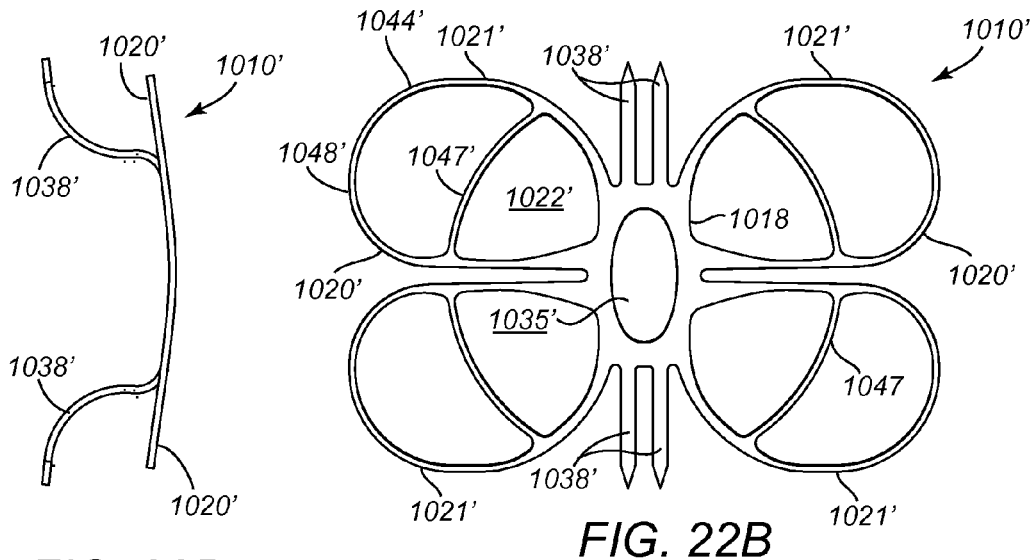
FIG. 22D
FIG. 22B
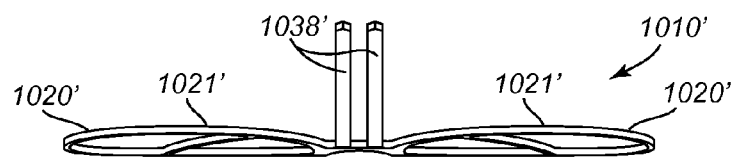
FIG. 22C

APPARATUS AND METHODS FOR TREATING SLEEP APNEA

RELATED APPLICATION DATA

This application is a continuation-in-part of co-pending application Ser. No. 13/324,764, filed Dec. 13, 2011, which claims benefit of provisional application Ser. Nos. 61/422,578, filed Dec. 13, 2010, 61/521,662, filed Aug. 9, 2011, and 61/541,974, filed Sep. 30, 2011. The entire disclosures of these applications are expressly incorporated by reference herein.

FIELD OF THE INVENTION

The present invention generally relates to apparatus and methods for treating sleep apnea, snoring, and/or other breathing disorders, and more specifically relates to apparatus for placement in the oropharyngeal region of a human or animal and to methods for treating sleep apnea, snoring, and/or other breathing disorders.

BACKGROUND

Sleep apnea is a sleep-related breathing disorder that is thought to affect between one and ten percent (1-10%) of the adult population. Recent epidemiologic data indicate that two percent (2%) of women and four percent (4%) of men between the ages of thirty (30) and sixty (60) years old meet the minimum diagnostic criteria for sleep apnea syndrome, representing more than ten million individuals in the United States. It is a disorder with significant morbidity and mortality, contributing to increased risk of hypertension, cardiac arrhythmias, stroke, and cardiovascular death. Another common sleep-related breathing disorder is snoring, which may be associated with or independent of sleep apnea.

One of the main reasons for sleep disturbance is relaxation of the tongue and pharyngeal walls to varying degrees during the several stages of sleep. When fully awake, these tissues have normal tone as air passes in and out of the lungs during respiration. However, during sleep, the musculature supporting these tissues relaxes. As air is inspired, the tongue and walls of the pharynx collapse, causing snoring or more seriously, causing partial or complete obstruction of the airway.

Obstructive sleep apnea occurs due to a collapse of soft tissue within the upper airway during sleep. The ongoing force of inspiration serves to generate increasingly negative pressure within the pharynx, causing further collapse. The lack of respiration results in inadequate blood oxygenation, and rising carbon dioxide levels. The cardiovascular response produces an increase in blood pressure and pulse. Cardiac arrhythmias often occur. The carbon dioxide increase and oxygen desaturation triggers a transition to a lighter sleep stage, usually without wakefulness. This transition brings a return to tonicity of the muscles of the upper airway, allowing normal breathing to resume. The person then returns to deeper stages of sleep and the process is repeated. The disease is quantified in terms of respiratory disturbances per hour. Mild disease begins at ten per hour, and it is not uncommon to find patients with indices of about one hundred or more.

Not surprisingly, sleep is extremely fragmented and of poor quality in persons suffering from sleep apnea. As a result, such persons typically feel tired upon wakening and may fall asleep at inappropriate times during the day. All aspects of quality of life, from physical and emotional health, to social functioning are impaired by obstructive sleep apnea.

Continuous Positive Airway Pressure ("CPAP") is a popular non-surgical treatment for patients suffering from sleep apnea. CPAP is administered by means of a mechanical unit that delivers pressurized room air to the nasal passage, or airway, through a nose mask that is worn by the patient during sleep. Pressurized air enters from the CPAP unit through the nose when a person is sleeping, and opens the airway from the inside almost as if the air were an internal splint. The correct pressure for the individual is determined in a sleep laboratory. If the nasal airway admits the flow of air, CPAP has in many cases offered immediate relief. Unfortunately however, compliance with, and long-term acceptance of this treatment are generally poor. Studies have shown that between twenty and fifty percent (20-50%) of patients fail to use nasal CPAP as prescribed. Problems associated with CPAP include excessive dryness of the mouth and throat, mucous congestion, sinusitis, and rhinorrhea. Breathing against positive air pressure is also discomforting to many patients.

Other non-surgical treatments for sleep apnea include the use of tongue retaining devices and other oral appliances that hold and/or pull the tongue or jaw in a forward position to open the airway by reducing collapse of the soft palate and/or tongue. These devices also suffer from poor compliance rates, and are usually associated with degenerative changes in the temporomandibular joint.

Surgical procedures have also been proposed and/or practiced for the treatment of moderate to severe sleep apnea. Uvulopalatopharyngoplasty ("UPPP") is a surgical procedure used to treat obstructive sleep apnea. In UPPP, any remaining tonsillar tissue and a portion of the soft palate is removed. The procedure increases the width of the airway at the throat opening. However, UPPP does not address apnea caused by obstructions deeper in the throat and airway, for example, apnea resulting from collapse of tissue near the base of tongue or in the oropharyngeal region of the airway.

LAUP, or Laser-Assisted Uvulopalatoplasty, is a modification of the above-mentioned technique, but has not proven particularly useful for sleep apnea. These surgical techniques are extremely invasive, requiring general anesthesia, and a prolonged, painful recovery.

Radio frequency tissue ablation ("RFTA") has also been suggested for shrinking the soft palate, uvula and reducing tongue volume in the treatment of snoring and obstructive sleep apnea. Somnoplasty utilizes a radiofrequency tool that generates heat to create coagulative lesions at specific locations within the upper airway. The lesions created by the procedure are naturally resorbed in approximately three to eight weeks, reducing excess tissue volume and increasing the airway opening. Like UPPP and LAUP, more than one session is typically required and it does not address sleep apnea resulting from tissues deeper in the throat than the upper airway.

Another area of surgical interest lies in techniques designed to pull the tongue anteriorly. For example, a tongue suspension procedure has been suggested in which the tongue is pulled forward, thereby keeping the tongue from falling into the airway during sleep. The system utilizes a bone screw inserted into the mandible. The screw attaches to a non-absorbable suture which travels the length of the tongue and back. Similarly, the hyoid bone can be drawn anteriorly with two distinct screws, also attached to the mandible.

Techniques have also been developed for treating, specifically, the condition of snoring. For example, U.S. Pat. No. 6,250,307 to Conrad et al. discloses a method for treating snoring of a patient that includes embedding a fibrosis-inducing implant into a soft palate of a patient in order to alter a dynamic response of a soft palate to airflow.

Concepts relating to implants in the pharyngeal area have been described in German publication DE 19,920,114 to Fege, published Nov. 9, 2000, which discloses transverse implant bands attached at one end to the cervical vertebra via surgical slits through the tongue, tonsils, and pharyngeal tissue. Other pharyngeal implants have been described in U.S. Publication No. 2003/0149488 to Metzger et al., now U.S. Pat. No. 7,017,582.

These conventional devices and treatments continue to suffer poor cure rates. The failures may lie in their inability to maintain patency in the retropalatal region and retroglossal region (the caudal margin of the soft palate to the base of the epiglottis). The poor success rates combined with high morbidity, contribute to an ongoing need for more effective treatments for sleep apnea and/or snoring.

SUMMARY

The present invention is directed to apparatus and methods for treating human subjects, for example, to substantially eliminate or at least reduce the occurrence of sleep apnea, snoring, and/or other sleep-related breathing disorders. The apparatus and methods may be relatively straightforward in structure and use, may be minimally invasive, and/or may provide substantial benefits over conventional techniques in controlling sleep apnea and/or snoring.

In accordance with one embodiment, a system is provided for implantation within an oropharyngeal region that includes an implant including a central region between first and second outer regions, the outer regions defining lobes surrounding respective open interior spaces on either side of the central region. In an exemplary embodiment, the implant may generally define a plane in a substantially flat configuration, and the outer regions may be displaceable out of the plane, e.g., such that the implant defines a curved configuration, for introduction into an oropharyngeal region. The central region may include one or more features, e.g., one or more apertures therethrough, and one or more fasteners may be engaged with the features, e.g., receivable through respective apertures, for securing the central region to tissue adjacent an oropharyngeal region.

In accordance with another embodiment, an apparatus is provided for implantation within an oropharyngeal region that includes an implant including a central region between first and second outer regions, the outer regions defining lobes surrounding respective open interior spaces on either side of the central region; and a pair of tabs on the central region including apertures therethrough for receiving respective fasteners to secure the central region to tissue adjacent an oropharyngeal region.

In accordance with yet another embodiment, an apparatus is provided for implantation within an oropharyngeal region that includes an implant including a central region between first and second outer regions, the outer regions defining lobes surrounding respective open areas on either side of the central region, and one or more, e.g., a pair of, apertures extending through the central region for receiving respective fasteners to secure the central region to tissue adjacent an oropharyngeal region. The outer regions may be displaceable towards one another such that the implant defines a generally "C" shaped curved configuration and/or biased towards a substantially flat configuration to apply a force to dilate tissue adjacent the oropharyngeal region when the implant is disposed within the oropharyngeal region.

In accordance with still another embodiment, a method is provided for treating an oropharyngeal region of a patient that includes directing an implant including first and second outer regions separated by a central region into the oropharyngeal region in a curved configuration; positioning the central region adjacent a posterior wall of the oropharyngeal region; directing one or more fasteners through the central region into tissue adjacent the posterior wall; and releasing the implant within the oropharyngeal region such that the outer regions apply a force to dilate tissue adjacent the oropharyngeal region.

In accordance with another embodiment, an apparatus is provided for implantation within an oropharyngeal region adjacent a ligament that includes an implant including a relatively narrow central region between first and second relatively wide outer or end regions. The outer regions may be foldable, rollable, compressible, or otherwise displaced out of plane towards one another such that the implant defines a generally "C" shape about a vertical axis. In addition, the outer regions may be biased to open away from the vertical axis such that the first and second regions apply a force to dilate tissue adjacent the oropharyngeal region when the implant is disposed within the oropharyngeal region.

The outer regions may be compressible vertically. The outer region(s) may be resiliently expandable to return towards their original relatively wide configuration. Optionally, the outer regions may define an open area on either side of the central region, e.g., including mesh, struts, or other features, if desired.

Optionally, a sleeve may surround at least a portion of the central region. In addition or alternatively, one or more features may be provided on the central region, e.g., one or more tines, pins, and the like, for engaging tissue adjacent an oropharyngeal region. In some embodiments, the central region may be a separate component that is placed initially in vivo to which the outer region may be assembled secondarily in situ. The assembly of the outer region to the central region may be accomplished using various connectors, fasteners, and/or methods, e.g., by mechanical, chemical, suturing, or magnetic means.

In accordance with another embodiment, an apparatus is provided for implantation within an oropharyngeal region adjacent a ligament that includes an implant including a central region between first and second ends, and one or more features or elements on the central region for engaging tissue to secure the implant within the oropharyngeal region. In one embodiment, the implant may have an oval or oblong shape defining an open area surrounded by a periphery, and may include a major axis between the first and second ends and a minor axis extending across the central region. In another embodiment, the implant may include a relatively narrow central region between first and second relatively wide outer regions adjacent the first and second ends. Optionally, one or more struts may extend across the open area, e.g., across the central region and/or across outer regions adjacent the first and second ends.

The one or more features may include sets of tines, for example, opposite one another on the periphery of the implant, e.g., across the central region. For example, the tines may be substantially rigid and/or may extend substantially perpendicular to the plane of the implant. Alternatively, the tines may be biased to extend transversely, e.g., diagonally relative to the plane of the implant. For example, the tines may be biased to extend away from one another or may extend towards one another, e.g., such that their ends at least partially cross one another, yet may be resiliently directed to a substantially perpendicular orientation to facilitate insertion into tissue. In an exemplary embodiment, the tines may be biased to a curved configuration yet may be resiliently directly to a substantially straight configuration to facilitate insertion into tissue. In another embodiment, the one or more features may include one or more apertures through the central region and corresponding fasteners, e.g., one or more staples, screws, sutures, and the like, receivable through respective apertures for engaging tissue, e.g., the anterior longitudinal ligament and/or vertebrae, adjacent the posterior wall of the oropharyngeal region.

In accordance with yet another embodiment, an apparatus is provided for implantation within an oropharyngeal region adjacent a ligament that includes an implant including a plurality of implant components that are connectable together to define a relatively narrow central region between first and second relatively wide outer regions, e.g., defining an open area on either side of the central region. In one embodiment, a pair of implant components may be provided that are connectable at the central region such that each implant component includes one of the outer regions. For example, the central region of a first implant component may be configured to be introduced through or behind an anterior longitudinal ligament, and the central region of a second implant component may be connectable to the first implant component such that the outer regions are disposed on either side of the ligament.

In accordance with another embodiment, the central region of the implant may be attached to the ligament through the use of anchoring screws, coils, or other attachments. These anchoring coils may be manually screwed into the tissue securing the central region of the implant to the ligament or they may thread into the tissue automatically. Similar to a wound spring, these coils may unwind and be forced to thread into tissue upon release. These coils may be separate components or integral to the central region. The coils may be configured to attach the central region or the entire implant, e.g., central and outer regions combined, in one step. In addition, the coils may be attached to portions of the outer regions of the implant if desired.

In accordance with still another embodiment, an implant is provided that includes a relatively narrow central region between first and second relatively wide outer regions, e.g., each defining a substantially enclosed open area. The outer regions are compressible vertically to allow them to be directed through or behind the ligament adjacent the oropharyngeal region such that the central region is disposed within or behind the ligament. Optionally, the central region may include a sleeve at least partially surrounding the central region and/or one or more features for engaging tissue adjacent the implant, e.g., for securing the implant relative to the tissue.

In accordance with another embodiment, an implant is provided that includes an enclosed loop structure including a relative narrow central region between relative wide first and second regions. The first and second regions may be rollable, foldable, compressible, or otherwise displaced out of plane towards one another such that the implant defines a generally "C" shape about a vertical axis, the first and second regions being biased to open away from the vertical axis, e.g., to a substantially planar configuration, when unconstrained such that the first and second regions apply a force to dilate tissue adjacent the oropharyngeal region when the implant is disposed within the oropharyngeal region. Optionally, at least one of the first and second regions may be compressible vertically to allow the at least one of the first and second regions to be directed through or behind the ligament adjacent the oropharyngeal region such that the central region is disposed within or behind the ligament, the at least one of the first and second regions being resiliently expandable after passing through or behind the ligament.

In accordance with still another embodiment, a system is provided for treating sleep apnea, snoring, and/or other breathing disorders that includes an implant including a relatively narrow central region between relatively wide first and second regions, and a needle coupled to the first end region by a filament for insertion through tissue and/or a ligament adjacent an oropharyngeal region. At least the first region may be compressible vertically to allow the first region to be directed through or behind the ligament the needle and filament are inserted through or behind the ligament such that the central region is disposed within or behind the ligament, the first region being resiliently expandable after passing through or behind the ligament. The first and second regions may also foldable, rollable, compressible or otherwise displaceable towards one another such that the implant defines a generally "C" shape about a vertical axis. The first and second regions may be biased to open away from the vertical axis within the horizontal plane when unconstrained such that the first and second regions apply a force to dilate tissue adjacent the oropharyngeal region when the implant is disposed within the oropharyngeal region. The first and second regions may increase a surface area contacting adjacent tissue, which may facilitate dilating, opening, or otherwise treating tissue adjacent the oropharyngeal region. Other automated tools may be used to pass a needle and filament through or behind the ligament. Such tools may control the depth, penetration force, and/or width of the needle pass through or behind the ligament.

The implants, apparatus, and/or systems herein may include any material or materials suitable for placement in the pharyngeal region that may be effective to reinforce tissues of the region in order to provide support to these tissues against collapse such that a patient can breathe more effectively than the patient would breathe without the material or materials placed in the region. For example, the implants may be formed from pre-shaped wire that may be biased to a predetermined shape but elastically deformable to facilitate introduction and/or implantation within a patient's body. Alternatively, the implants may be formed from a sheet, e.g., by laser-cutting, machining, etching, or otherwise removing undesired regions of the sheet to create the desired implant. In an exemplary embodiment, the implant may be formed from elastic material, such as a super-elastic material, e.g., Nitinol, or other metals, such as stainless steel, elgiloy, titanium, polymers, or composite materials.

Tissue engagement may be enhanced by making the implant features porous for tissue in-growth or made from a biocompatible material that elicits tissue in-growth such as materials made with polyester or porous ceramic, spring steel, and the like. Alternatively, the surface of the implant may be coated with one or more pharmaceutical or biological agents, e.g., to promote or retard reactions by the surrounding tissue and blood circulation such as: tissue in-growth, tissue encapsulation, reduction of tissue proliferation, enhanced mucosalization, and/or other potentially beneficial effects.

In accordance with another embodiment, a method is provided for treating sleep apnea or snoring within an oropharyngeal region adjacent an anterior longitudinal ligament that includes introducing an implant into the oropharyngeal region, the implant comprising a relatively narrow central region between relatively wide first and second regions. The first region may be introduced through an opening through or behind the ligament, while compressed vertically from a relaxed configuration as the first region passes through the opening. After the first region passes through the opening, the first region may resiliently expand towards the relaxed configuration, the central region remaining within the opening.

In accordance with yet another embodiment, an apparatus is provided for implantation within an oropharyngeal region that includes an implant including a central region between first and second outer regions generally defining a plane in a substantially flat configuration. The outer regions may define lobes surrounding respective open interior spaces on either side of the central region. The outer regions may be displaceable out of the plane such that the implant defines a curved configuration; and a first pair of opposing tines may be provided on the implant including tips oriented towards one another adjacent the central region in the substantially flat configuration, the tips being directed away from one another when the implant is directed to the curved configuration to define a space therebetween for receiving tissue when the implant is introduced into an oropharyngeal region. The outer regions may be biased towards the substantially flat configuration to apply a force to dilate tissue adjacent the oropharyngeal region when the implant is disposed within the oropharyngeal region and to direct the tines towards one another to engage tissue received within the space between the tips.

In accordance with still another embodiment, an apparatus is provided for implantation within an oropharyngeal region adjacent a ligament that includes an implant including a central region between first and second outer regions, the outer regions defining lobes and defining a substantially flat configuration in a relaxed state lying generally within a plane, the outer regions biased towards the substantially flat configuration to apply a force to dilate tissue adjacent the oropharyngeal region when the implant is disposed within the oropharyngeal region; and one or more pairs of tines extending transversely from the central region out of the plane in the relaxed state to define a transverse orientation, the tines resiliently directable to a delivery orientation wherein tips of the tines extend substantially perpendicular to the plane, the tines biased to return towards the transverse orientation.

In accordance with another embodiment, a system is provided for treating at least one of sleep apnea and snoring that includes an implant and a tool. The implant may include a central region between first and second outer regions, the outer regions defining lobes and defining a substantially flat configuration lying generally within a plane, the outer regions biased towards the substantially flat configuration to apply a force to dilate tissue adjacent the oropharyngeal region when the implant is disposed within the oropharyngeal region; and one or more screws, clips, sutures, or other fasteners receivable through the central region out of the plane. The tool may include an elongate shaft including a proximal end and a distal end sized for introduction into an oropharyngeal region, and one or more features on the tool distal end for engaging the screws to direct the screws through the central region into adjacent tissue, e.g., adjacent the posterior wall of an oropharyngeal region. Optionally, the implant may also loaded onto the tool distal end. For example, the tool may also include an engaging member for holding the implant at the tool distal end and a tip to engage a head of the screw to turn the screw threads into the tissue adjacent the central region.

In accordance with still another embodiment, a method is provided for treating at least one of sleep apnea and snoring using an implant including a central region between first and second outer regions, the implant including one or more apertures in the central region such that screws may be deployed through the apertures and into tissue adjacent the central region, e.g., the anterior longitudinal ligament and/or vertebrae, to secure the implant to the posterior wall of an oropharyngeal region. The implant may be directed to a curved configuration to facilitate introduction into the oropharyngeal region, and/or the outer regions may be biased to curve towards or away from the pharyngeal wall, e.g., to provide a desired biasing and/or supporting force on adjacent tissue. The screws may be directed into tissue adjacent the posterior wall of the oropharyngeal region, e.g., through mucosal tissue, muscle tissue, the anterior longitudinal ligament, and/or into a vertebra or spinal disc, to secure the central region of the implant within the oropharyngeal region. The implant may be secured within the oropharyngeal region such that the outer regions resiliently apply a force against the lateral walls of the oropharyngeal region and/or become mucosalized, e.g., within weeks.

In accordance with yet another embodiment, a method is provided for treating at least one of sleep apnea and snoring using an implant including a central region between first and second outer regions, the implant comprising one or more pairs of tines extending transversely from the central region in a transverse orientation in the relaxed state. The implant may be loaded onto a delivery tool such that the tines are directed to a delivery orientation wherein tips of the tines extend substantially perpendicular from the central region, and the implant may be introduced into an oropharyngeal region of a patient in the curved configuration. The implant may be deployed from the tool such that the tips of the tines are directed into tissue adjacent the posterior wall of the oropharyngeal region, the tines resiliently returning towards the transverse orientation as they enter the tissue.

In accordance with yet another embodiment, an implant system may be provided that includes a first implant defining a central region configured for tissue attachment and a second implant defining outer regions configured to be docked or otherwise coupled to the first implant.

Each and every feature described herein, and each and every combination of two or more of such features, is included within the scope of the present invention provided that the features included in such a combination are not mutually inconsistent.

These and other aspects of the present invention are apparent in the following detailed description and claims, particularly when considered in conjunction with the accompanying drawings in which like parts bear like reference numerals.

BRIEF DESCRIPTION OF THE DRAWINGS

The drawings illustrate exemplary embodiments, in which:

FIGS. 2D and 2E are front and top views of the implant of FIGS. 2A-2C, showing various dimensions.

FIG. 2F is detail of the implant of FIGS. 2A-2E.

FIGS. 10A-12C are front, top, and perspective views of another embodiment of an implant, showing the implant as formed from a flat sheet (FIGS. 10A-10C), in its relaxed state (FIGS. 11A-11C), and in a cocked state to facilitate implantation (FIGS. 12A-12C).

FIGS. 20A-20C are top views of still another embodiment of an implant, showing the implant as formed from a flat sheet (FIG. 20A), in its heat-shaped relaxed state (FIG. 20B), and in a cocked state to facilitate implantation (FIG. 20C).

FIGS. 21A-21D are perspective, front, top, and side views, respectively, of yet another embodiment of an implant for treating sleep apnea, snoring, and/or other breathing disorders that includes tines for securing the implant to tissue biased to extend transversely relative to a plane of the implant.

FIGS. 22A-22D are perspective, front, top, and side views, respectively, of still another embodiment of an implant including tines for securing the implant to tissue biased to extend transversely relative to a plane of the implant.

DETAILED DESCRIPTION OF THE EXEMPLARY EMBODIMENTS

Generally, the apparatus and systems described herein include an implant, stent, or other appliance sized and/or structured to be placed in a given position in an oropharyngeal region of a human or animal patient, e.g., for treating sleep apnea, snoring, and/or other breathing or sleeping disorders of the patient.

Figure 1:
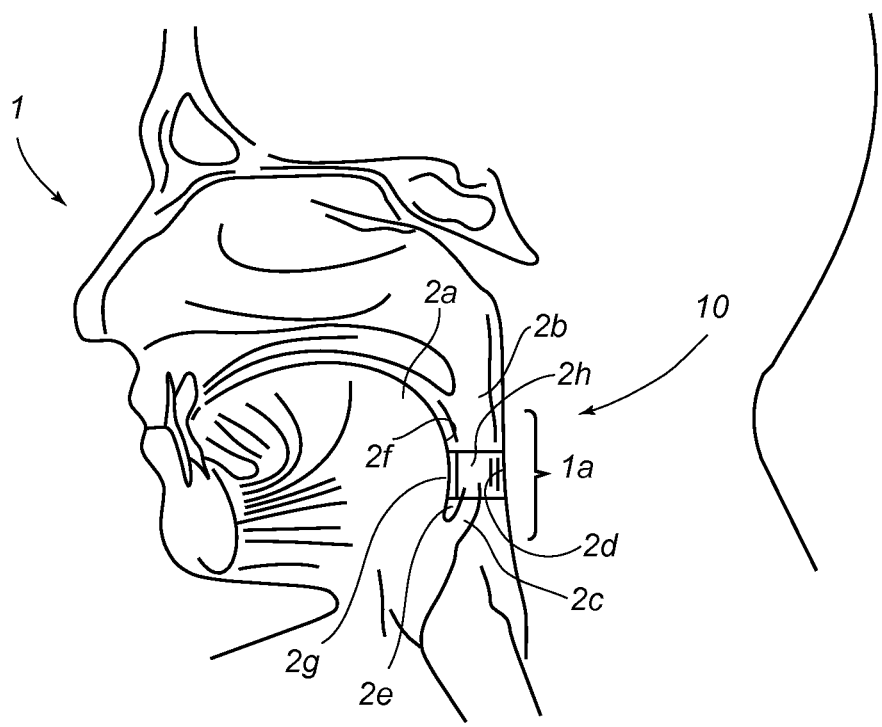
FIG. 1 is a cross-sectional view of a patient's head, showing an exemplary embodiment of an implant positioned in an oropharyngeal region of the patient.

Turning now to the drawings, FIG. 1 shows a cross-sectional anatomical view of a human patient or other subject 1. The patient 1 has an exemplary apparatus 10, which may be any of the embodiments described herein, located within the patient's oropharyngeal region 1a in order to substantially control, reduce, eliminate, and/or otherwise treat sleep apnea, snoring, and/or other breathing disorders.

Snoring and sleep apnea are often caused by a combination of narrowness and low muscle tone of the upper airways. The tongue 2a may fall back and obstruct the airway, possibly leading to an arousal reaction and disturbing the normal sleeping pattern. Other portions of the oropharyngeal region may also collapse. For example, the lateral walls 2b of the oropharyngeal region often become excessively lax and block a free flow of air during respiration. When the patient 1 is supine, i.e., when the patient 1 is asleep and lying on his/her back, the relaxed tongue 2a may move inferiorly (down) and posteriorly (back), and/or the lateral walls 2b of the oropharyngeal region may collapse inwardly resulting in a narrower pharynx relative to when the patient 1 is upright. One cause for the narrowing of the pharynx in the supine position may be that the oropharyngeal region 1a and hypopharyngeal region, which have low consistencies, collapse because of lack of direct hard tissue support.

The apparatus 10 may be secured to the oropharyngeal region by various methods. For example, the apparatus 10 may be elastically compressed to a smaller size to facilitate introduction, and released within the oropharyngeal region, whereupon the apparatus 10 may resiliently expand and thereby secure the apparatus 10 within the oropharyngeal region. Optionally, the apparatus 10 may be secured at least partially relative to the longitudinal anterior ligament or within or through other tissues (not shown), e.g., using one or more tines or other features (not shown) on the apparatus 10 that may be delivered into or through tissue adjacent the oropharyngeal region, e.g., into the ligament and/or an adjacent vertebra, as described elsewhere herein. For example, a central region of the apparatus 10 may be placed through or behind the anterior longitudinal ligament, or the central region of the apparatus 10 may include one or more features that engage the ligament, bone, or other tissue adjacent the poster wall of the oropharyngeal region 1a.

Alternatively, the apparatus 10 may be sutured to the oropharyngeal region, e.g., with bioabsorbable sutures, which may allow the apparatus 10 to be held in place while the apparatus 10 becomes fixed to the region by means of tissue ingrowth. In a further alternative, separate fasteners, e.g., clips, staples, sutures, screws and the like (not shown), may be used to secure the apparatus 10 to the oropharyngeal region or to a second implant (also not shown). In addition or alternatively, the apparatus 10 may be secured to the region using a biocompatible adhesive. Alternatively still, the apparatus 10 may be secured to the region by being surgically implanted into the region, e.g., directly beneath the region's mucosal layer, for example, by being pulled, with a surgical needle at least partially into and/or beneath the mucosal layer such that the apparatus 10 at least partially circumscribes the region.

The apparatus 10 may be designed to provide direct support to at least some of these tissues when the patient 1 is supine and/or asleep or such that the physical presence of the apparatus 10 itself may stimulate muscle tone arousal to support these tissues. For example, the apparatus 10 may be structured so that when placed in a desired position in the oropharyngeal region 1a, the apparatus 10 may push the tongue forward, and/or push the lateral walls 2b outwardly away from one another, thereby holding the airway patent or open during the time the patient 1 is naturally sleeping.

As shown, the apparatus 10 may be sized and structured to be positioned above or adjacent the epiglottis 2c of the patient 1, e.g., but without coming in contact with the epiglottis 2c. For example, in one embodiment, the apparatus 10 is designed to overlay a posterior wall 2d of the oropharyngeal region 1a and provide an opening force outwardly against opposing lateral walls 2b of the oropharyngeal region 1a. For example, the apparatus 10 may be implanted within the oropharyngeal region 1a above the epiglottis 2c, e.g., laterally adjacent the C1-C4 vertebrae, e.g., laterally adjacent or between the C2-C3 vertebrae (not shown). In other embodiments, the apparatus 10 may be designed to be placed opposite or below the soft palate, or within a valecullar space 2e, and/or may provide a pushing force against the base 2f of the tongue 2a, which makes up a portion of the anterior wall 2g of the oropharyngeal region 1a. The valecullar space 2e, as the term is used herein, is defined as being the space between the anterior wall 2g of the throat and the upper tip 2h of the epiglottis 2c down to the conjunction of the epiglottis 2c with the anterior wall 2g of the pharynx.

In any event, the apparatus 10 may be designed in such a manner as to substantially prevent the apparatus 10 from interfering substantially with the normal functioning of the tissue around the apparatus 10, particularly with the normal functioning of the epiglottis 2c. Optionally, the apparatus 10 may include features, structures, or other elements (described elsewhere herein) for anchoring or securing the apparatus 10 within the oropharyngeal region 1a, e.g., to prevent the apparatus 10 from migrating substantially away from or out of a given position in which the apparatus 10 is implanted. The apparatus 10 may be structured to closely and flexibly conform to the size and contours of at least a portion of the oropharyngeal region 1a.

Figure 2A:
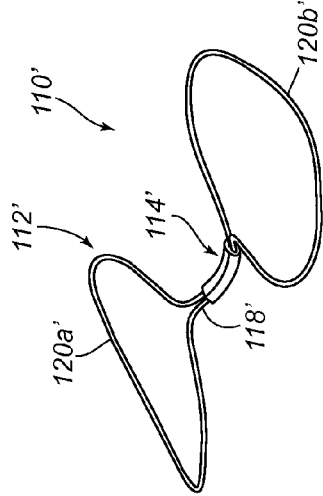
FIGS. 2A-2C are perspective, front, and top views, respectively, of an exemplary embodiment of an implant for treating sleep apnea, snoring, and/or other breathing disorders.
Figure 2B:
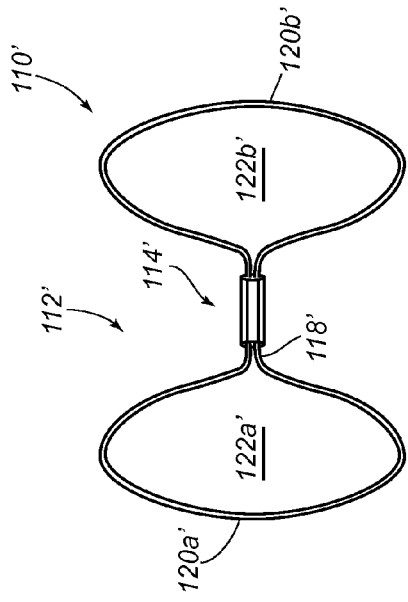
Figure 2C:
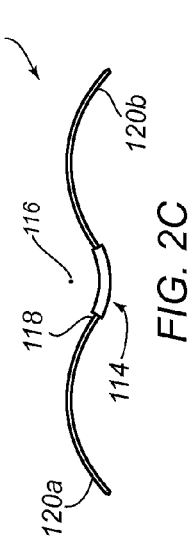

Turning to FIGS. 2A-2C, an exemplary embodiment of an apparatus 110 is shown that generally includes an implant, stent, or appliance 112 that is foldable, rollable, compressible, or otherwise displaceable about a vertical axis 116, and optionally a sleeve 114 extending along a central portion 118 thereof. Optionally, the apparatus 110 may include other features, such as a needle 130 and/or suture 132, e.g., shown in FIGS. 4A and 4B, or other delivery device (not shown), as described elsewhere herein.

From a front view, shown in FIG. 2B, the implant 112 has a generally "bow-tie" shape, i.e., including a relatively narrow central region 118 flanked by relatively wide or broadened first and second outer regions 120, "width" defined in a generally vertical direction, i.e., along the vertical axis 116. In addition, from a top view, shown in FIG. 2C, the implant 112 may have a curved shape in a direction perpendicular to the vertical axis 116. For example, as best seen in FIG. 2E, the central region 118 may curve generally around the vertical axis 116 to define a first radius of curvature 140, while the first and second regions 120 curve away from the vertical axis 116 to define a second radius of curvature 142. Thus, the implant 112 may define a generally "gull wing" shape when viewed from the top or bottom. Alternatively, the central region 118 and the outer regions 120 may both curve around the vertical axis 116, e.g., in a substantially continuous "C" shaped curve, which may be a portion of a circle or ellipse (not shown), similar to implants disclosed in U.S. Publication No. 2008/0035158 and/or U.S. Pat. Nos. 7,381,222 and 7,992,566, the entire disclosures of which are incorporated by reference herein. In further alternatives, the central region 118 and/or the outer regions 120 may be substantially planar, e.g., such that the entire implant 112 lies substantially within a plane (not shown).

As best seen in FIG. 2D, the outer regions 120 may include outer curved segments 144, e.g., defining a portion of a circle or ellipse, and segments 146 connecting ends of the curved segments 144 to the central region 118. Alternatively, one or both of the outer curved segments 144 may include a rounded tip (not shown) extending outwardly away from one another, e.g., as disclosed in the references incorporated by reference elsewhere herein. The outer curved segments 144 may be connected to the central region 118 by one or more segments, e.g., relatively smaller radius segments 146 and substantially straight segments 148, as shown in FIG. 2D. Thus, each set of segments 144, 146, 148 may substantially enclose an open area 122 within the respective outer region 120.

Figure 3A:
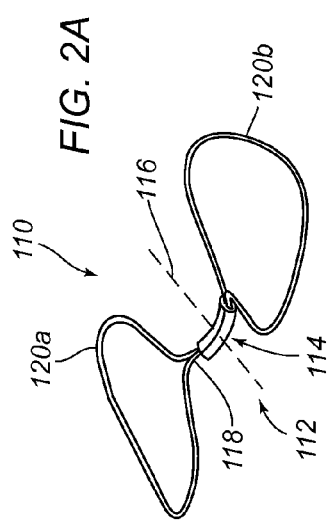
FIGS. 3A and 3B are perspective and front views, respectively, of another exemplary embodiment of an implant for treating sleep apnea, snoring, and/or other breathing disorders.
Figure 3B:
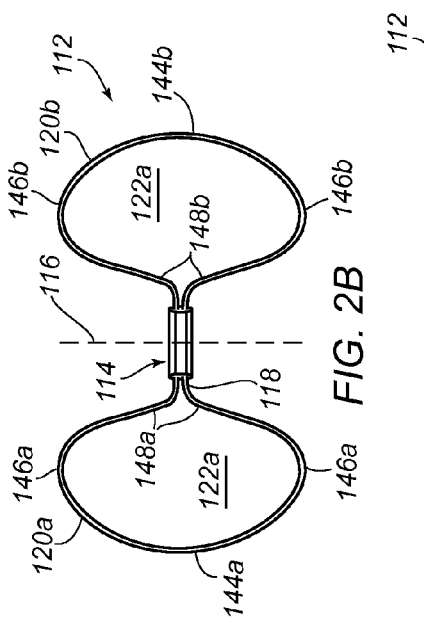

Alternatively, the outer regions 120 may have different shapes than that shown. For example, FIGS. 3A and 3B show an alternative embodiment of an apparatus 110' including an implant 112' having different dimensions than the implant 112, but otherwise similar in construction. In a further alternative, the outer regions may have diamond shapes in a relaxed state, e.g., extending between the central region and outer tips. In another alternative, the outer regions may have circular or elliptical shapes, e.g., with or without the narrow tips. In still another alternative, the outer regions may have generally triangular shapes, e.g., within one of the apices of the triangles oriented towards the central region and bases of the triangles defining outer ends of the implant. In yet another alternative, the outer regions may have generally rectangular, square, or other geometric shapes (not shown) that are larger than the narrower central region. In each of these alternatives, the open area 122 within the outer regions 120 may define a relatively large surface area, which may enhance apposition between the outer regions 120 and adjacent tissue.

Optionally, the open areas 122 of the implant 112 may include one or more struts (not shown) extending across the open areas 122 and/or the open areas 122 may be at least partially covered, e.g., with a flexible mesh, fabric, braid, membrane or other material, as disclosed in the references incorporated by reference elsewhere herein.

As best seen in FIGS. 2D-2F, the implant 112 may be formed from a single, continuous wire or other loop element 2014 that extends around the outer periphery of the implant 112 to define the central region 118 and outer regions 120 (including the segments 144-148). For example, the implant 112 may be formed from a length of round, square, or other cross-section wire, e.g., having a diameter or thickness dimension between about 0.008-0.015 inch.

In an exemplary embodiment, a wire may be bent or otherwise formed into the desired shape and the ends may be coupled to one another. For example, as best seen in FIG. 2F, the ends of the wire 150 may be attached together at the central region 118 of the implant, e.g., laser welded, sonic welded, soldered, heat sealed, and the like. Alternatively, the ends of the wire may be butt or lap welded and/or received and secured within a small tube (not shown) at the central region 118 or at another location of the implant 112, as desired. The resulting shaped wire may be heat-treated or otherwise treated to program in the desired shape and/or impart the desired elasticity and/or other properties into the resulting implant 112. Alternatively, the implant 112 may be formed from multiple sections of wire attached in similar manners. In a further alternative, the implant 112 may be formed from a sheet of material (not shown), e.g., by laser cutting, machining, etching, and the like, to remove sufficient material to provide the open areas, regions, and/or segments of the final implant, before or after programming a desired shape into the sheet.

As shown in FIGS. 2A-2C, the sleeve 114 may be provided around at least a portion of the central region 118, e.g., to cover the ends 150 and/or any welds or connection points of the wire forming the implant 112. The sleeve 114 may be provided from a biocompatible plastic or metal, e.g., polyetheretherketone (PEEK), and the like. For example, the sleeve 114 may be provided from a tubular material cut to the desired length corresponding to the central region 118, and directed over the wire before the wire is formed into the desired shape of the implant 112. Alternatively, the sleeve 114 may be directed over the wire after shaping but before attaching the ends 150 of the wire. In a further alternative, the sleeve 114 may be provided from a sheet of material that may be wrapped around the central region 118 and attached together to secure the sleeve 114 around the central region 118. The sleeve 114 may provide an increased surface area or profile for the central region, e.g., compared to the wire or other elements defining the central region 118, to reduce the risk of tearing or other damage to other tissue through which the central region 118 is placed, and/or may reduce friction and/or enhance biocompatibility of the implant 112.

Figure 4A:
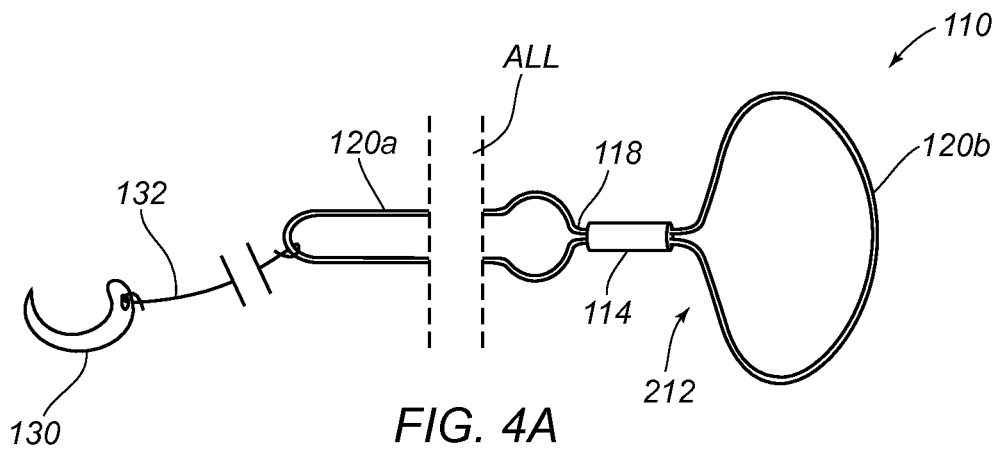
FIGS. 4A and 4B are details of the oropharyngeal region of FIG. 1, showing an implant being advanced through or behind the anterior longitudinal ligament "ALL."
Figure 4B:
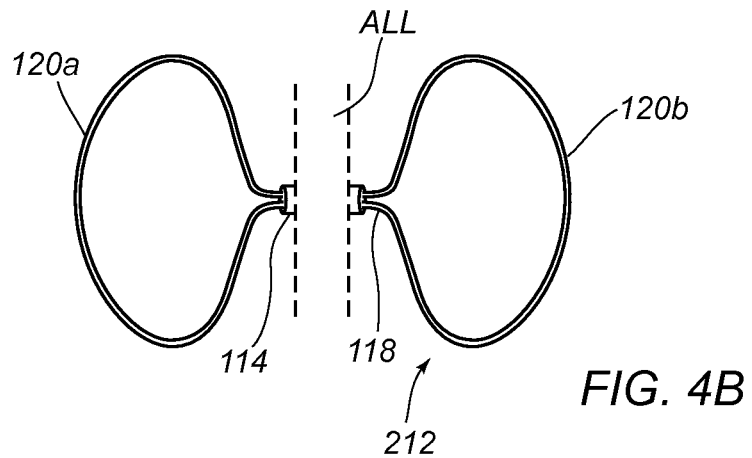

Turning to FIG. 1, with additional reference to FIGS. 4A and 4B, the apparatus 110 (and similarly any of the other embodiments described herein) may be structured to be implanted and/or otherwise placed within an oropharyngeal region 1a of a patient 1. The central region 118 may be positioned adjacent or within a posterior wall 2d of the oropharyngeal region 1a and the outer regions 120 may extend outwardly from the generally central region 118, e.g., around or within the lateral and/or anterior surface 2g of the oropharyngeal region 1a.

The implant 112 may be sufficiently resilient and/or elastic such that one or both of the outer regions 120 may be collapsed vertically from their relaxed state, e.g., as shown in FIGS. 2A and 2B, to a compressed state, e.g., as shown in FIG. 4A, when directed through a relatively small opening, yet biased to resiliently expand back towards the relaxed state after passing through the opening.

Optionally, as shown in FIG. 4A, a needle 130 may be coupled to one of the outer regions 120, e.g., by a suture or other filament 132, to provide a system for delivering the apparatus 2010 into the oropharyngeal region 1a of a patient 1. The needle 130 may have a "U" or other shape to facilitate introduction through or behind a ligament or other tissue structure adjacent the oropharyngeal region 1a, and/or the suture 132 may be a double suture looped through the needle 130 and outer region 120, as disclosed in the references incorporated by reference elsewhere herein.

Alternatively, other delivery devices (not shown) may be provided for facilitating delivery of the implant 112, e.g., depending upon the target location for implantation. For example, a catheter, cannula, or other tubular member (not shown) may be provided within which the implant 112 may be loaded, e.g., after manufacturing or immediately before implantation. For example, a suture, tool, and the like (also not shown) may be coupled to one of the outer regions 120 and used to pull the implant 112 into a lumen of a first end of a cannula, the outer regions 120 being resiliently compressed as the implant 112 is pulled therein. As the implant 112 is pulled into the cannula, the implant 112 may also be substantially straightened and/or otherwise elastically deformed. The implant 112 may be deployable from the cannula using a plunger or other pusher device within the cannula, e.g., adjacent the outer region 120 used to pull the implant 112 into the cannula. Alternatively, another suture, tool, and the like may be coupled to the outer region 120 closest to the first end of the cannula and used to pull the implant 112 back out of the cannula, whereupon the outer regions 120 may resiliently expand and/or the implant 112 may be resiliently biased to return towards its relaxed state.

Referring now to FIGS. 4A and 4B, a generally "bowtie" shaped implant 112, such as that shown in FIGS. 2A-2F, may be implanted into an oropharyngeal region of a patient using direct visualization and a curved, e.g., "U" shaped, needle 130 and suture 132. The suture 132 may be tied to or otherwise coupled to either outer region 120 of the implant 112 and/or through the needle 130, e.g., as described in the references incorporated by reference elsewhere herein. Alternatively, the implant 112 (or any of the other embodiments herein) may be implanted using various imaging systems. For example, if at least a portion of the implant 112, e.g., central region 118 and/or tines or other features (not shown), are to be inserted into the ligament ALL and/or into a vertebra (not shown), the procedure may be monitored using fluoroscopy, ultrasound, or other external imaging. To facilitate such monitoring, optionally, the implant 112 may include one or more markers or other features, for example, radiopaque or echogenic markers, on the central region 118 and/or tines or other features (not shown).

Returning to FIGS. 4A and 4B, during implantation of the implant 112, the needle 130 may be introduced into the posterior wall of the oropharyngeal region and pushed through or behind the anterior longitudinal ligament "ALL" located anterior to the spine (although posterior to the oropharyngeal region), thereby creating a passage or opening. The needle 130 is then pulled out of the tissue along with sufficient length of suture 132 to allow it to be grasped and used to pull the implant 112 through or behind the ligament ALL.

Using the suture 130, a first outer region 120a of the implant 112 is then pulled through the opening through or behind the ligament ALL with the curve of the central region 118 facing in the anterior direction. The first outer region 120a may be manually compressed, or may be resiliently compressed as it is pulled through or behind the ligament. Once the first outer region 120a passes completely through or behind the ligament ALL, the first outer region 120a may resiliently expand towards its relaxed state, as shown in FIG. 4B.

The implant 112 may be self-locating, e.g., in that it is shaped and structured to gently unfold, expand, or otherwise spring into its appropriate position once it has been correctly placed. Alternatively, the user may manipulate the implant 112 to ensure that the central region 118 and sleeve 114 are positioned across the ligament ALL and the outer regions 120 are positioned at least partially around or within the lateral surfaces of the oropharyngeal region. The suture 132 may be cut and removed, leaving the implant 112 in position such that the central region 118 remains within the opening through or behind the ligament ALL. The outer regions 120 may rest against the surface of the mucosal layer of the posterior, lateral, and optionally anterior walls of the oropharyngeal region, e.g., such that the opposite ends of the outer regions 120 rest against the tongue, depending on the length of the outer regions 120.

Optionally, if desired, the implant 112 may subsequently be removed from the patient, e.g., using a similar procedure used for implantation, as disclosed in the applications incorporated by reference elsewhere herein.

Figure 5:
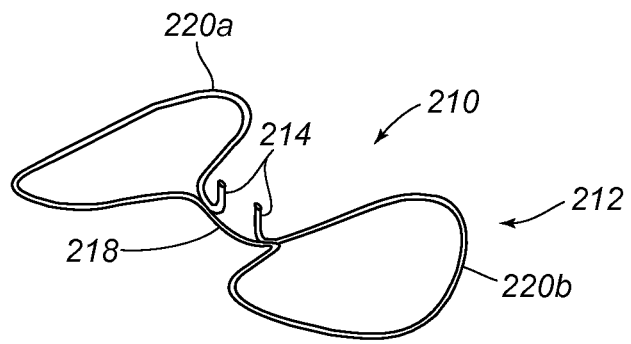
FIG. 5. is a perspective view of yet another embodiment of an implant for treating sleep apnea, snoring, and/or other breathing disorders that includes features for engaging the anterior longitudinal ligament or other tissue structures such as vertebrae.

FIG. 5 shows an alternative embodiment of an apparatus 210 including an implant 212 generally similar to the previous implants. For example, the implant 210 may include a relatively narrow central region 218 between relatively wide outer regions 220. Unlike the previous embodiments, the central region 218 includes one or more features for engaging an anterior longitudinal ligament and/or other tissue structure adjacent an oropharyngeal region or other location within which the implant 212 is introduced for implantation.

For example, as shown, the implant 212 includes a pair of tines 214 extending from the central region 218. The tines 214 may be biased to extend substantially perpendicularly to or otherwise transversely from the central region 218. The tines 214 may be elastically or plastically deformable, e.g., to open the tines 214 to accommodate receiving the tines 214 on either side of the ligament ALL. The tines 214 may then be released to resiliently return inwardly or may be plastically deformed inwardly to engage the ligament ALL, e.g., to enhance securely fixing the implant 212 within an oropharyngeal region.

Alternatively, the tines 214 may be substantially rigid, e.g., such that the tines 214 may be penetrated into the ligament ALL and/or other tissue adjacent the oropharyngeal region within which the implant 212 is introduced. For example, in an alternative embodiment, the tines 213 may be sufficiently rigid and long to extend through adjacent soft tissue and penetrate a vertebra adjacent the oropharyngeal region. Such rigid tines 214 may reduce the risk of migration of the implant 212 after implantation.

Figure 9:
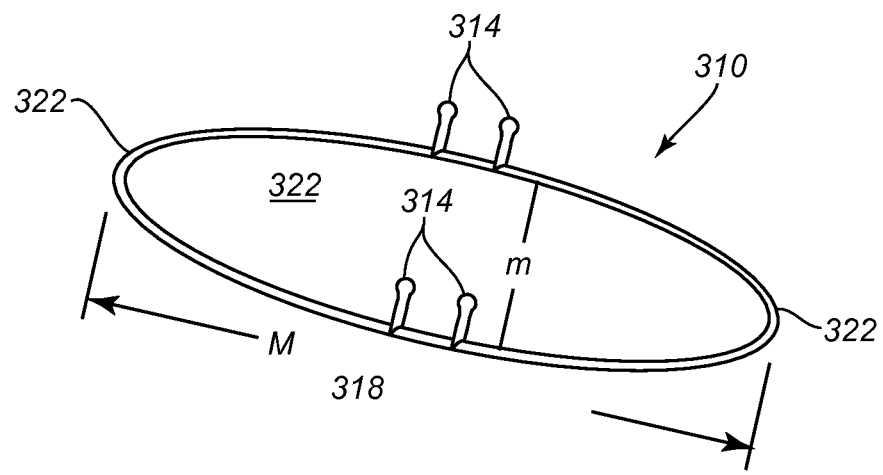
FIG. 9 is a perspective view of still another embodiment of an implant for treating sleep apnea, snoring, and/or other breathing disorders that includes features for engaging the anterior longitudinal ligament or other tissue structures such as vertebrae.
Figure 9A:
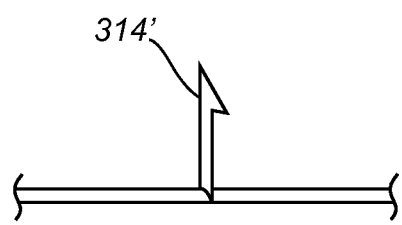
FIG. 9A is a detail of an alternative embodiment of a tine that may be provided on an implant, such as the implants of FIGS. 5 and 9.

The tines 214 may include sharpened and/or pointed tips (not shown) to facilitate penetration and/or may include barbs, threads, or other features, e.g., similar to those shown in FIG. 9A, that may resist removal once the tines 214 are introduced into tissue, e.g., to enhance anchoring and resist migration of the implant 112.

In a further alternative, multiple sets of tines 214 or other penetrating or engaging features (not shown) may be provided. For example, if the implant includes a pair of spaced apart elements in the relatively narrow central region (e.g., as disclosed in the references incorporated by reference elsewhere herein), a set of tines may be provided on each spaced apart element, which may be used to engage the ligament ALL and/or penetrate into tissue adjacent the oropharyngeal region.

Figure 6A:
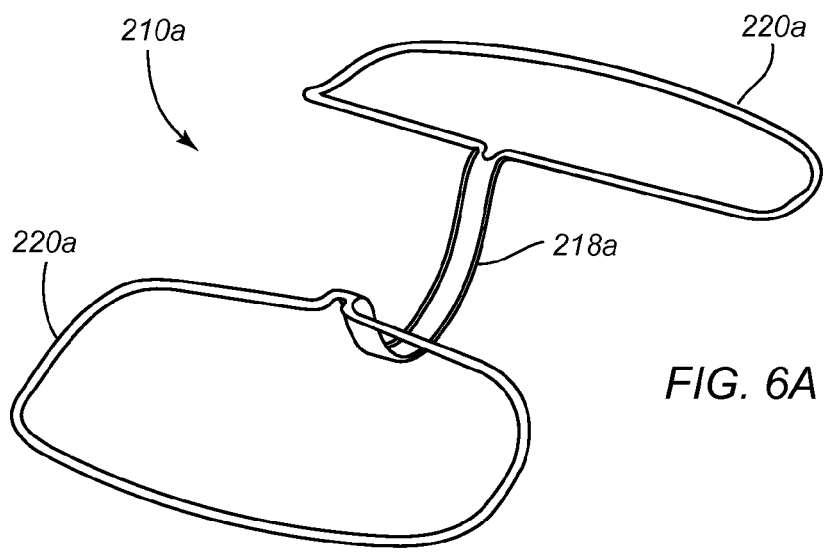
FIGS. 6A-6C are perspective, front, and top views, respectively, of still another embodiment of an implant for treating sleep apnea, snoring, and/or other breathing disorders.
Figure 6B:
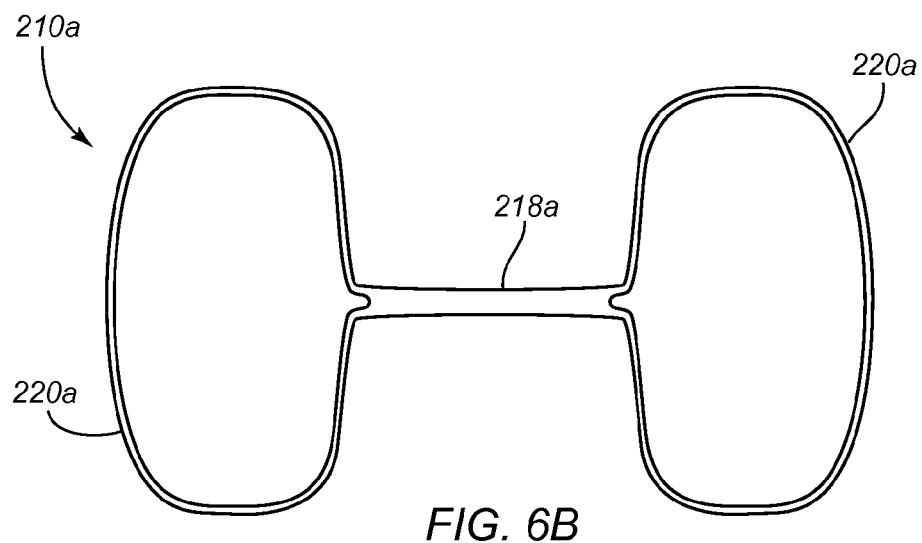
Figure 6C:
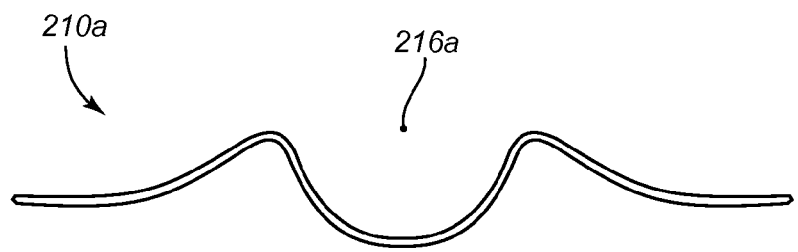
Figure 7A:
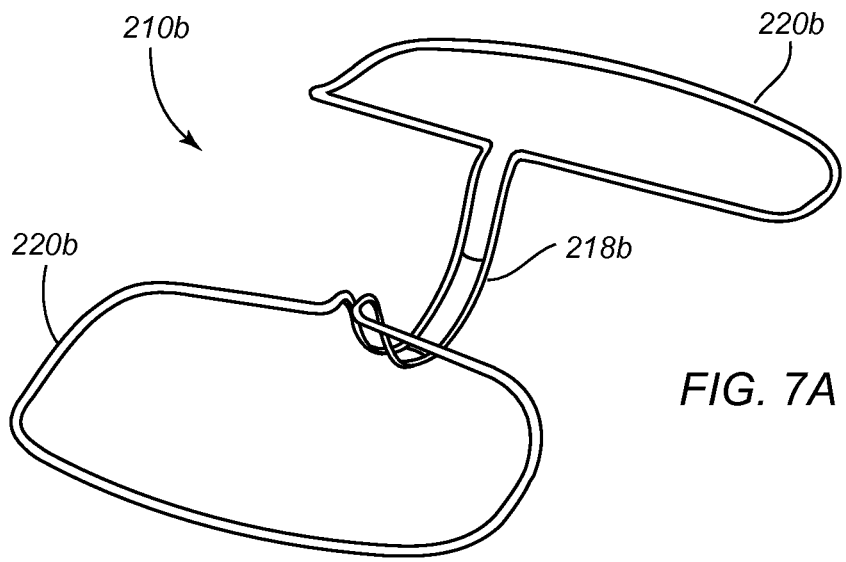
FIGS. 7A-7C are perspective, front, and top views, respectively, of yet another embodiment of an implant for treating sleep apnea, snoring, and/or other breathing disorders.
Figure 7B:
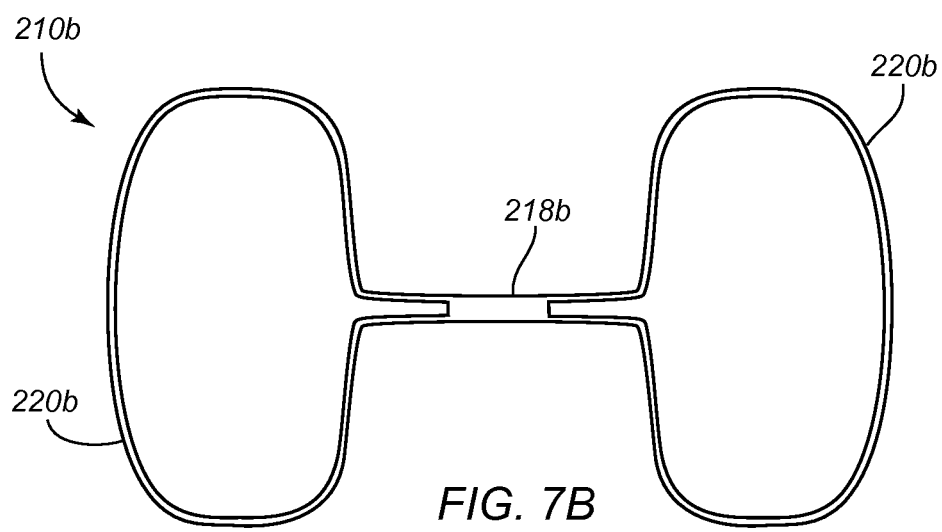
Figure 7C:
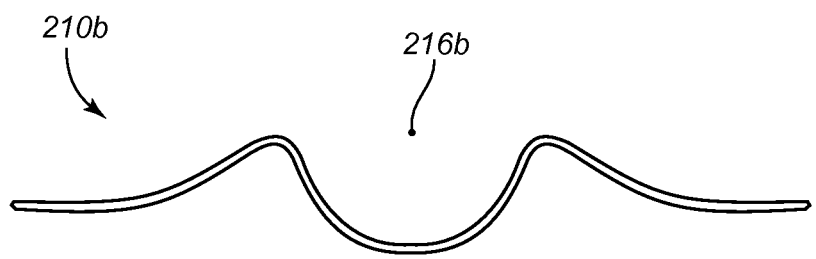
Figure 8A:
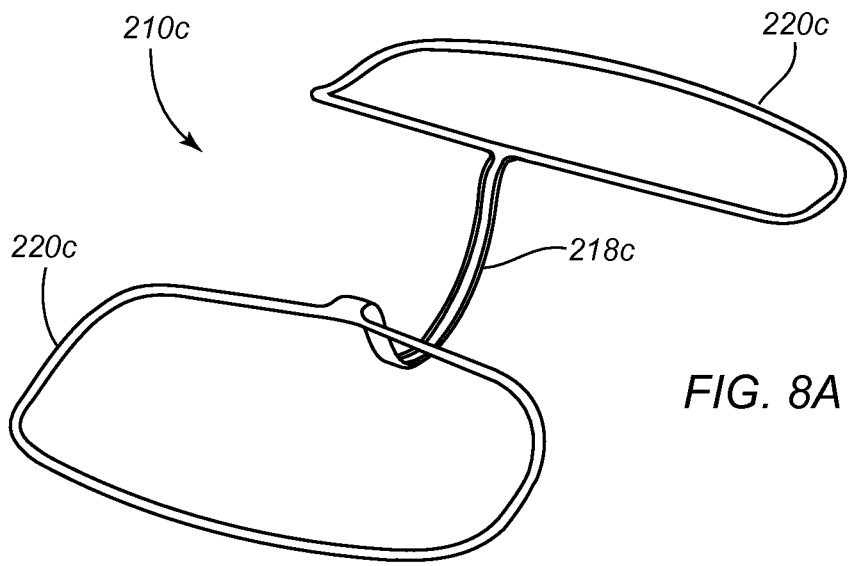
FIGS. 8A-8C are perspective, front, and top views, respectively, of still another embodiment of an implant for treating sleep apnea, snoring, and/or other breathing disorders.
Figure 8B:
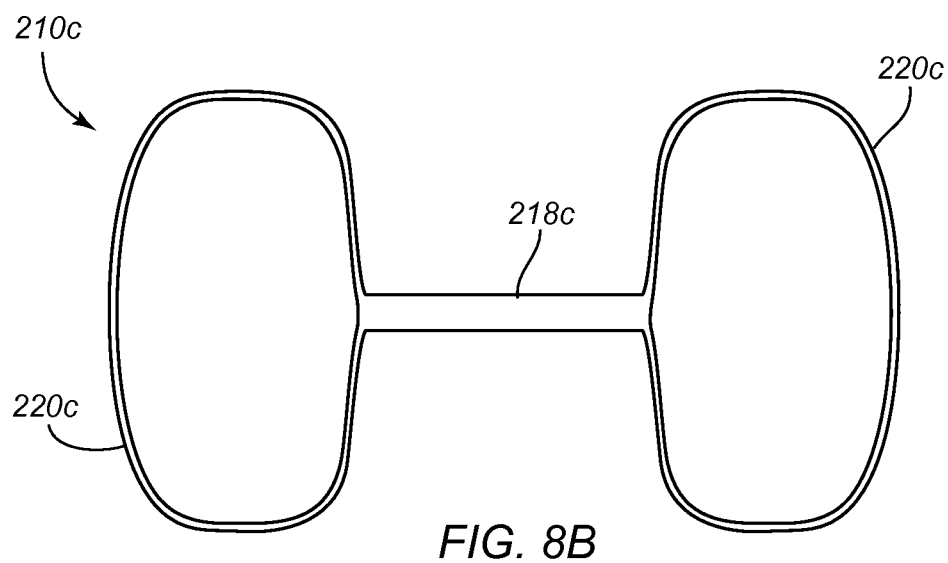
Figure 8C:
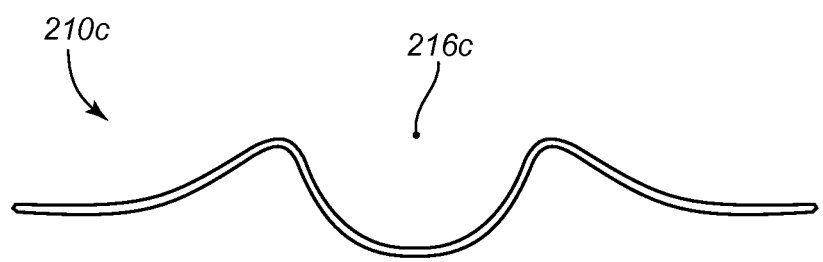

Turning to FIGS. 6A-8C, additional alternative embodiments of implants 210a-210c are shown that include relatively narrow central regions 218a-218c between relatively wide outer regions 220a-220c, generally similar to the previous embodiments. Unlike the previous embodiments, the implants 210a-210c have a different cross-section orthogonal to vertical axis 216a-216c, as best seen in FIGS. 6C, 7C, and 8C. In each of these embodiments, the outer regions 220a-220c generally lie within a plane, except that, as they transition inwardly towards the central region 218a-218c, they may rise above the plane. The central region 218a-218c defines a curved shape, e.g., defining a portion of a circle or ellipse that extends in a direction to intersect and descend below the plan, i.e., curve in an opposite direction to the outer regions 220a-220c.

In this configuration, the central region 218a-218c may be shaped to be introduced behind or through the ligament ALL, e.g., as described above with reference to FIGS. 4A and 4B). When the central region 218a-218c is introduced behind or through the ligament ALL, the outer regions 220a-220c may be biased to a substantially planar configuration, but may adopt the curvature of the posterior and lateral walls of an oropharyngeal region (not shown) within which the implant 210a-210c is being implanted, e.g., to adopt a "C" shape. In this manner, the outer regions 220a-220c may exert an outward force or otherwise treat the oropharyngeal region, similar to other embodiments described herein and in the applications incorporated by reference herein. Alternatively, these implants 210a-210c may be provided in a substantially planar configuration, and may be folded, rolled, or otherwise directed to a curved configuration for implantation within the oropharyngeal region, e.g., with the central region 218a-218c secured against the posterior wall of the oropharyngeal region. For example, the central region 218a-218c may include one or more apertures (not shown), similar to the embodiments shown in FIGS. 26-27, which may receive corresponding fasteners (also not shown) to secure the implants 210a-210c to the posterior wall and/or underlying structures, as described elsewhere herein.

The implants 210a-210c may be formed from a substantially flat sheet (not shown), e.g., from which the central region 218a-218c and outer regions 220a-220c may be laser cut, machined, etched, or otherwise formed, similar to other embodiments herein. The shape of the implants 210a-210c relative to the vertical axis 216a-216c may be programmed or otherwise set into the implant 210a-210c after being formed or into the sheet before forming, as desired.

Also unlike the previous embodiments, the implants 210a-210c have different configurations for the central region 218a-218c. For example, the implant 210a shown in FIGS. 6A-6C may include a central region 218a that includes a relatively wide band that curves around the vertical axis 216a and extends between ends of the wire elements defining the outer regions 220a. As shown, a rounded transition may be provided between the ends of the wide band of the central region 218a and the wire elements of the outer regions 220a.

Alternatively, as shown in FIGS. 7A-7C, the central region 218b may include a relatively wide band that extends only partially between the outer regions 220b. In this alternative, the wire elements defining the outer regions 220b curve and extend substantially parallel to one another to partially define the central region 218b. Thus, in this alternative, the implant 210b may provide greater flexibility between the outer regions 220b and the central region 218b, e.g., to facilitate vertical compression and/or folding, rolling, or other displacement of the implant 210b.

In the further alternative shown in FIGS. 8A-8C, the central region 218c includes a relatively wide band that has a smaller vertical height than the central region 218a of the implant 210a shown in FIGS. 6A-6C. Thus, the central region 218c may also have greater flexibility than the central region 218a.

Turning to FIG. 9, another embodiment of an implant 310 is shown that includes an elongate elliptical or other oval or oblong shaped body defining a length or major axis "M" between first and second ends (or outer regions) 322 and a width or minor axis "m," e.g., at a central region 318 between the first and second ends 322. In an exemplary embodiment, the implant 310 may be formed from a wire or sheet, which may be formed into the oval shape, similar to other embodiments herein. In a relaxed state, the implant 310 may be substantially planar, as shown, or alternatively, may have a curved shape, e.g., a "C" shape between the ends 322, similar to other embodiments herein and in the references incorporated by reference herein. The implant 310 may include an open area 322 surrounded by the wire or other material extending around a periphery of the implant 310. Optionally, the open area 322 may include a flexible material, a mesh, supports, and the like (not shown), e.g., to support outer regions 322 of the implant 310 and/or enhance surface contact with adjacent tissue.

As shown, the implant 310 includes two pairs of tines 314 disposed opposite one another, e.g., at the center of the central region 318. Similar to the previous embodiment, the tines 314 may be biased to extend substantially perpendicularly or otherwise transversely from the central region 318, e.g., out of the plane defined by the implant 310. The tines 314 may be elastically or plastically deformable, e.g., to open the tines 314 to accommodate receiving the tines 314 on either side of the ligament ALL. The tines 314 may then be released to resiliently return inwardly or may be plastically deformed inwardly to engage the ligament ALL, e.g., to enhance securely fixing the implant 312 within an oropharyngeal region.

Alternatively, the tines 314 may be substantially rigid, e.g., such that the tines 314 may be penetrated into the ligament ALL, a vertebra, and/or other tissue adjacent the oropharyngeal region within which the implant 310 is introduced. Optionally, in this alternative, the tines 314 may include sharpened tips, barbs, threads, and/or other features, e.g., to facilitate penetration into tissue and/or resist withdrawal once penetrated into tissue.

In a further alternative, shown in FIG. 9A, a single tine 314' may be provided instead of a pair of tines, e.g., on implants 310 or 212. The tine 314' may be penetrated into the ligament ALL, a vertebra (not shown), or other tissue structure, with the barb securing the tine 314' and, consequently, the implant relative to the tissue structure.

In further alternatives, other features may be provided on the implant 310 (or any other embodiments herein or in the references incorporated by reference herein) for securing the implant 310 relative to the ligament ALL or other tissue structures. For example, connectors may be attached to or implanted into tissue within an oropharyngeal region or other target site where an implant is to be introduced. The implant may include mating connectors that may engage the previously implanted connectors when the implant is deployed within the target site. Exemplary connectors may include magnetic connectors, male-female receptacles, and the like (not shown). Alternatively, sutures or other separate fasteners (not shown) may be used to secure an implant within a target site.

It will be appreciated that tines or other features may be provided on any of the implants, stents, or other apparatus disclosed in the references incorporated by reference elsewhere herein, e.g., to reduce the risk of migration and/or otherwise enhance stabilization of the apparatus after implantation. For example, features may be provided adjacent the ends or outer regions of the implant that may be penetrated into tissue to stabilize the ends.

Turning to FIGS. 10A-12C, another embodiment of an implant 310a is shown that includes a central region 318a between outer regions 320a, generally similar to previous embodiments. The outer regions 320a may define a length of the implant 310a, e.g., the distance between the opposite ends of the outer regions 320a, and/or may define a height of the implant 310a, e.g., the distance between lateral sides of the outer regions 320a. In exemplary embodiments, the length may be between about ten and one hundred millimeters (10-100 mm), or between about twenty and fifty millimeters (20-50 mm), and the height may be between about ten and one hundred millimeters (10-100 mm), or between ten and thirty millimeters (10-30 mm). Thus, the implant 310a may have an overall profile (width-to-height relationship) that may range from generally rectangular, elliptical, or oblong to square or circular.

As best seen in FIGS. 10A, 11A, and 12A, the central region 318a may be narrow relative to the outer regions 320a. Similar to other embodiments, the implant 310a may have a generally "bow-tie" shape with the outer regions 320a including lobes defined by struts surrounding and enclosing an open interior space 322a. The outer regions 320a may have a generally rectangular shape, as shown, e.g., including outer segments 344a extending between upper and lower segments 346a and connector segments 348a extending between the upper and lower segments 346a and the central region 318a. The segments 344a-348a may be substantially straight (e.g., as shown for segments 346a, 348a) or may be curved (e.g., as shown for segments 344a), and the bends between adjacent segments 344-348a may be rounded, as shown, or may be blunt (not shown), if desired.

As best seen in FIGS. 10A, 11A, and 12A, the central region 318a may include a pair of struts or elements 332a extending along the length of the implant 310a at least partially between the outer regions 320a. The struts 332a may be spaced apart from one another and coupled together by lateral struts 334a, e.g., surrounding a central opening 335, and may include flanges, rings, or other optional features 336a to facilitate manipulation of the implant 310a, e.g., using a tool 350, as described further below. The struts 332a, 334a may have a width substantially greater than their thickness, which may be the same as the thickness of rest of the implant 310a if the implant 310a has a substantially uniform thickness, e.g., to support the implant 310a within the plane of the implant 310a while allowing displacement out of the plane. Optionally, the struts 332a, 334a may also have a width greater than the width of the segments 344a-348a, e.g., such that the central region 318 has a greater rigidity than the outer regions 320a. However, the struts 332a may accommodate bending, rolling, folding, displacement, or other manipulation of the implant 310a out of the plane, e.g., between a substantially flat configuration, as shown in FIGS. 10A-11C, and a curved configuration, as shown in FIG. 12A-12C, and described further below.

In addition, the implant 310a may include one or more tines, struts, barbed portions, threads, or other elements to enhance securing or anchoring the implant 310 to tissue, e.g., to an anterior longitudinal ligament ("ALL") or other tissue within an oropharyngeal region (not shown). For example, as shown in FIGS. 10A and 10C, the struts 332a in the central region 318a may include extensions 338a that extend into the open interior spaces 322a of the outer regions 320a. The extensions 338a may be curved, as shown in FIGS. 11A-11C, out of the plane defined by the implant 310a, e.g., such that opposing extensions are curved, bent, or otherwise deformed back towards one another to define opposing pairs of tines 338a. As shown, the implant 310a includes two pairs of opposing tines 338a, although it will be appreciated that fewer or more tines (not shown) may be provided, if desired.

In an exemplary method for making the implant 310a, a flat sheet of material, e.g., Nitinol or other elastic or superelastic material, may be provided having a length and height at least as large as the implant 310a to be formed therefrom. Alternatively, other elastic materials may be provided for the implant 310a, e.g., stainless steel, Elgiloy, titanium or other metals, polymers, or composite materials. Regions of the sheet may be removed, e.g., by laser-cutting, machining, etching, stamping, and the like, to create the various features of the implant 310a, e.g., the struts 332a, 334, tines 338a, and segments 344a-348a, as shown in FIGS. 10A-10C.

The tines 338a may then be plastically deformed and/or heat set into the curved shape shown in FIGS. 11A-11C. For example, the flat implant 310a may be mounted in a fixture, and the tines 338a may be folded, curved, or otherwise directed around a mandrel into the desired curved shape. The resulting assembly may then be heat treated to set the curved shape into the tines 338a. Thus, the implant 310a may be biased to a substantially flat configuration defining a plane with the tines 338a extending out of that plane and/or partially back towards one another.

During use, the implant 310a may be directed to a curved configuration, e.g., an "L" shaped or "C" shaped configuration, as shown in FIGS. 12A-12C for introduction and/or implantation within an oropharyngeal region or other location within a patient's body (not shown). Once implanted within an oropharyngeal region, the outer regions 320a may be biased to return back towards the substantially flat configuration, thereby exerting a radially outward force on surrounding tissues, similar to other embodiments herein and in the references incorporated by reference herein.

Figure 13A:
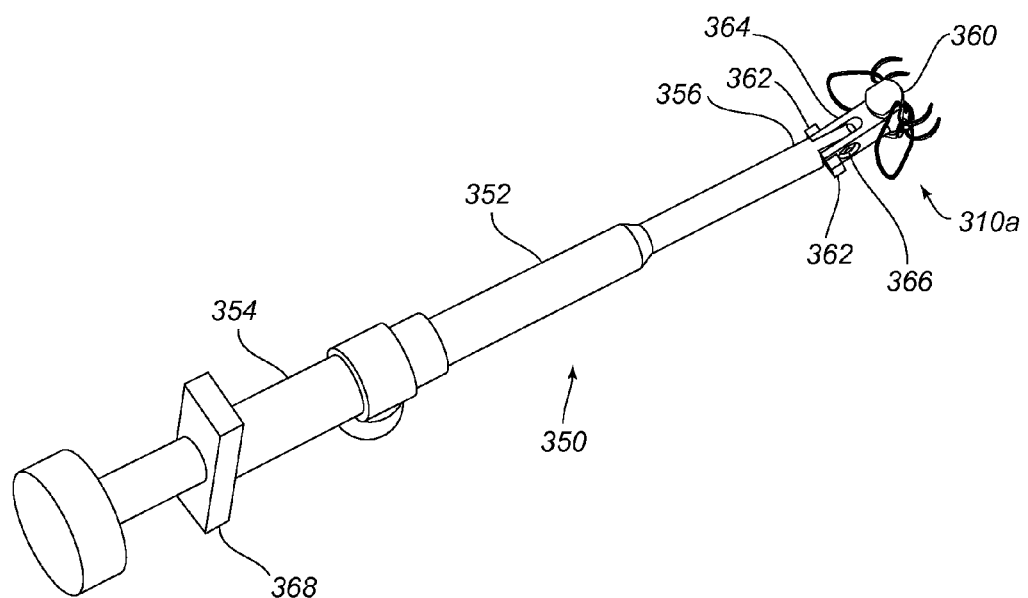
FIG. 13A is a perspective view of a system including a tool for delivering the implant of FIGS. 10A-12C into an oropharyngeal region of a patient.
Figure 13B:
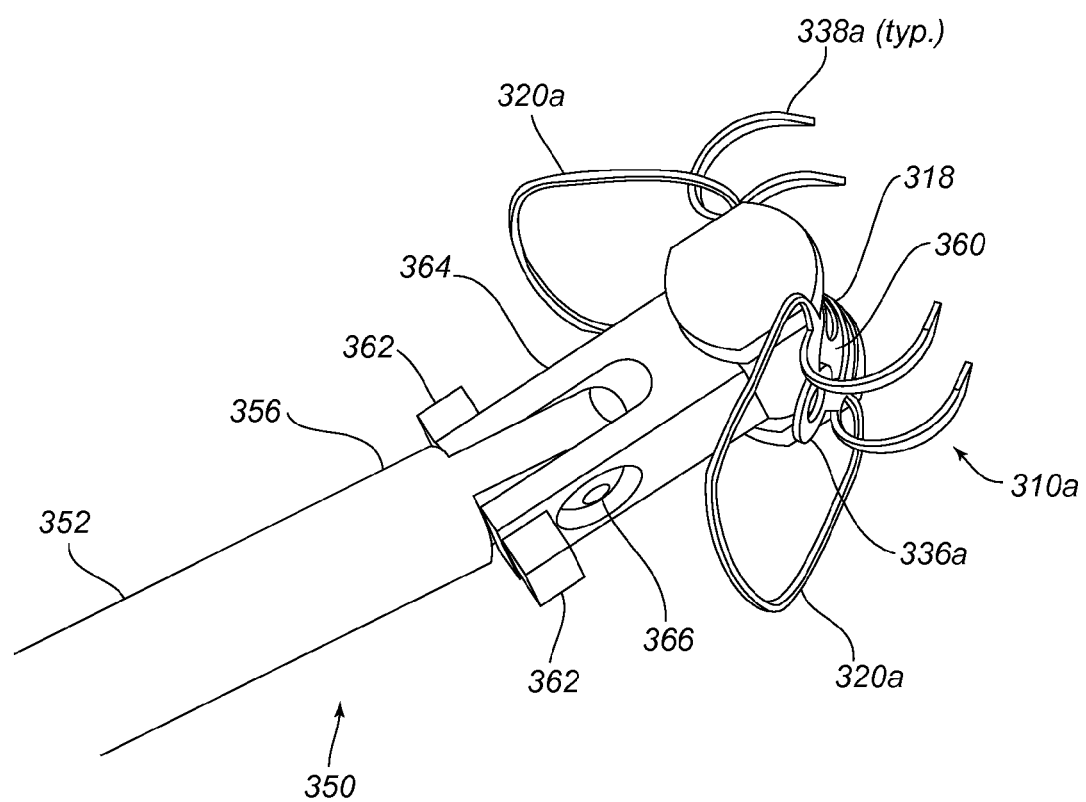
FIGS. 13B and 13C are details of a distal end of the tool of FIG. 13A, showing the implant being directed to a curved configuration for introduction into the oropharyngeal region of a patient.
Figure 13C:
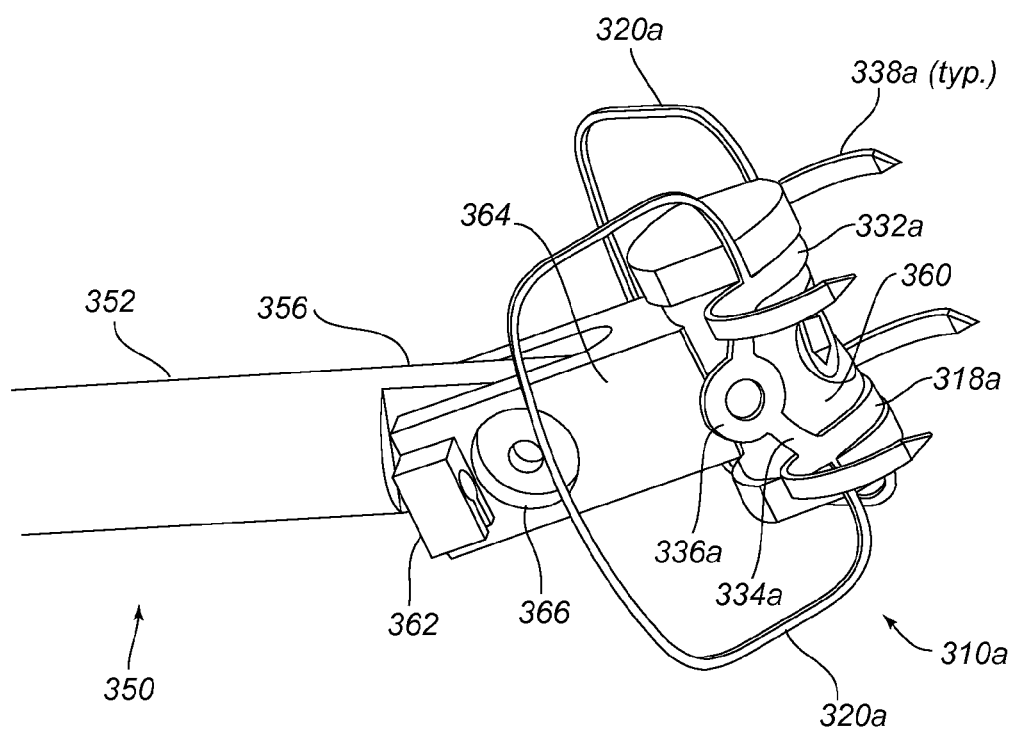

Optionally, a tool may be provided to facilitate directing the implant 310a between the substantially flat and curved configurations and/or otherwise introducing the implant 310a into an oropharyngeal region. FIGS. 13A-13C show an exemplary embodiment of a tool 350 that includes an elongate shaft 352 including a proximal end 354 for manipulating the tool 350 and a distal end 354 sized for carrying an implant, such as implant 310a. The distal end 354 of the tool 350 may be sized for introduction into a patient's body, e.g., through the patient's mouth into the oropharyngeal region, and/or may include one or more features for releasably securing the implant 310a to the tool 350.

For example, in one embodiment, best seen in FIGS. 13B and 13C, the distal end 356 may include a rounded tip or knuckle 360 against which the central region 318a of the implant 310a may be placed and/or secured. The rounded tip 360 may have a radius of curvature corresponding to a desired radius of curvature for the central region 318a when the implant 310a is directed from the substantially flat to the curved configuration.

The distal end 356 may also include one or more features for engaging the implant 310a, e.g., the rings 336a on the lateral struts 334a, to secure the implant 310a to the distal end 356, e.g., in the curved configuration. For example, one or more filaments or rods (not shown) may be directed through the rings 336a and secured to the distal end 356 of the tool 350, e.g., to posts 362 proximal to the distal tip 356. In one embodiment, one or more rods may be directed through each ring 336a, and through an aperture in the corresponding post 362, and the rod(s) may be retracted to cause the implant 310a to deflect into the curved configuration. Alternatively, a single filament may be directed through both rings 336a and posts 362, which may be tightened to secure the implant 310a in the curved configuration.

It will be appreciated that, as the implant 310 is directed from the substantially flat configuration to the curved configuration, the opposing pairs of tines 338a may be directed away from one another to open a space therebetween, as best seen in FIGS. 11B, 11C, 12B, and 12C.

Ends of the rod(s) or filament(s) may be fixed relative to the posts 362 to prevent the rods from releasing the implant 310a. When it is desired to release the implant 310a from the tool 350, e.g., after introduction into the oropharyngeal region of a patient, the rods may be used to drive the tines into the tissue then released from the rings 336a and removed.

Alternatively, the distal end 356 of the tool 350 may include other actuatable features that may be engaged with the rings 336a and/or otherwise with the implant 310a. For example, a pair of hooks (not shown) may be provided adjacent the distal tip 360 that may be movable between two or more positions for releasably securing the implant 310a and/or directing the implant 310a between the substantially flat and curved configurations. The hooks may have a relatively low profile and/or substantially atraumatic tips to allow engagement with the rings 336a while minimizing contact with surrounding tissue during introduction of the implant 310a into a patient's body.

In a first or distal position, the hooks may be disposed adjacent the distal tip 360 and spaced apart such that the hooks may be received in respective rings. The hooks may then be directed to a second intermediate position, e.g., directing the hooks outwardly away from one another and/or proximally, to secure the inner region 318a of the implant 310a against the distal tip 360 with the implant 310a still in the substantially flat configuration (or slightly curved, if it is desired to maintain a slight tension on the implant 310a). When desired, the hooks may be directed to a third proximal position, wherein the rings 336a are pulled proximally and/or wound around the distal tip 360 to direct the implant 310a to the curved configuration. Alternatively, the hooks may actuated directly between the first and third positions, if desired.

Also when desired, the hooks may be directed back to the second and/or first positions to release the implant 310a, e.g., within an oropharyngeal region. For example, the implant 310a, carried on the distal end 356 of the tool 350 in the curved configuration, may be introduced through a patient's mouth into the oropharyngeal region. With the tines 338a oriented towards the posterior wall of the oropharyngeal region, the implant 310a may be at least partially released, e.g., by directing the hooks to the second or first position, to drive the tines 338a into tissue adjacent the posterior wall, e.g., into or behind the ligament ALL, similar to other embodiments. For example, as the implant 310a is partially released, the implant 310a may resiliently attempt to return towards the substantially flat configuration, thereby directing the opposing tines 338 back towards one another, penetrating and/or otherwise capturing tissue therebetween.

Alternatively, the tines 338a may be driven into tissue with the implant 310a maintained in the curved configuration. For example, the implant 310a may be held in the curved configuration by the hooks, and the tool 350 may be advanced to forcefully drive the tines 338a into the tissue. Once the tines 338a are sufficiently advanced into tissue, the tool 350 may be directed to the second or first positions, thereby releasing the implant 310a towards the flat configuration and, optionally, further driving the tines 338a into the tissue and directing the outer regions 320a against the lateral and/or anterior walls of the oropharyngeal region. The implant 310a may then be fully released, and the tool 350 removed.

Optionally, the proximal end 354 may include one or more actuators (not shown) for controlling the features of the distal end 356, e.g., to direct the implant 310a between the substantially flat and curved configurations and/or to release the implant 310a from the distal end 356. For example, if the tool 350 includes hooks, a trigger or slider (not shown) may be provided on the proximal end 354 that is mechanically coupled to the hooks for directing the hooks between the first and third positions.

Optionally, the tool 350 may include one or more features for changing an orientation of the distal end 356. For example, as best seen in FIGS. 13B and 13C, the distal end 356 may include a bendable portion 364 that may be selectively directed to one or more angles relative to a longitudinal axis of the shaft 352. For example, the bendable portion 364 may be a substantially rigid segment coupled to the shaft 352 by a hinge or other pivot point 366. An actuator, e.g., slider 368, may be provided on the proximal end 354 that is mechanically coupled to the bendable portion 364. The slider 368 may be directable between a first or distal position in which the bendable portion 364 is substantially coaxial with the longitudinal axis of the shaft 352, e.g., such that the tool 350 is substantially straight, and a second or proximal position in which the bendable portion 364 is rotated to a maximum bend angle, e.g., less than ninety degrees (90°) relative to the longitudinal axis of the shaft 352. The slider 368 may be directable to any location between the first and second positions, e.g. to orient that implant 310a at any desired angle relative to the shaft 352, which may facilitate introduction and/or orientation of the implant 310 relative to the oropharyngeal region of the patient.

Alternatively, other features may be provided to allow adjustment of the orientation of the implant 310a relative to the shaft 352. For example, the distal end 356 may be malleable such that the user may deform the distal end 356 to a desired orientation, which the distal end 356 will maintain until otherwise deformed. In a further alternative, the distal end 356 may be semi-rigid or flexible and the tool 350 may include one or more steering cables (not shown) within the shaft 352 that may actuated to direct the distal end 356 into a desired shape, e.g., a simple curve or a more complicated multiple curved shape, if desired.

Figure 19A:
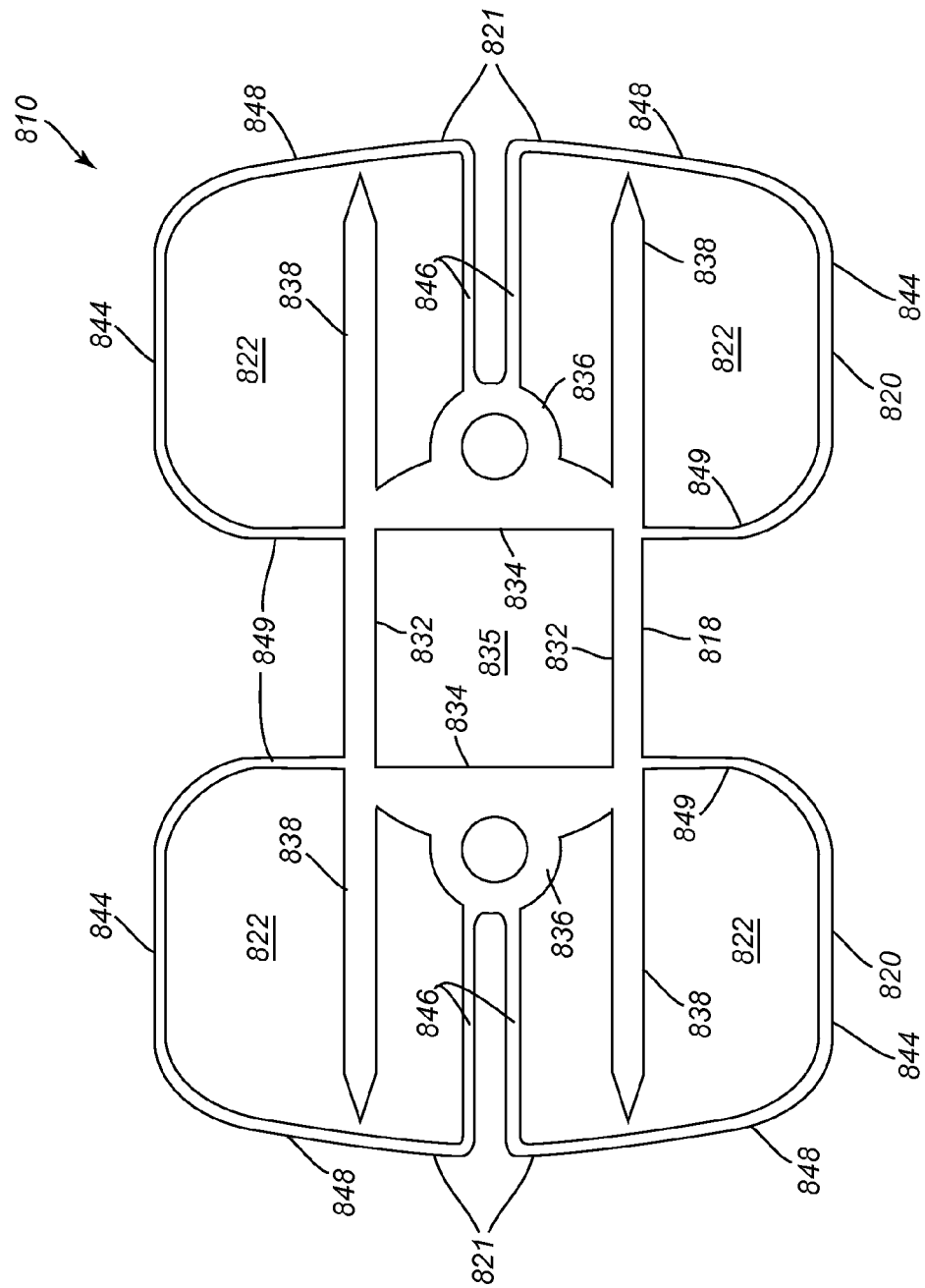
FIGS. 19A-19C are top views of another embodiment of an implant, showing the implant as formed from a flat sheet (FIG. 19A), in its heat-shaped relaxed state (FIG. 19B), and in a cocked state to facilitate implantation (FIG. 19C).
Figure 19B:
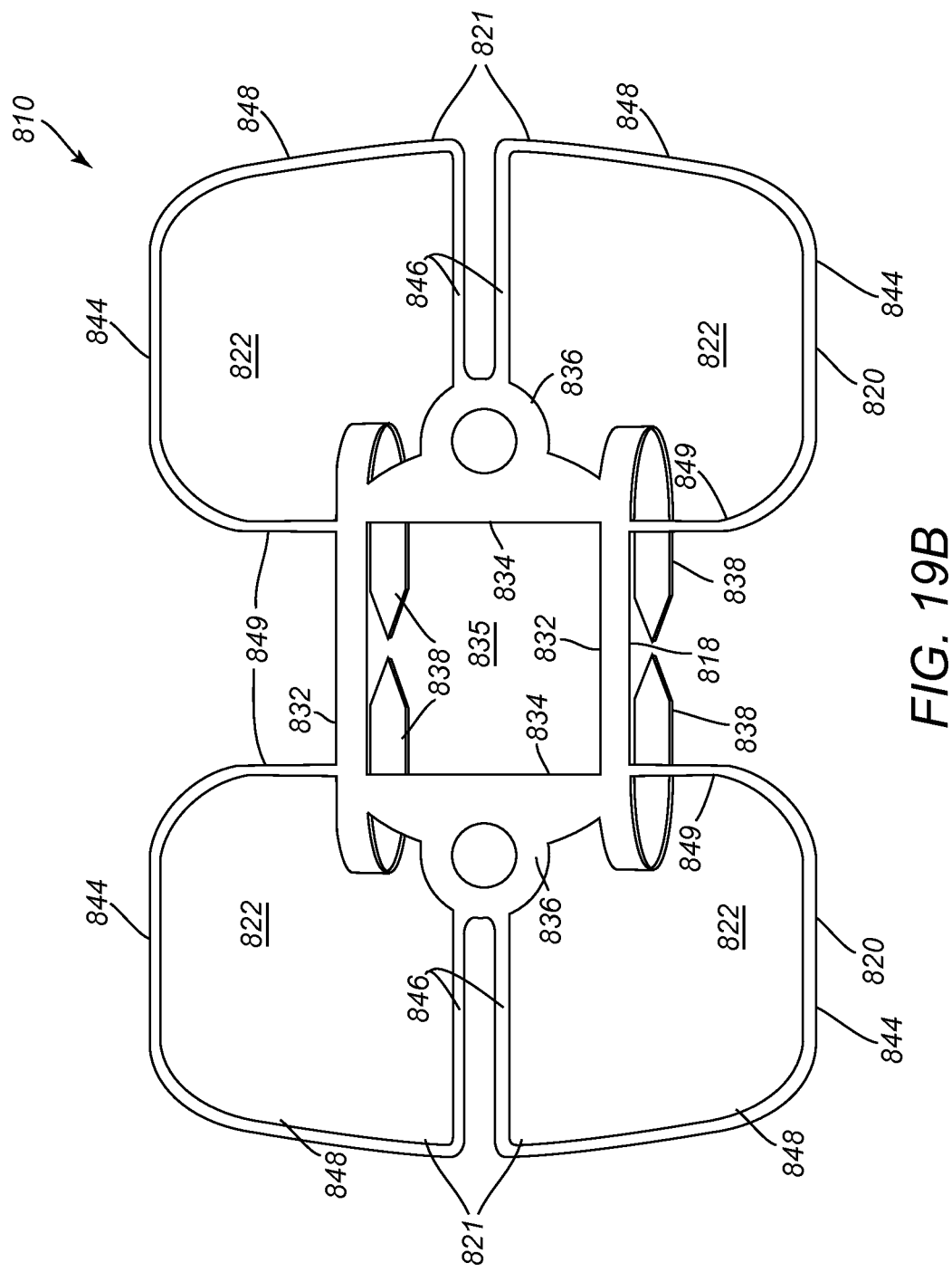
Figure 19C:
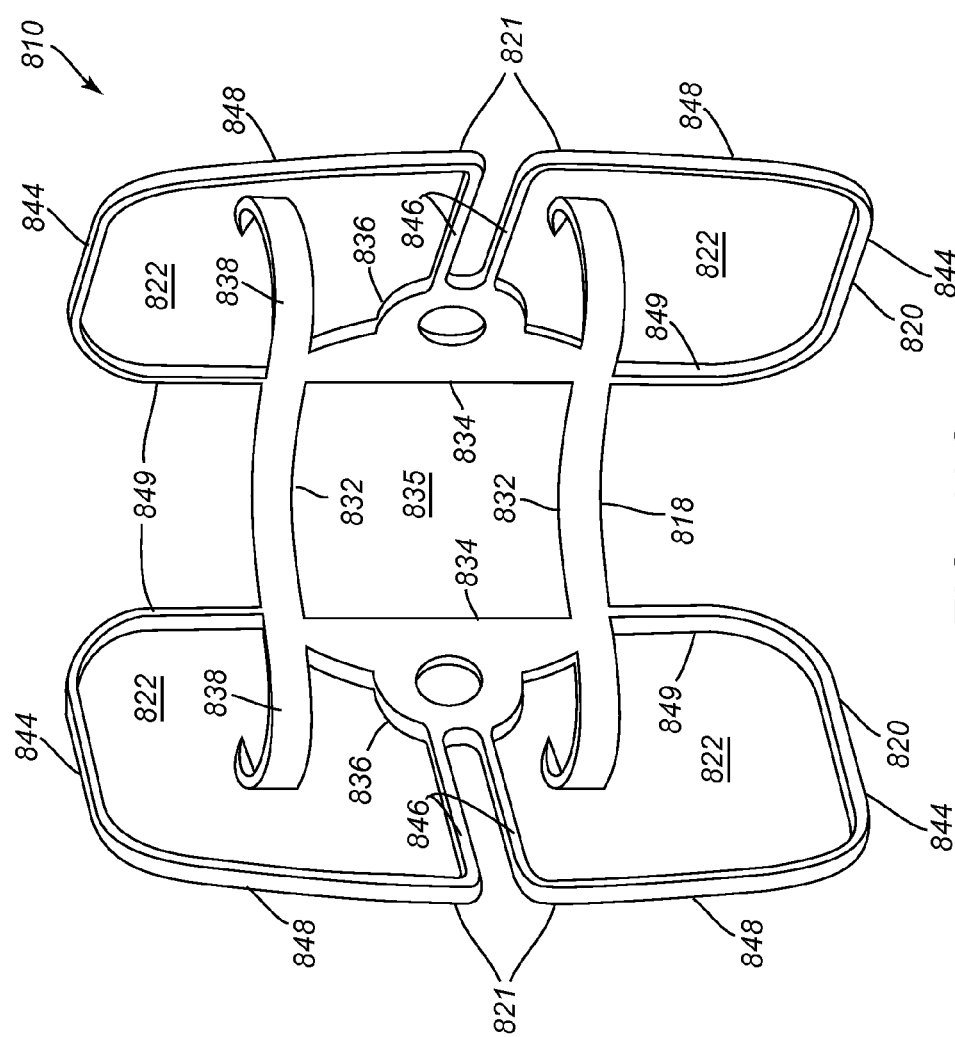

Turning to FIGS. 19A-19C, another embodiment of an implant 810 is shown that includes a central region 818 between outer regions 820, generally similar to previous embodiments. The outer regions 820 may define a length of the implant 810, e.g., the distance between the opposite ends of the outer regions 820, and/or may define a height of the implant 810, e.g., the distance between lateral sides of the outer regions 820, also similar to previous embodiments.

As shown, the central region 818 may be narrow relative to the outer regions 820. Similar to other embodiments, the implant 810 may have a generally "bow-tie" or "'butterfly" shape with the outer regions 820 including lobes defined by struts surrounding an enclosing an open interior space 822. Unlike the previous embodiments, each of the outer regions 820 includes a pair of flanges or lobes 821, i.e., an upper flange or lobe and a lower flange or lobe, that are movable at least partially independently from one another. For example, as shown, each flange or lobe 821 may include generally horizontal outer and inner segments 844, 846 extending between generally vertical end segments 848, 849 and connector segments 849 extending between the outer and inner segments 844, 846 and the central region 818, thereby defining the open interior space 822. The segments 844-849 may be substantially straight and/or curved, and the bends between adjacent segments 844-849 may be rounded, as shown, or may be blunt (not shown), if desired.

As shown, the central region 818 may include a pair of struts or elements 832 extending lengthwise along the implant 810 between the outer regions 820. The struts 832 may be spaced apart from one another and coupled together by lateral struts 834, which may include flanges, rings, or other optional features 836 to facilitate manipulation of the implant 810, e.g., using a tool (not shown), similar to previous embodiments. The struts 832, 834 may have a width substantially greater than their thickness (which may be the same as the thickness of the rest of the implant 810 if the implant 810 has a substantially uniform thickness). Optionally, the struts 832, 834 may also have a width greater than the width of the segments 844-849, e.g., such that the central region 318 has a greater rigidity than the outer regions 320a. However, the struts 832 may accommodate bending, rolling, folding, displacement, or other manipulation of the implant 810, e.g., between a substantially flat configuration, as shown in FIG. 19A, and a curved configuration, as shown in FIG. 19C, and described further below.

In addition, the implant 810 may include one or more tines, struts, barbed portions, threads, or other elements to enhance securing or anchoring the implant 310 to tissue, e.g., to an anterior longitudinal ligament ("ALL"), vertebra, or other tissue within an oropharyngeal region (not shown). For example, as shown, the struts 832 in the central region 818 may include tines 838 that extend into the open interior spaces 822 of the outer regions 320a. The tines 838 may be curved, as shown in FIGS. 19B and 19C, out of a plane defined by the implant 810 in a relaxed state, e.g., such that opposing extensions are curved, bent, or otherwise deformed back towards one another to define opposing pairs of tines 838. As shown, the implant 810 includes two pairs of opposing tines 838, although it will be appreciated that fewer or more tines (not shown) may be provided, if desired. Alternatively, the tines may be oriented in other configurations, e.g., substantially perpendicular to the plane of the implant 810 in the relaxed state or away from one another, as described elsewhere herein.

Similar to other embodiments, the implant 810 may be formed from a flat sheet of material, e.g., Nitinol or other elastic or superelastic material, having a length and height at least as large as the implant 810 to be formed therefrom. Regions of the sheet may be removed, e.g., by laser-cutting, machining, etching, and the like, to create the various features of the implant 810. The tines 838 may then be plastically deformed and/or heat set into the curved shape shown in FIGS. 19B and 19C. For example, the flat implant 810 may be mounted in a fixture, and the tines 838 may be folded, curved, or otherwise directed around a mandrel into the desired curved shape. The resulting assembly may then be heat treated to set the curved shape into the tines 838. Thus, the implant 810 may be biased to a substantially flat configuration defining a plane with the tines 838 extending out of that plane and/or partially back towards one another.

During use, the implant 810 may be directed to a curved configuration, e.g., as shown in FIG. 19C, using a tool (not shown), for introduction and/or implantation within an oropharyngeal region or other location within a patient's body (not shown). As the implant 810 is directed from the substantially flat configuration to the curved configuration, the opposing pairs of tines 838 may be directed away from one another to open a space therebetween. The tines 838 may then be penetrated into tissue, e.g., adjacent or through the ligament ALL, vertebra, and/or other tissue adjacent the oropharyngeal region, and the implant 810 may then be released, similar to other embodiments herein.

Once implanted within an oropharyngeal region in the curved configuration, the outer regions 820 may be biased to return back towards the substantially flat configuration, thereby exerting a radially outward force on surrounding tissues, similar to other embodiments herein and in the references incorporated by reference herein. The separate flanges or lobes 821 of each outer region 820 may provide greater apposition with surrounding tissue and/or flexibility, e.g., to enhance dilation of the surrounding tissue while accommodating swallowing or other movement of the tissue.

Figure 20B:
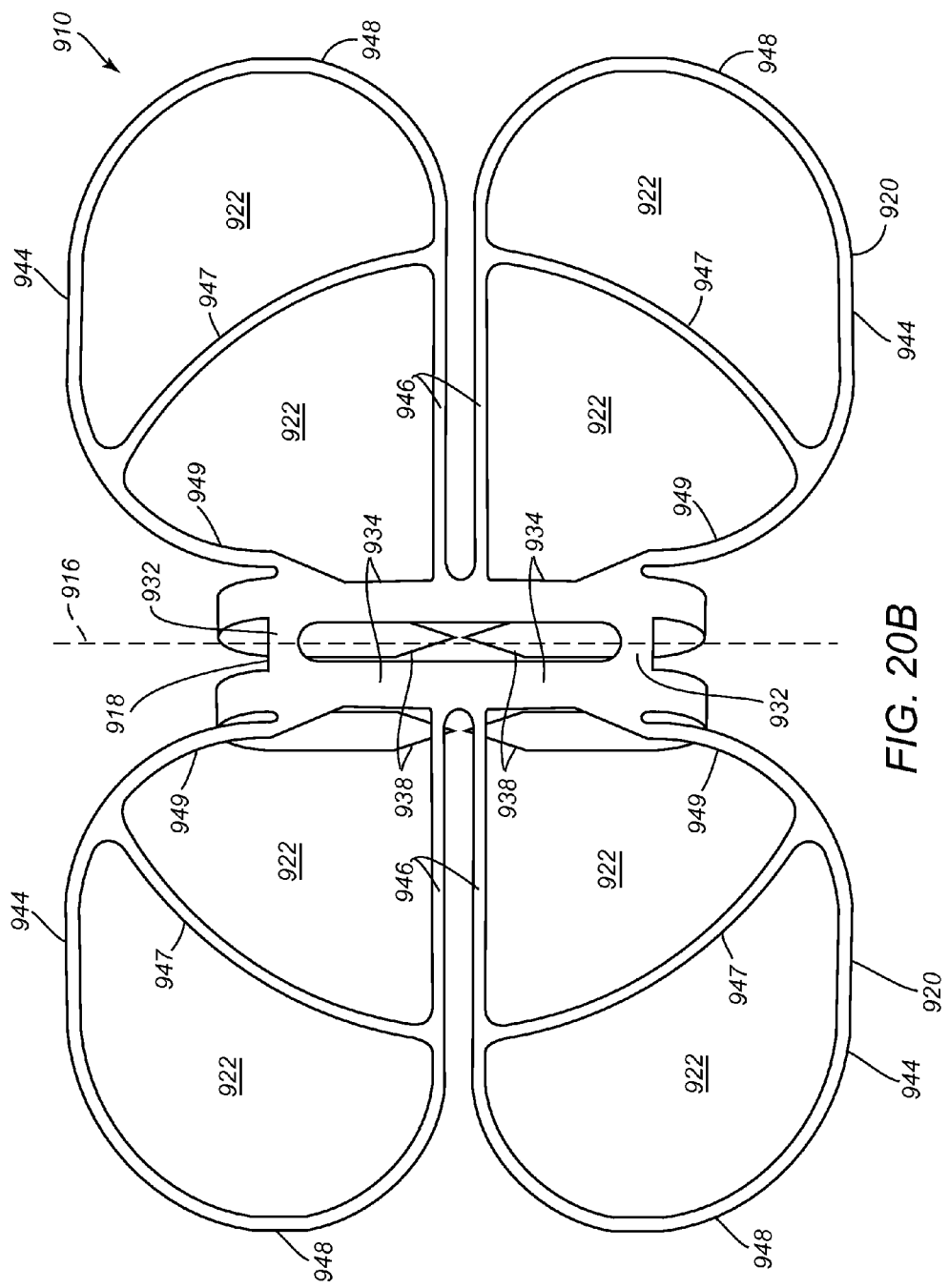
Figure 20C:
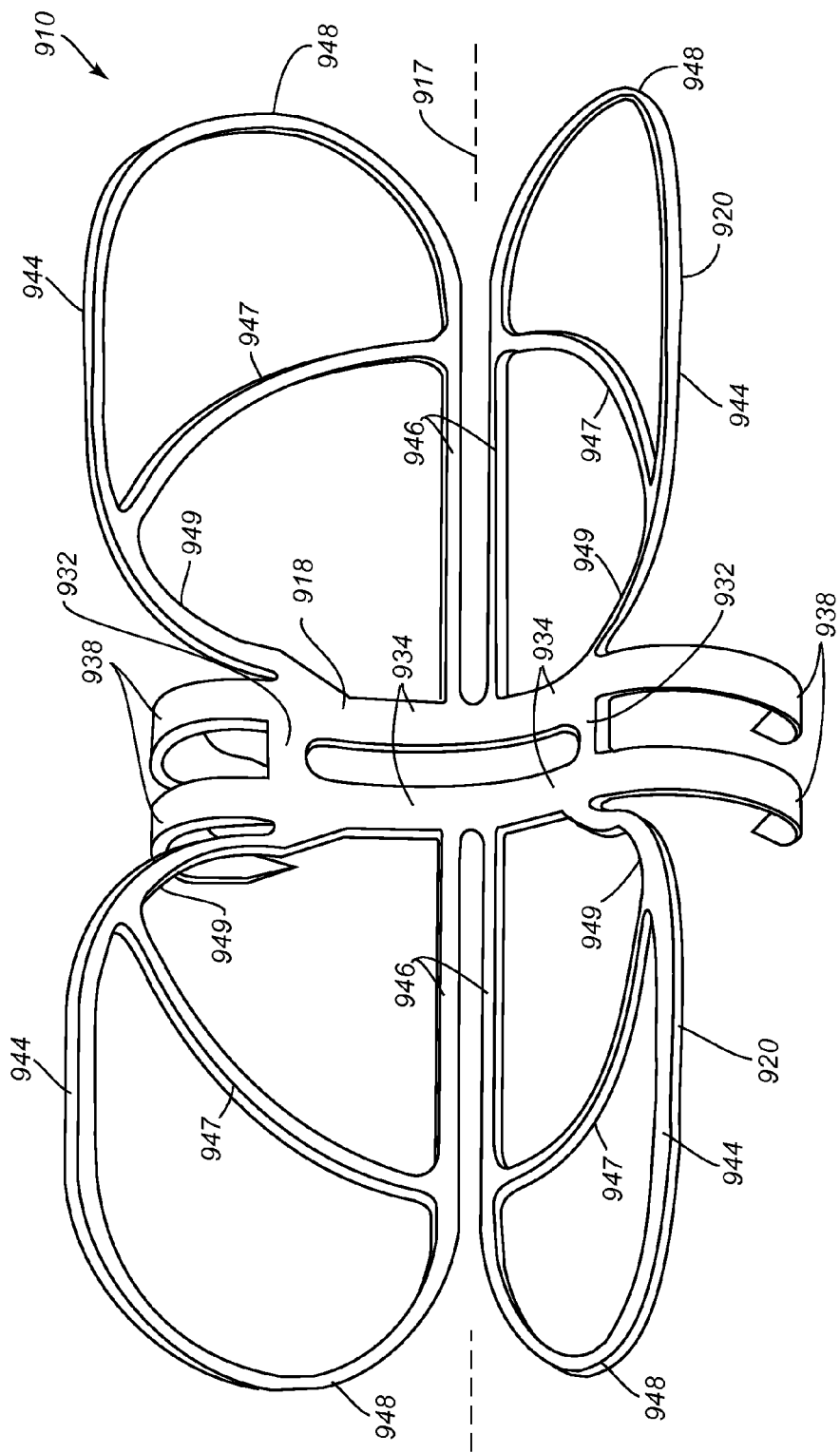

Turning to FIGS. 20A-20C, another embodiment of an implant 910 is shown that includes a relatively narrow central region 918 between outer regions 920 lying generally within a plane to define a substantially flat configuration, generally similar to previous embodiments. Unlike the implant 810, the implant 910 includes tines 938 that extend vertically substantially parallel to its vertical axis 916, i.e., orthogonal to the length or major axis of the implant 910, as shown in FIG. 20A. The tines 938 may be plastically deformed and/or heat set to curve out of the plane of the implant 910 and towards one another, as shown in FIG. 20B, similar to other embodiments herein. Thus, tips of the opposing pairs of tines 938 may be oriented towards one another when the implant 910 is in its relaxed configuration. As shown, opposing tips of the tines 938 are aligned with and spaced apart slightly from one another, although alternatively the tips may be offset from one another and/or may extend between the opposing tines 938 (not shown), if desired.

In addition, each of the outer regions 920 includes a pair of flanges or lobes 921 that may have a greater height than the central region 918, e.g., to provide greater contact area with adjacent tissue when implanted within an oropharyngeal region (not shown). Optionally, as shown, the flanges 921 may include supplemental struts 947 that extend across the open interior spaces 922 of the respective flanges 921. These struts 947 may enhance the stiffness of the flanges 921, while allowing them some independent motion relative to one another, and/or may enhance surface contact with adjacent tissue when the implant 910 is implanted.

During use, the implant 910 may be directed to a curved configuration along the length of the implant 910 or about its horizontal axis 917, e.g., as shown in FIG. 20C, using a tool (not shown) similar to the previous embodiments, for introduction and/or implantation within an oropharyngeal region or other location within a patient's body (not shown). As the implant 910 is directed from the substantially flat configuration to the curved configuration, the opposing pairs of tines 938 may be directed away from one another to open a space therebetween. The tines 938 may be penetrated into tissue, e.g., adjacent or through the ALL, and the implant 910 may then be released.

Turning to FIGS. 21A-21D, another embodiment of an implant 1010 is shown that includes a relatively narrow central region 1018 between outer regions 1020 lying generally within a plane to define a substantially flat configuration, and opposing pairs of tines 1038, generally similar to previous embodiments. Similar to other embodiments herein, the central region 1018 may include one or more struts or elements 1032, 1034 surrounding a central opening 1035. The struts 1032, 1034 may support the outer regions 1020 and/or tines 1038, similar to other embodiments herein.

Each of the outer regions 1020 defines a flange or lobe 1021 that may have a greater height (along the vertical or minor axis of the implant 1010) than the central region 1018 and surrounds an open interior space 1022, e.g., to provide greater contact area with adjacent tissue when implanted within an oropharyngeal region (not shown). Alternatively, as shown in FIGS. 22A-22D, each of the outer regions 1020' of the implant 1010' may include multiple lobes 1021', e.g., a pair of lobes 1021' defining a generally butterfly shape. As shown, the lobes 1021, 1021' include supplemental struts 1047, 1047' that extend across the open interior spaces 1022, 1022'. These struts 1047, 1047' may enhance the stiffness of the lobes 1021, 1021' while allowing them some independent motion relative to one another, and/or may enhance surface contact with adjacent tissue when the implant 1010, 1010' is implanted, similar to other embodiments herein.

As best seen in FIGS. 21C and 21D, the outer regions 1020, e.g., the lobes 1021 and/or struts 1047, may extend slightly out of the plane of the implant 1010, yet are still considered to define a substantially flat configuration as used herein. For example, horizontal struts 1044 and/or vertical struts 1048 defining the lobes 1021 and the supplemental struts 1047 may curve slightly out of the plane of the implant 1010, e.g., to enhance the rigidity of the implant 1010 while accommodating movement of the lobes 1021, for example, during normal movement of the oropharyngeal region within which the implant 1010 is implanted.

As shown in FIG. 21B, the implant 1010 may be formed from a substantially flat sheet, e.g., with the lobes 1020 and tines 1038 lying substantially within a plane. Similar to the implant 910, the tines 1038 extend vertically from the central region 1018, i.e., orthogonal to the length or major axis of the implant 1010. Unlike the implant 910, the tines 1038 may be plastically deformed and/or heat set to curve out of the plane of the implant 910 and away from another, as shown in FIGS. 21A and 21D, using similar methods to other embodiments herein. For example, the opposing pairs of tines 1038 may curve transversely out of the plane of the implant 1010, e.g., with the tips oriented substantially parallel to but offset from the plane of the implant 1010. Alternatively, the tines 1038 may be oriented horizontally relative to the outer regions (not shown), e.g., similar to other embodiments herein.

During use, the tines 1038 may be directed to a substantially straight and/or transverse configuration, e.g., extending substantially perpendicular to the plane of the implant 1010 to facilitate penetration into tissue. For example, the tines 1038 may be resiliently directed to the substantially straight and/or transverse configuration, without substantially displacing the rest of the implant 1010, e.g., the outer regions 1020, from the flat configuration, unlike previous embodiments. Alternatively, if desired, the outer regions 1020 may also be displaced, e.g., to direct the implant 1010 to a curved configuration, to facilitate introduction into a patient's mouth and oropharyngeal region, similar to other embodiments herein. In a further alternative, shown in FIG. 22E, an implant 1010" may be provided that includes outer regions 1020" on either side of a central region 1018" with each outer region 1020" including a single continuous loop enclosing and surrounding the interior space 1022". Each loop 1020" may have an oblong, elliptical, or other shape, e.g., having a greater height (along the vertical or minor axis "m" of the implant 1010") than width (along the horizontal or major axis "M" of the implant 1010" extending between the outer regions 1020").

Each loop 1020" may be coupled to the central region 1018" by one or more struts or elements 1032", e.g., a single strut 1032" extending between the midpoint of each loop 1020" and the central region 1018", which may enhance a flexibility of the outer regions 1020". Alternatively, multiple struts (not shown) may be provided between the outer regions 1020" and the central region 1018" similar to other embodiments herein, e.g., if greater rigidity is desired.

In addition, the implant 1010" generally includes opposing pairs of tines 1038" extending from the central region 1018", e.g., vertically or along the minor axis between the outer regions 1020". Unlike the implants 1010, 1010', the tines 1038" are substantially longer than the height of the central region 1018" and include barbed tips 1039", which may enhance engagement with or penetration into tissue and/or prevent the tines 1038" from being removed easily from tissue.

Figure 22E:
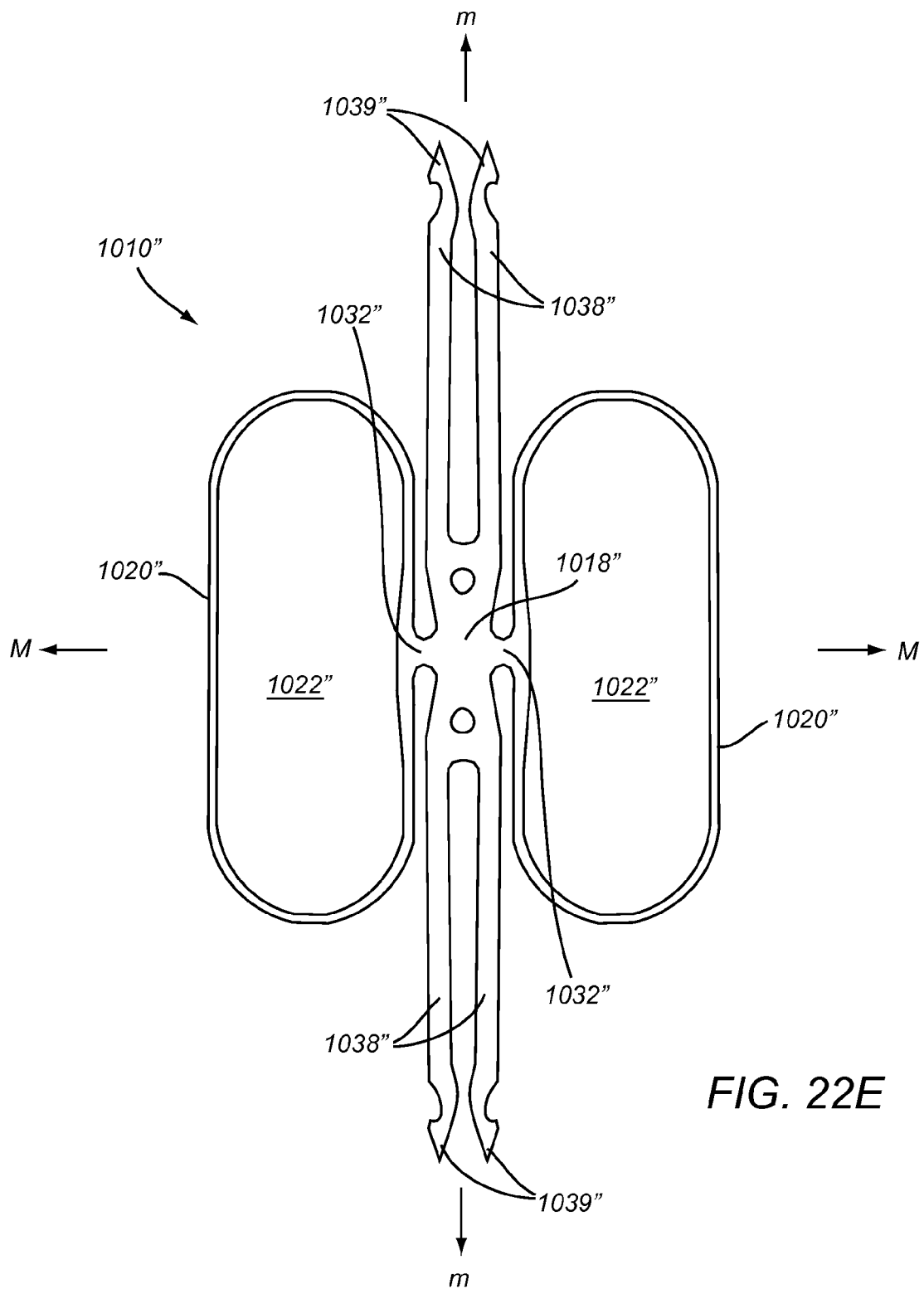
FIG. 22E is a front view of yet another embodiment of an implant including tines for securing the implant to tissue, similar to the implants shown in FIGS. 21A-22D.

The implant 1010" may be formed using materials and methods similar to those of other embodiments herein. For example, the implant 1010" may be biased to a substantially flat or planar configuration, e.g., as shown in FIG. 22E, with the tines 1038" extending out of the plane defined by the implant 1010" (not shown), or may be curved about the minor axis in a relaxed state, similar to other embodiments herein. The implant 1010" may be resiliently rolled, folded, or otherwise directed into a "C," rolled, or other curved configuration (not shown) for introduction and/or implantation within an oropharyngeal region (also not shown) of a patient, also similar to other embodiments herein.

Turning to FIGS. 23A-25B, an exemplary embodiment of a tool 1050 is shown that includes an elongate shaft 1051 for carrying the implant 1010 of FIGS. 21A-21D (or similarly, the implants 1010', 1010"), e.g., in the substantially flat configuration, and a delivery member 1070 for deploying the implant 1010 from the shaft 1051. Generally, the shaft 1051 includes a proximal end 1054 for manipulating the tool 1050 and a distal end 1054 for carrying an implant, such as implant 1010. The distal end 1054 of the tool 1050 may be sized for introduction into a patient's body, e.g., through the patient's mouth into the oropharyngeal region, and/or may include one or more features for releasably securing the implant 1010 to the tool 1050.

Figure 23A:
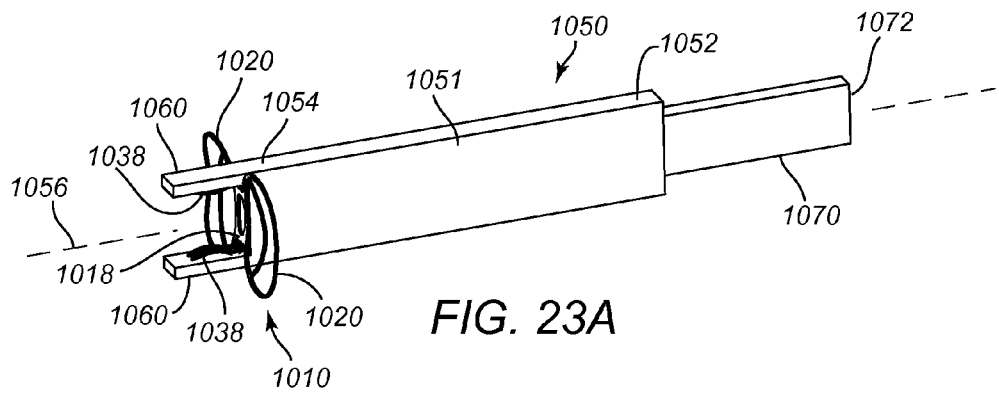
FIGS. 23A and 23B are perspective and side views of a tool in which the implant of FIGS. 21A-21D has been loaded such that the tines extend substantially perpendicular to the plane of the implant.
Figure 24A:
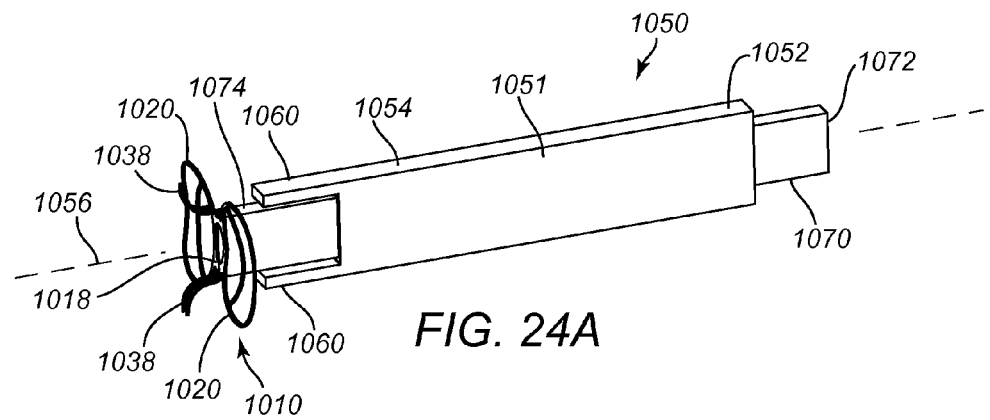
FIGS. 24A and 24B are perspective and side views of the tool of FIGS. 23A and 23B, showing a pusher member delivering the implant from the tool such that the tines are free to resiliently return to their transverse configuration.
Figure 25A:
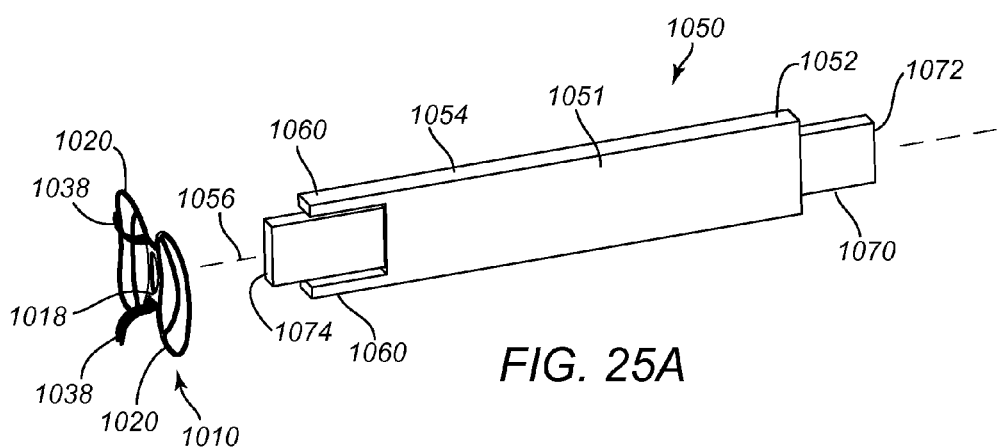
FIGS. 25A and 25B are perspective and side views of the tool of FIGS. 23A-24B, showing the implant released from the tool.
Figure 23B:
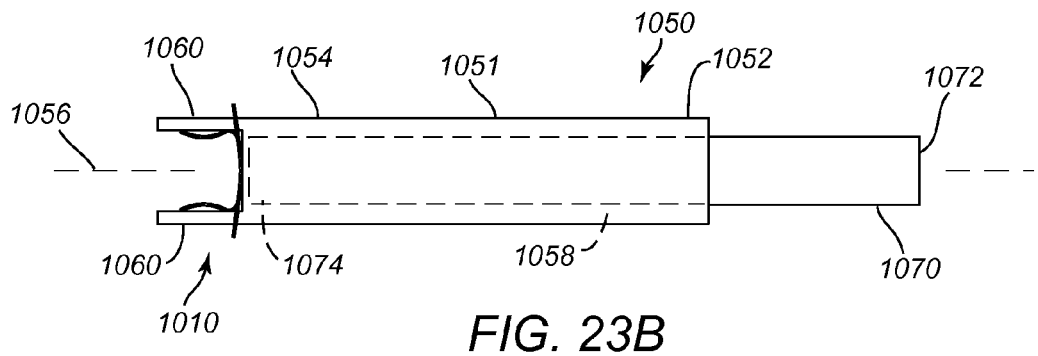
Figure 24B:
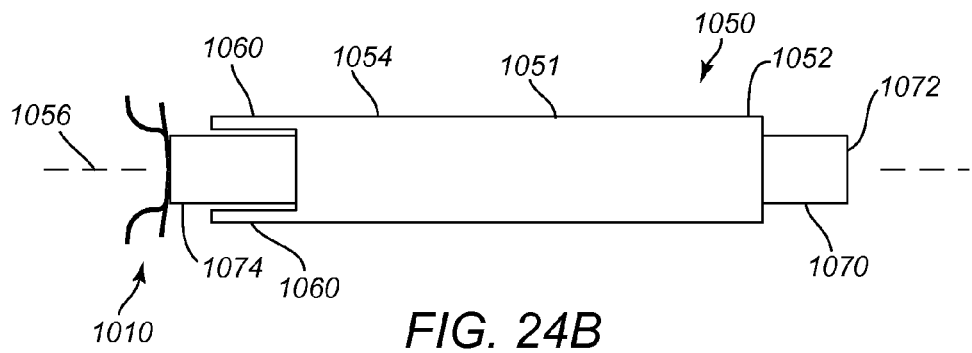
Figure 25B:
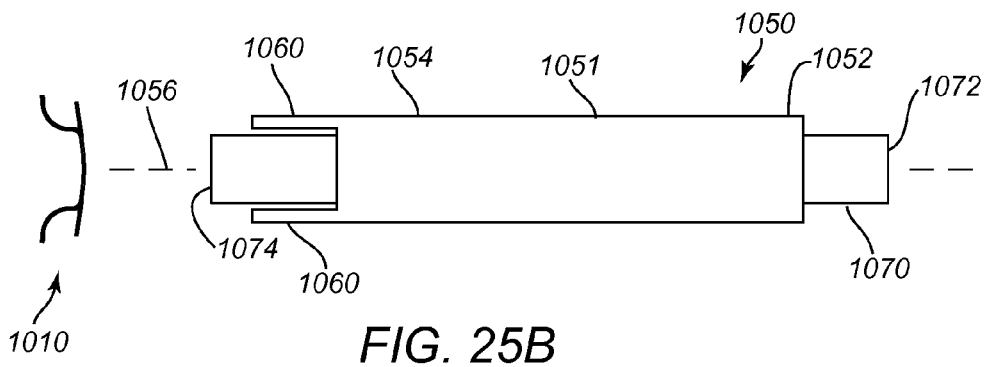

For example, as shown, the distal end 1054 may include a pair of substantially rigid fingers or rods 1060 spaced apart from one another by a predetermined distance, e.g., corresponding to the height of the central region 1018 of the implant 1010. Thus, the implant 1010 may be loaded onto the distal end 1054 of the tool 1010 by sliding the central region 1018 between the fingers 1060 with the outer regions 1020 on either side of the fingers 1060, as best seen in FIG. 23A. During this action, the tines 1038 (which are biased to extend outwardly away from one another, as described above and as shown in FIGS. 24A and 25A) may slidably engage inner surfaces of the fingers 1060, causing the tines 1038 to be elastically constrained in a substantially straight and/or distal orientation wherein the tips of the tines 1038 are closer than in their relaxed transverse orientation. Thus, the fingers 1060 may constrain the tines 1038 generally perpendicular to the plane of the implant 1010 and/or generally parallel to a longitudinal axis 1056 of the tool 1050 (although there may be some remaining curve in the tines 1038 when constrained in the substantially straight orientation, as best seen in FIG. 23B), which may facilitate delivery of the tines 1038 into tissue, as described further below.

The fingers 1060 may be sufficiently wide and/or otherwise shaped to slidably engage the outer regions 1020 of the implant 1010, e.g., to prevent lateral and/or rotational movement of the implant 1010 relative to the distal end 1054 of the tool 1050. Thus, the fingers 1060 may support the implant 1010 substantially stationary relative to the distal end 1054 during introduction. Alternatively, the tool 1050 may include one or more additional features to anchor or further secure the implant 1010 to the distal end 1054, e.g., one or more filaments, detents, and the like (not shown), which may engage one or more struts of the implant 1010. The features may remain engaged with the implant 1010 during introduction into a patient's mouth and oropharyngeal region, e.g., until immediately before the implant 1010 is to be released from the tool 1050, whereupon the features may be disengaged, e.g., using an actuator (not shown) on the proximal end 1052 of the tool 1050, to prepare the implant 1010 for delivery.

The delivery member 1070 may be a plunger or other elongate member slidable distally relative to the shaft 1051. For example, as best seen in FIG. 23B, the shaft 1051 may include a passage 1058 extending between the proximal and distal ends 1052, 1054 that may slidably receive the delivery member 1070. The delivery member 1070 generally includes a proximal end 1072 that extends proximally from the proximal end 1052 of the shaft 1051, and a distal end 1074 that may be disposed adjacent the fingers 1060. For example, in a first or proximal position, shown in FIGS. 23A and 23B, the distal end 1074 may be disposed proximal to the fingers 1060 so as not to interfere with loading the implant 1010 between the fingers 1060. The delivery member 1070 may then be advanced to a second or distal position, wherein the distal end 1074 passes between the fingers 1060, e.g., to advance and deploy the implant 1010 distally from the fingers 1060, as described further below.

Optionally, the tool 1050 may include one or more features for changing an orientation of the distal end 1054. For example, the distal end 1054 may include one or more hinges or other bendable features (not shown) that may be selectively directed to one or more angles relative to the longitudinal axis 1056 of the shaft 1051. An actuator (not shown) may be provided on the proximal end 1052 that is mechanically coupled to the bendable feature(s). Alternatively, the distal end 1054 may be malleable such that the user may deform the distal end 1054 to a desired orientation, which the distal end 1054 will maintain until otherwise deformed. In this alternative, the delivery member 1070 may be sufficiently malleable or flexible to accommodate such bending while still being able to slide axially relative to the shaft 1051.

During use, the implant 1010 may loaded onto the tool 1050, e.g., between the fingers 1060, as described above and shown in FIGS. 23A and 23B. The implant 1010 may be provided loaded on the tool 1050 by the manufacturer, or may be loaded onto the tool 1050 by a user, e.g., immediately before implantation into a patient, for example, to minimize the time that the tines 1038 are constrained in the distal orientation.

The implant 1010 carried on the distal end 1054 of the tool 1050 with the tines 1038 constrained by the fingers 1060 may be introduced through a patient's mouth into the oropharyngeal region. The fingers 1060 may be directed towards the posterior wall of the oropharyngeal region, e.g., pressed against the surrounding tissue, whereupon the delivery member 1070 may be advanced to deploy the implant 1010. As the delivery member 1070 is advanced, the tines 1038 may extend beyond the tips of the fingers 1060 and thereby necessarily penetrate into the adjacent tissues at locations immediately adjacent fingers 1060. As the tines 1038 are extended beyond the fingers 1060, the tines 1038 may resiliently expand away from one another, e.g., to open transversely as they penetrate into the adjacent tissues. Thus, the tines 1038 may attempt to return towards their relaxed, transverse orientation as they are directed into the tissue, until the implant 1010 is fully deployed beyond the fingers 1060. In this manner, the implant 1010 may be implanted directly against the wall of the oropharyngeal region with the tines 1038 extending outwardly away from one another to secure the implant 1010 relative to the tissue.

In an alternative embodiment, an implant may be provided that is generally similar to the implant 1010, except that the tines 1038 may be biased to extend inwardly towards one another (not shown). For example, the tines may be offset from one another such that the tines cross one another rather than away from one another, as shown in FIG. 21D. In this alternative, a tool similar to tool 1050 may be used to carry the implant with the tines constrained in a substantially straight and/or distal orientation. For example, the tool may include one or more features that extend through the central opening in the central region of the implant (not shown) that may slidably engage the tines and direct the tines from the relaxed, crossed orientation to the substantially straight and/or distal orientation. Thus, when the implant is deployed from the tool within the oropharyngeal region of a patient, the tines may be driven into tissue and allowed to resiliently cross and/or return towards their relaxed orientation, thereby securing the implant to tissue adjacent the oropharyngeal region.

In further alternatives, an implant may be provided that includes plastically deformable tines, e.g., initially provided in a substantially straight and/or distal orientation substantially perpendicular to the plane of the implant. For example, the implant may be carried by a tool that may include a hammer and anvil structure, similar to surgical staplers, disposed adjacent the tines. During use, as the tines are directed into tissue, the tool may be actuated to plastically deform the tines to direct them towards a transverse orientation, for example, towards one another, e.g., with or without crossing, or away from one another. The implant may be carried by the tool in its substantially flat configuration, or the outer regions may be displaced, e.g., to a curved configuration, to facilitate introduction into the oropharyngeal region or other implantation site.

Figure 26A:
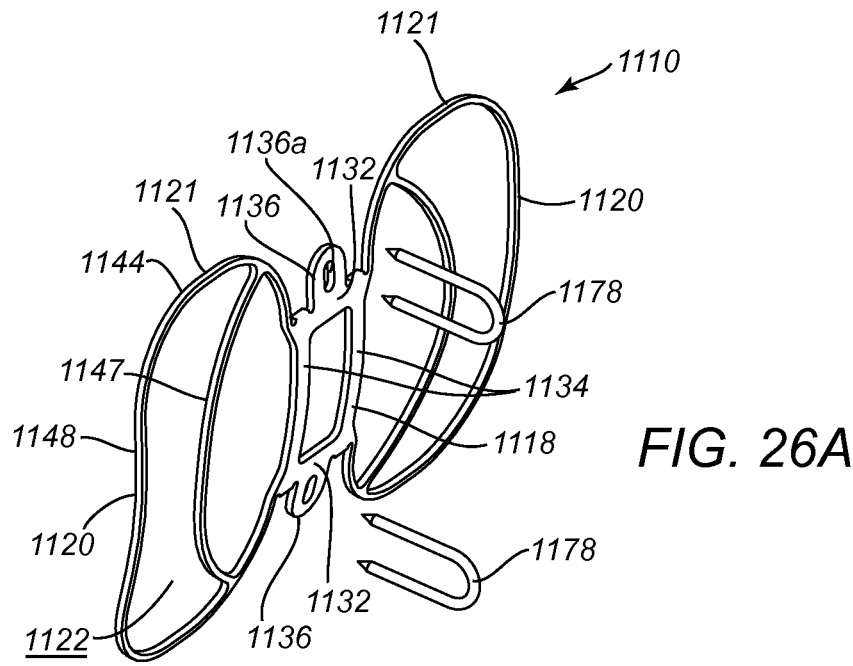
FIGS. 26A and 26B are perspective views of another embodiment of an implant for treating sleep apnea, snoring, and/or other breathing disorders that includes apertures for receiving separate fasteners for securing the implant to tissue.
Figure 26B:
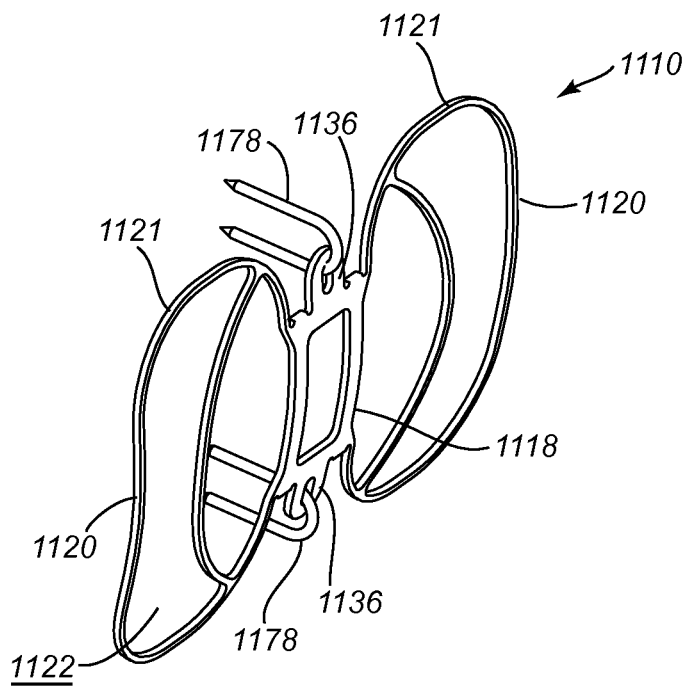

Turning to FIGS. 26A and 26B, another embodiment of an implant 1110 is shown that includes a central region 1118 between outer regions 1120 lying generally within a plane to define a substantially flat configuration. Similar to other embodiments, the central region 1118 may include one or more struts or elements 1132, 1134, e.g., surrounding a central opening 1135. Unlike some of the previous embodiments, the central region 1118 includes one or more rings 1136 formed on struts 1132 that define apertures 1136a, e.g., for receiving one or more fasteners 1178, as described further below.

Each of the outer regions 1120 defines a flange or lobe 1121 that has a greater height (along the vertical or minor axis of the implant 1110) than the central region 1118 and encloses or otherwise surrounds an open interior space 1122, e.g., to provide greater contact area with adjacent tissue when implanted within an oropharyngeal region (not shown). Alternatively, each of the outer regions 1120 of the implant 1110 may include multiple lobes, e.g., a pair of lobes defining a generally butterfly shape (not shown), similar to other embodiments herein. As shown, the lobes 1121 include supplemental struts 1147 that extend across the open interior spaces 1122, e.g., to enhance the stiffness of the lobes 1021, while allowing them some independent motion relative to one another, and/or to enhance surface contact with adjacent tissue when the implant 1110 is implanted, similar to other embodiments herein. The implant 1110 may be constructed generally using similar materials and methods to other embodiments herein.

During use, the implant 1110 may be introduced into an oropharyngeal region with the implant 1110 in its substantially flat relaxed configuration, or rolled or otherwise displaced into a curved configuration, similar to other embodiments herein. With the implant 1110 positioned at a desired location, e.g., against the tissue adjacent the posterior wall of the oropharyngeal region, one or more fasteners 1178 may be delivered to secure the implant 1110 to the tissue. For example, as shown, a fastener 1178 may be directed through each aperture 1136a into the tissue to secure the central region 1118 to the tissue. The fastener(s) 1178 may be a staple or clip having a "U" shape in its relaxed state or other shape, e.g., with crossed legs, legs oriented away from one another, and the like (not shown). For example, the fastener(s) 1178 may be formed from elastic or superelastic material, plastically deformable material, and the like. Alternatively, screws, sutures, or other fasteners (not shown) may be directed through the apertures 1136a into adjacent tissue to secure the implant 1110, e.g., as described elsewhere herein and in the references incorporated by reference herein. For example, the fasteners 1178 may have lengths sufficient to penetrate through the tissue of the posterior wall of the oropharyngeal region, e.g., into the anterior longitudinal ligament and/or into a vertebra to enhance anchoring the central portion 1118 of the implant 1110, while allowing the outer regions 1120 to deflect or otherwise move. Thus, the implant 1110 may support the lateral and/or anterior walls of the oropharyngeal region while allowing swallowing and/or other natural functions.

Figure 27A:
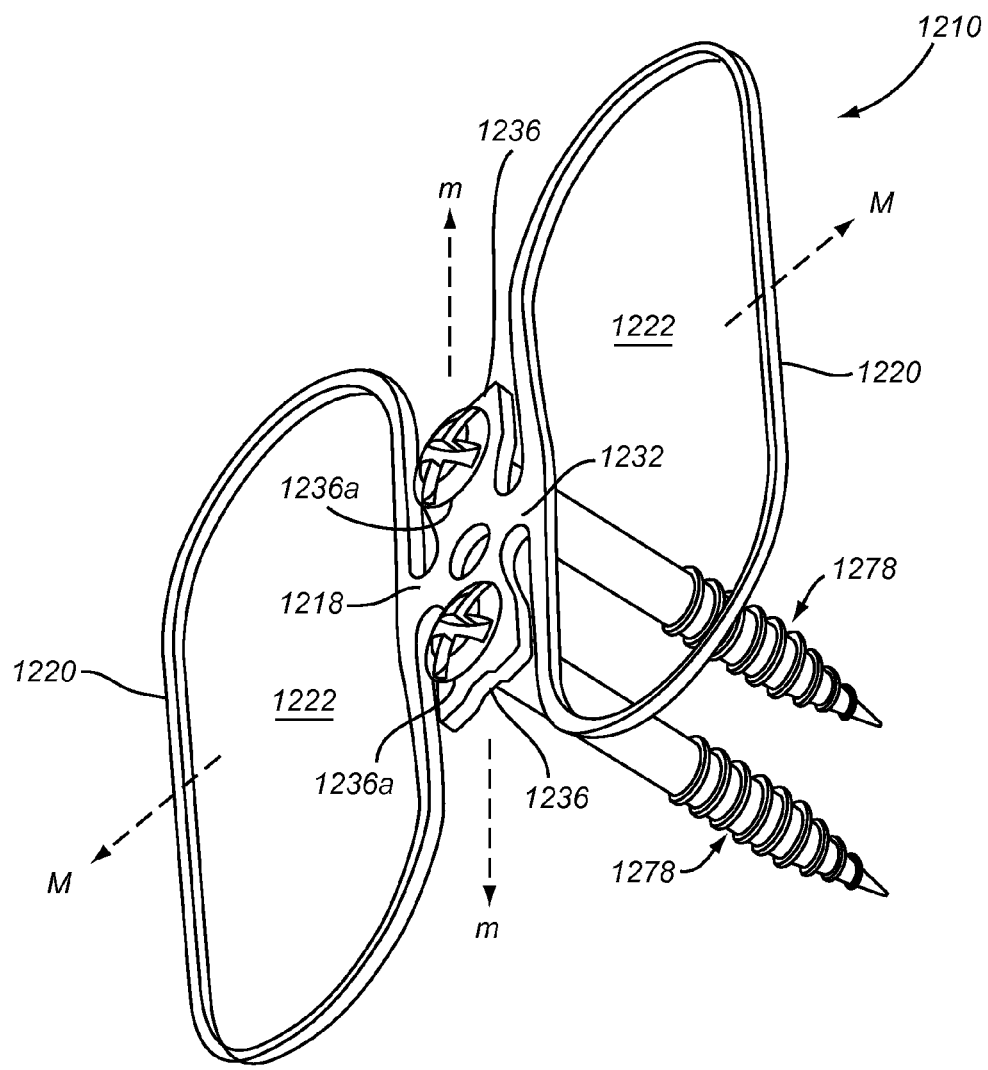
FIG. 27A is a front view of yet another embodiment of an implant for treating apnea, snoring, and/or other breathing disorders that includes apertures for receiving separate fasteners for securing the implant to tissue.

Turning to FIG. 27A, another embodiment of an implant 1210 is shown that is generally similar to the implant 1110 of FIGS. 26A and 26B, e.g., including a central region 1218 between outer regions 1220 lying generally within a plane to define a substantially flat configuration. Similar to other embodiments, each of the outer regions 1220 defines a flange or lobe that has a greater height (along the vertical or minor axis of the implant 1210) than the central region 1218 and surrounds an open interior space 1222, e.g., to provide greater contact area with adjacent tissue when implanted within an oropharyngeal region (not shown). Alternatively, the central region 1218 may include a plurality of struts or other elements (not shown) extending between the outer regions 1220, which may define a central region 1218 that has a height (along the vertical or minor axis) that is similar to or smaller than the outer regions 1220. Also, the central region 1218 may have a width (along the horizontal or major axis of the implant 1210) that is similar to or smaller than the width of each of the outer regions 1220. The overall dimensions of the implant 1210 may be such that the overall width of the implant 1210 (along the horizontal or major axis) is greater than the overall height of the implant 1210 (along the vertical or minor axis). Alternatively, the overall width and height may be similar to one another, e.g., such that the implant 1210 defines a generally square shape, or the overall width may be less than the height (not shown).

As shown in FIG. 27A, each outer region 1220 includes a substantially continuous loop enclosing the open interior space 1222, e.g. generally defining a "bow-tie" shape. Alternatively, each of the outer regions 1220 of the implant 1210 may include multiple lobes, e.g., a pair of lobes defining a generally butterfly shape (not shown), and/or may include one or more supplemental struts or other supports (also not shown) extending across the open interior region 1222, similar to other embodiments herein.

Unlike the implant 1110, the central region 1218 includes a single strut or element 1232 extending between the outer regions 1220, which may be similar to the embodiments of FIGS. 2-8. The strut 1232 may have a rigidity similar to the outer regions 1220 or may have a rigidity substantially greater than the outer regions 1220. For example, as described elsewhere herein, the outer regions 1220 may be folded, rolled, or otherwise directed to a curved configuration, e.g., for introduction into an oropharyngeal region. The strut 1232 may also curve when the outer regions are directed to the curved configuration, e.g., such that the implant 1110 defines a "C" or other substantially continuous arc or curve. Alternatively, the strut 1232 may be substantially rigid, e.g., such that the strut 1232 remains substantially flat or planar when the outer regions 1220 are directed to the curved configuration.

In addition, as shown in FIG. 27A, the central region 1218 may include one or more tabs or rings 1236 extending from the strut 1232 and including apertures 1236a, e.g., for receiving one or more fasteners 1278, as described elsewhere herein. For example, as shown, a tab 1236 extends from opposite sides of the strut 1232, e.g., generally along the vertical or minor axis "m" of the implant 1210. Thus, a pair of spaced apart apertures 1236a may be provided on the central region 1218 of the implant 1210, e.g., for receiving respective fasteners 1278, which may substantially enhance support of the implant 1210 within an oropharyngeal region. As shown, the apertures 1236a may be substantially enclosed openings, e.g., having diameters larger than shafts of the fasteners 1278 but smaller than the fastener heads.

Alternatively, the aperture may be an open-sided slot or other feature on the central region 1218 (not shown), which may receive a fastener therethrough. In another alternative, one or more other features, e.g., tabs and the like, may be provided on the central region 1218 over which a "U" shaped clip or other fastener (not shown) may be engaged to secure the central region 1218 to tissue. In a further alternative, a single aperture (not shown) may be provided in the central region 1218, e.g., for receiving a single fastener, or multiple pairs of apertures (also not shown) may be provided, e.g., on opposite sides of the strut 1232. For example, multiple pairs of apertures may be provided, each pair configured for receiving sutures, multiple tine clips, and the like (not shown).

During use, the implant 1210 may be introduced into an oropharyngeal region with the implant 1210 in its substantially flat relaxed configuration, or rolled or otherwise displaced into a curved configuration, similar to other embodiments herein. With the implant 1210 positioned at a desired location, e.g., with the central region 1218 against the tissue adjacent the posterior wall of the oropharyngeal region, one or more fasteners 1278 may be delivered to secure the implant 1210 to the tissue, e.g., to the anterior longitudinal ligament and/or underlying vertebra. For example, a screw or other fastener 1278 may be directed through each aperture 1236a into the tissue to secure the central region 1218 to the tissue.

The fasteners 1278 may be threaded or otherwise directed into tissue, e.g., into the anterior longitudinal ligament and/or into a vertebra adjacent the posterior wall (not shown). Delivering the fasteners 1278 along the minor axis "m" may align them vertically within the oropharyngeal region, e.g., along an axis defined by the anterior longitudinal ligament and/or the patient's vertebrae. This may provide substantial support for the implant 1210, e.g., to minimize lateral or rotational movement of the central region 1218 and consequently the entire implant 1210 relative to the oropharyngeal region. Alternatively, only a single fastener 1278 may be delivered, e.g., through one of the apertures 1236a or through a central aperture (not shown).

In a further alternative, one or more sutures (not shown) may be directed through the apertures 1236a and into underlying tissue to secure the implant 1210. The sutures may be bioabsorbable such that they are absorbed after sufficient time, e.g., after the implant has at least partially submucosalized. Alternatively, the sutures may not be bioabsorbable and may substantially permanently secure the implant 1210 within the oropharyngeal region.

Figure 27B:
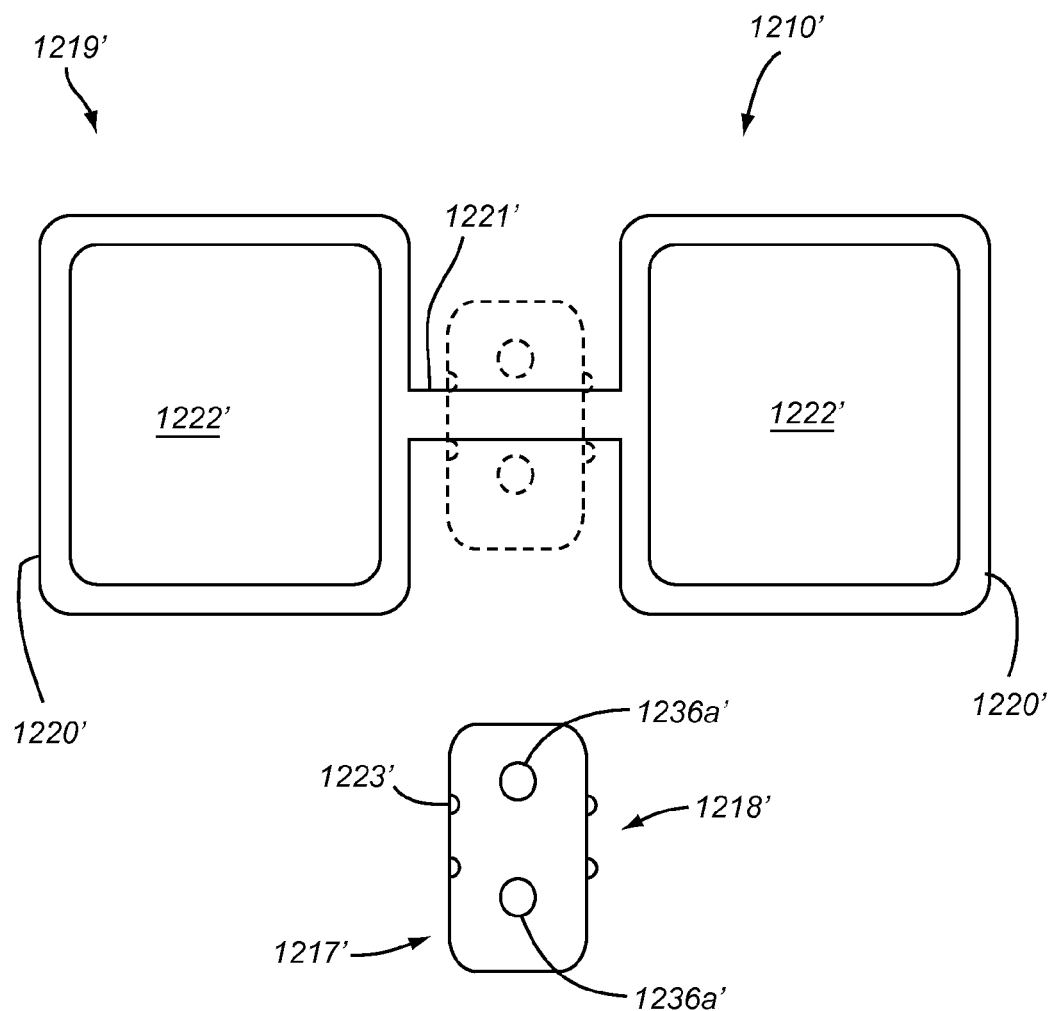
FIG. 27B is an alternative embodiment, similar to the implant of FIG. 27A, although including two components, e.g., a first component configured to be attached to tissue and a second component with lobes configured to be attached to the first component.

Turning to FIG. 27B, an alternative embodiment of an implant 1210' is shown that includes a central region 1218' between outer regions 1220' lying generally within a plane to define a substantially flat configuration. Unlike the previous embodiment, the implant 1210' includes two separate components, a first component 1217' including the central region 1218' and a second component 1219' including the outer regions 1220'. For example, the first component 1217' may include a panel of material including one or more apertures 1236a' therethrough, similar to the implant 1210 of FIG. 27A, while each of the outer regions 1220' may define a flange or lobe surrounding an open interior space 1222'.

Unlike the previous embodiment, the second component 1219' includes a strut 1221' extending between the outer regions 1220' and the first and second components 1217', 1219' include one or more connectors 1223' for coupling the first and second components 1217', 1219' together. In the exemplary embodiment shown, the first component 1217' includes a plurality of tabs or other connectors 1223' that may be sized to engage the strut 1221' of the second component 1219'. It will be appreciated that other connectors may be provided on the first and/or second components that allow the components to be introduced independently into an oropharyngeal region and then coupled together.

For example, in one method, the second component 1219' may be introduced into an oropharyngeal region and placed across the posterior wall, e.g., such that the strut 1221' extends across the anterior longitudinal ligament and/or the outer regions 1220' extend towards the lateral walls of the oropharyngeal region (not shown). The first component 1217' may then be introduced and then placed over the strut 1221', e.g., such that the connectors engage to secure the components together. One or more fasteners, e.g., screws, sutures, clips, and the like (not shown), may then be directed through respective apertures 1236a' in the central region 1218' to secure the implant 1210' to tissue adjacent the posterior wall.

Alternatively, the first component 1217' may be introduced before the second component 1219' and positioned against the posterior wall, e.g., such that the apertures 1236a' are aligned along the anterior longitudinal ligament. One or more fasteners may be directed through the apertures 1236a' into the adjacent tissue to secure the first component 1217' against the posterior wall. Then, the second component 1219' may be introduced, e.g., with the outer regions 1220' folded, or otherwise directed to a curved configuration, and may be docked or otherwise coupled to the first component 1217'. For example, the strut 1221' may be snapped into the tabs 1223' on the central region 1218' to secure the second component 1219' with the strut 1221' across the anterior longitudinal ligament, whereupon the outer regions 1220' may be released such that the outer regions 1220' extend along the lateral walls and/or otherwise dilate or support surrounding tissue.

Figure 14A:
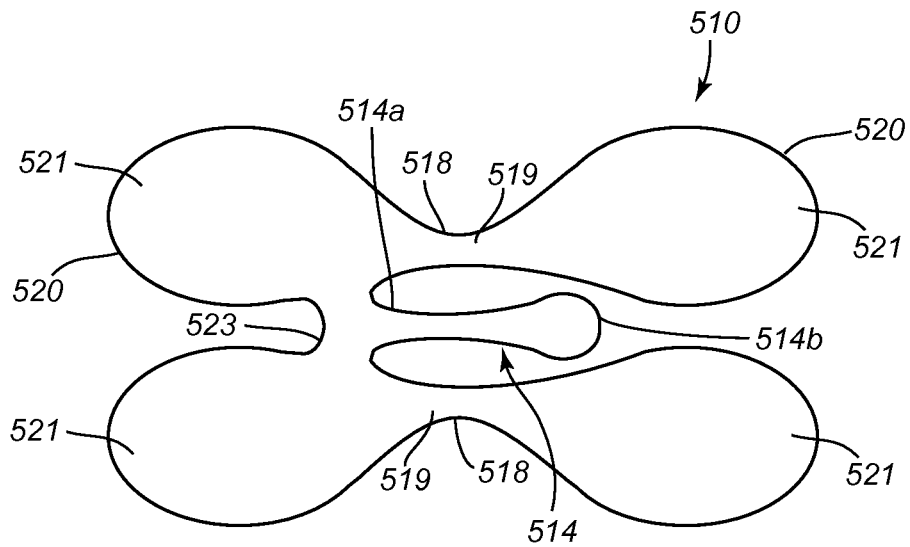
FIGS. 14A and 14B are top views of an exemplary embodiment of an implant including a strut that may be used to anchor the implant relative to the posterior wall of an oropharyngeal region, e.g., by implanting the struts through or behind the anterior longitudinal ligament or otherwise through tissue in the posterior wall.
Figure 14B:
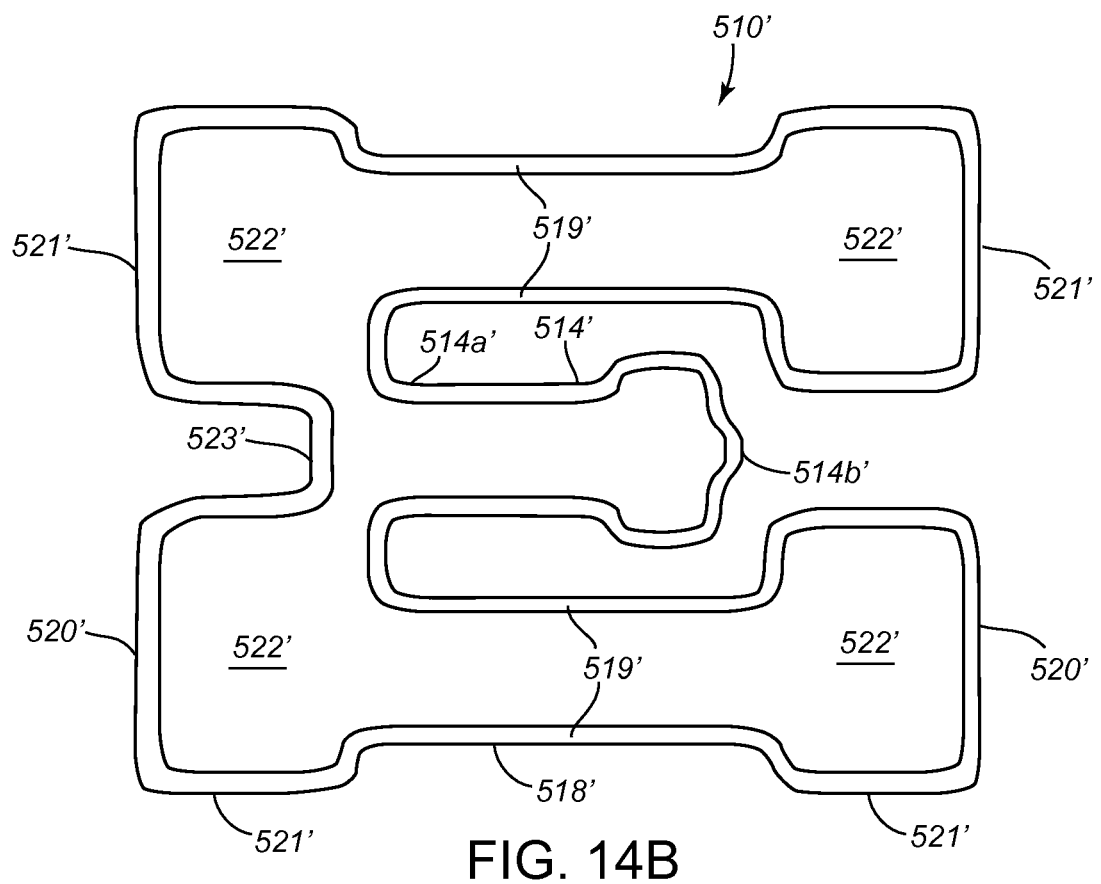

Turning to FIGS. 14A and 14B, additional embodiments of implants 510, 510' are shown that include a central region 518, 518' between outer regions 520, 520, generally similar to previous embodiments. As shown, the outer regions 520, 520' may have a greater height than the central region 518, 518', e.g., to define a generally "bow-tie" shape, also similar to previous embodiments. The central region 518, 518' may include a strut or other anchoring element 514, 514' extending at least partially between the outer regions 520, 520' that includes a fixed end 514*a*, 514*a*' coupled to one of the outer regions 520, 520', and a free end 514*b*, 514*b*' disposed adjacent the opposite outer region 520, 520'.

The implant 510, 510' may be formed from a substantially flat sheet, e.g., by laser-cutting, machining, etching, or otherwise forming the elements of the central region 518, 518' and outer regions 520, 520' from the sheet, similar to other embodiments. As shown in FIG. 14A, the outer regions 520 may include substantially continuous surface lobes 521 that are coupled together, e.g., by one or more links 519, 523. For example, as shown, one pair of lobes 521 defining first outer regions 520 may be coupled together by lateral link 523, and each of those lobes 521 may be coupled to a lobe 521 of the opposite second outer region 520 by longitudinal links 519 that extend through the central region 518. In this embodiment, the lobes 521 of the second outer region 520 may be separate from one another, e.g., to accommodate the free end 514*b* of the strut 514. Alternatively, as shown in FIG. 14B, the outer regions 520' may be defined by peripheral struts such that the lobes 521' include open interior regions 522'.

The implant 510, 510' may be biased to a substantially flat configuration defining a plane, yet may be resiliently directed to a curved configuration, e.g., for introduction and/or implantation, similar to other embodiments herein. The strut 514, 514' may also lie within the plane, yet may be resiliently directed out of the plane, e.g., to facilitate directing the strut 514, 514' through tissue, as described further below. Alternatively, the strut 514, 514' may be biased to extend out of the plane.

For example, the strut 514, 514' may be biased to curve out of the plane and back towards the plane, e.g., such that a midportion of the strut 514, 514' is disposed furthest away from the plane and the free end 514*b*, 514*b*' is disposed within or adjacent the plane. In a further alternative, the strut 514, 514' may be biased such that the fixed end 514*a*, 514*a*' curves or bends out of the plane, and the free end 514*b*, 514*b*' extends substantially parallel to the plane. In a further alternative, the implant 510, 510' may be biased to a "C" or other curved configuration, and the strut 514, 514' may be biased to extend out of the curved plane defined by the implant 510, 510', similar to the configurations described above.

During use, the implant 510, 510' may be directed into a curved configuration, e.g., by rolling, folding, or otherwise directing the outer regions 520, 520' out of plane towards one another, and then introduced into a target lumen. For example, the implant 510, 510' may be introduced through a patient's mouth into an oropharyngeal region (not shown), e.g., such that the central region 518, 518' is disposed adjacent the posterior wall of the oropharyngeal region.

One or more vertical incisions may be created in the posterior wall, e.g., through or behind the anterior longitudinal ligament ("ALL"), and the strut 514, 514' may be inserted through the incision(s), e.g., to substantially secure the implant 510, 510' relative to the posterior wall.

In an exemplary embodiment, an incision may be created that extends through or behind the ligament ALL and has a height similar to a width of the strut 514, 514'. Optionally, as shown in FIG. 14B, the free end 514*b*' of the strut 514' may have a width greater than the main portion of the strut 514', e.g., wider than the height of the incision. In this embodiment, the free end 514*b*' may be resiliently compressible, e.g., to reduce its width and accommodate insertion of the strut 514' through the incision. Once the free end 514*b*' is exposed on the other side of the incision, the free end 514*b*' may be allowed to resiliently expand back to its original width, e.g., to provide a support that resists the strut 514' being pulled back out through the incision.

Thus, the implant 514, 514' may be implanted within an oropharyngeal region with the central region 518, 518' disposed against the posterior wall and the outer regions 520, 520' providing an outward force, e.g., against the lateral walls of the oropharyngeal region, similar to other embodiments herein. With the strut 514, 514' extending through the incision, the implant 510, 510' may be substantially secured, thereby preventing migration or other undesired movement. If desired, the implant 510, 510' may be subsequently removed, e.g., by compressing the free end 514*b*, 514*b*' and withdrawing the strut 514, 514' from the incision, and then removing the implant 510, 510'.

Turning to FIGS. 15A-15D, alternative embodiments of implants 610 are shown that include one or more anchoring struts 614 that may substantially secure the implants 610 within a patient's body, e.g., within the oropharyngeal region with the strut(s) inserted into corresponding incision(s) through or behind the ligament ALL or other tissue on the posterior wall of the oropharyngeal region. The implants may be formed flat sheets, and/or by one or more wires or other elements, similar to other embodiments herein and in the applications incorporated by reference herein.

Figure 15A:
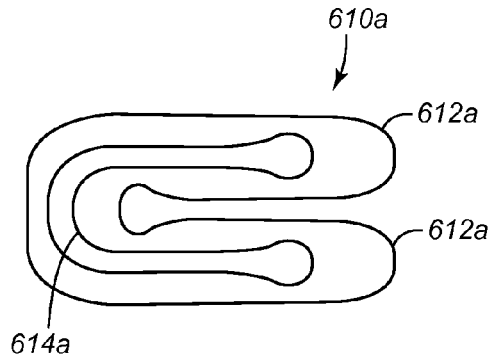
FIGS. 15A-15D show alternative embodiments of implants that include struts that may be used to anchor the implant relative to the posterior wall of an oropharyngeal region.

For example, FIG. 15A shows an implant 610*a* that includes multiple horizontal struts 612*a*, 614*a* oriented opposite one another. For example, upper and lower struts 612*a* may define an outer periphery of the implant 610*a* and include tips that are oriented opposite a tip of anchoring strut 614*a*. Thus, during implantation, the anchoring strut 614*a* may be inserted into/through an incision, e.g., in the posterior wall of an oropharyngeal region, and the upper and lower struts 612*a* may engage the outer surface of the posterior and lateral walls of the oropharyngeal region.

Figure 15B:
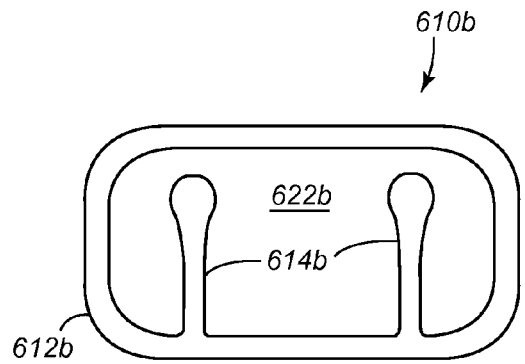

FIG. 15B shows another embodiment of an implant 610*b* that includes wire or other elements 612*b* defining an outer periphery of the implant 612*b*, e.g., surrounding an open interior space 622*b*, and anchoring struts 614*b* that extend vertically from the outer periphery at least partially across the interior space 622*b*. As shown, the struts 614*b* extend partially across the height of the implant 610*b*, i.e., which may be shorter than the length of the implant 610*b*. During use, the implant 610*b* may rolled, folded, or otherwise directed to a curved configuration, e.g., about its length, and introduced into an oropharyngeal region. The struts 614*b* may be inserted into vertical incisions, e.g., in the posterior or lateral walls of the oropharyngeal region, to reduce the risk of migration of the implant 610*b* once released. Optionally, as shown, the struts 614*b* may include enlarged free ends, which may enhance securing the implant, e.g., if the enlarged free ends are inserted through and out of the vertical incisions.

Figure 15C:
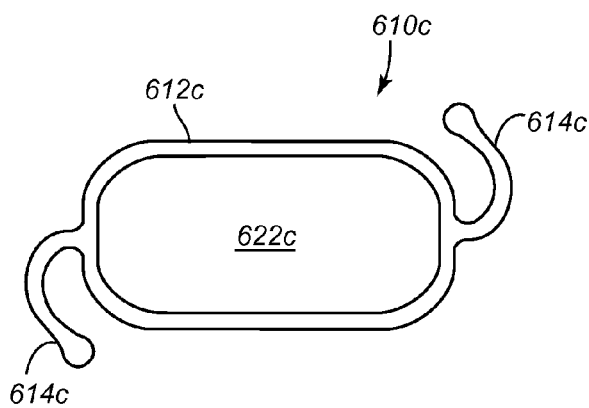

FIG. 15C shows another embodiment of an implant 610*c* that includes an outer periphery 612*c* surrounding an open interior space 622*c* and a pair of curved anchoring struts 614*c* offset from one another. In this embodiment, the struts 614*c* may be inserted into or through respective incisions (not shown), e.g., by rotating the implant 610*c* to direct free ends (which may include enlarged regions, if desired) of the struts 614*c* into or through the incisions.

Figure 15D:
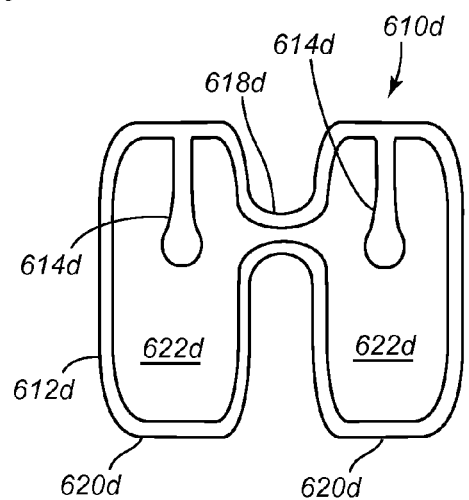

FIG. 15D shows still another embodiment of an implant 610*d* that includes an outer periphery 612*d* defining a central region 618*d* between outer regions 620*d*. The outer regions 620*d* substantially surround open interior spaces 622*d*, and anchoring struts 614*d* extend vertically at least partially across respective interior spaces. Thus, the struts 614*d* may be inserted into or through incisions, e.g., in the posterior wall of an oropharyngeal region to substantially secure the implant 610*d* therein.

In each of these alternatives, it will be appreciated that the implants 610 may be biased to substantially flat or curved configurations, and that the struts 614 may lie within the plane of the implants 610 or may extend out of the plane, similar to other embodiments herein. The struts 614 may be oriented vertically, e.g., for insertion into horizontal incisions in tissue, or may be oriented horizontally, e.g., for incision into vertical incisions in tissue, for example, into or behind the anterior longitudinal ligament adjacent the posterior wall of the oropharyngeal region.

Figure 16:
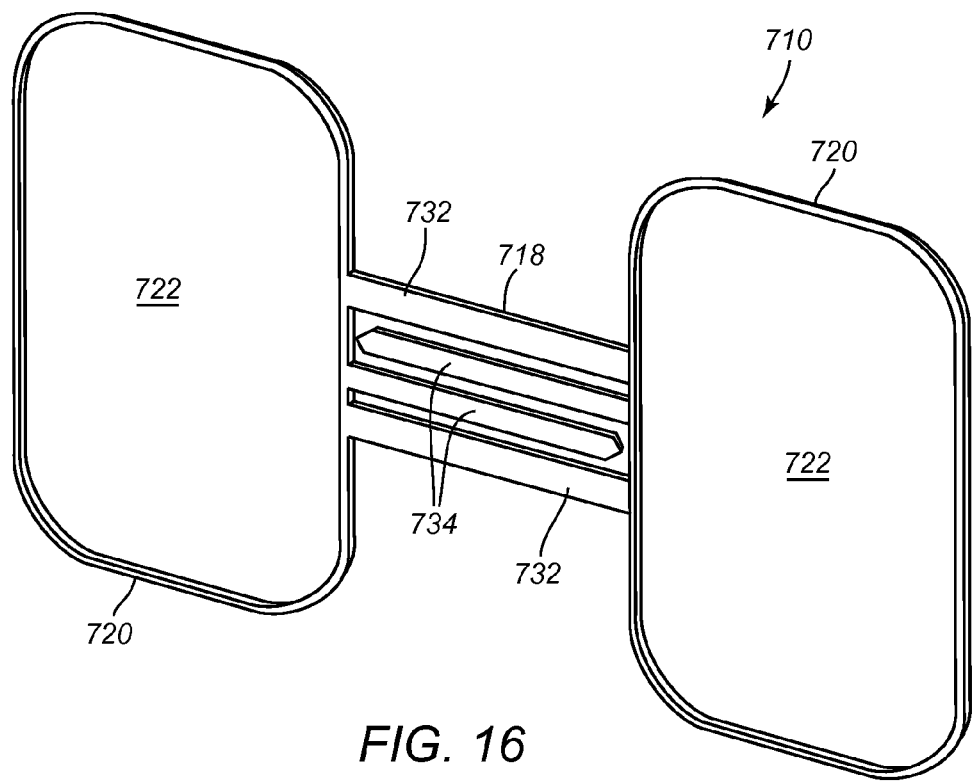
FIG. 16 is a top view of yet another embodiment of an implant that includes struts for anchoring the implant relative to tissue, e.g., to the posterior wall of an oropharyngeal region.

Turning to FIG. 16, still another embodiment of an implant 710 is shown that generally includes a central region 718 between lobes defining outer regions 720, similar to other embodiments herein. The central region 718 may include horizontal struts 732 that couple the outer regions 720 together, and one or more anchoring struts 734 that extend partially across the central region 718 between the outer regions 720. As shown, a pair of anchoring struts or tines 734 may be provided that extend inwardly from the opposite outer regions 720 such that the struts 734 are dispose adjacent one another. The tines 734 may be biased to lie within the plane of the implant 710 or may be biased out of the plane, similar to other embodiments herein.

In addition, as shown, the tines 734 include pointed or sharpened tips on their free ends, which may facilitate driving or otherwise inserting the tines 734 into tissue, e.g., with or without a preexisting incision. Alternatively, the tines 734 may include enlarged tips (not shown), similar to other embodiments herein, or other embodiments of anchoring struts herein may include pointed or sharpened tips instead of enlarged tips. Similar to other embodiments herein, the implant 710 may be introduced and implanted within an oropharyngeal region, e.g., such that the central region 718 extends across the posterior wall with the struts 734 inserted into tissue adjacent the posterior wall, and the outer regions 720 providing an outward force on the lateral walls of the oropharyngeal region.

Figure 17:
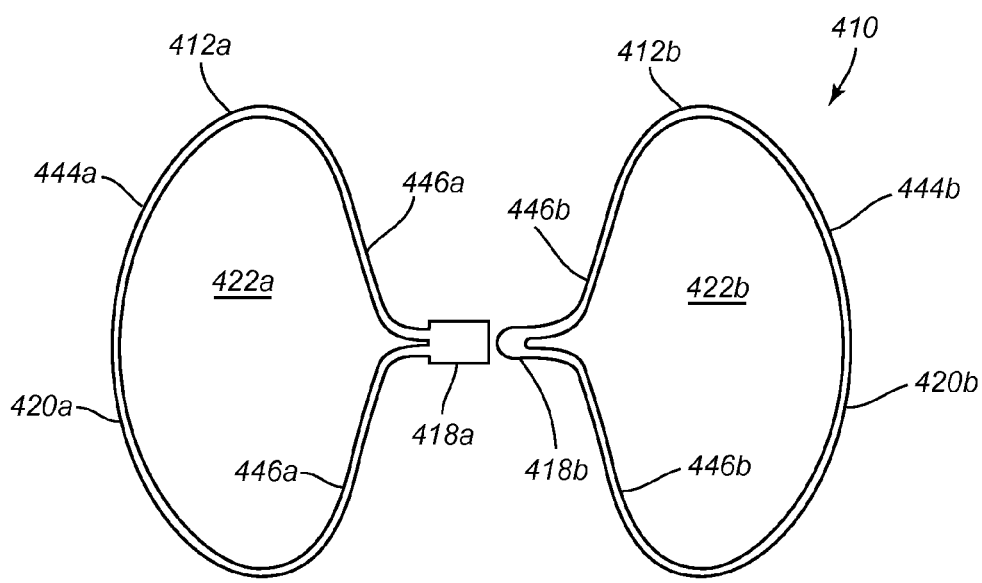
FIG. 17 is a front view of another embodiment of an implant for treating sleep apnea, snoring, and/or other breathing disorders that is formed from separate support components that may be coupled together.
Figure 18A:
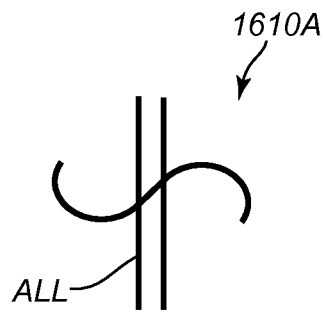
FIGS. 18A-18F show alternative embodiments of stents that may be passed at least partially through or behind the anterior longitudinal ligament or otherwise through tissue to secure the stents within an oropharyngeal region.
Figure 18B:
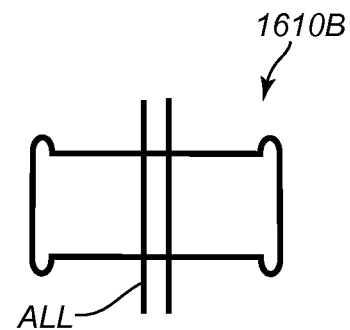
Figure 18C:
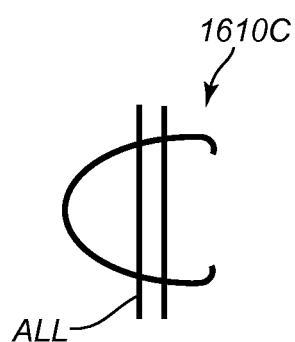
Figure 18D:
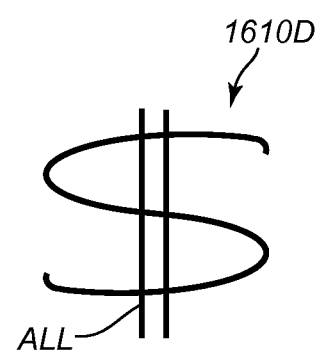
Figure 18E:
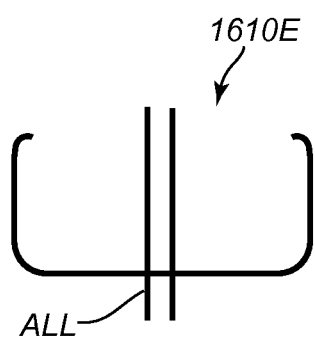
Figure 18F:
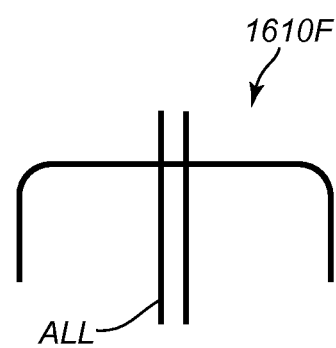

Turning to FIG. 17, another embodiment of an implant 410 is shown that is generally similar to the apparatus 110, described above, e.g., having a generally "bow-tie" shape, i.e., including a central region 418 between outer regions 420. In addition, from a top view, the implant 410 may have a planar or curved shape, similar to the other embodiments herein.

Unlike the previous embodiments, the implant 410 includes two separate support components 412 that may be provided separately and coupled together, e.g., in situ, to create the final implant 410. For example, each component 412 may include an outer region 420 including outer curved segments 444, e.g., defining a portion of a circle or ellipse, and segments 446 connecting ends of the curved segments 444 to the central region 418. The central regions 418*a*, 418*b* may include mating connectors, e.g., for coupling the components 412 together. For example, as shown, one central region 418*a* may include a female receptacle and the other central region 418*b* may include a male fitting that may be inserted into the receptacle. The connectors may be secured relative to one another, for example, by one or more of an interference fit, mating detents, magnets, and the like (not shown), e.g., within the receptacle and/or on the fitting or otherwise on the central regions 418.

During use, one of the components, e.g., component 412*a*, may be introduced into a target site, and the central region 418*a* of the component 412*a* may be inserted through or behind the ligament ALL (not shown, see, e.g., 4A and 4B) or other tissue structure, e.g., until the central region 418*a* is exposed on the other side. The other component 412*b* may then be introduced and the central region 418*b* engaged with the central region 418*a* to create the implant 410. One advantage of the multiple component implant 410 is that one of the outer regions does not need to be compressed to be inserted through or behind the ligament ALL, unlike the implant 110 shown in FIGS. 4A and 4B. Thus, the implant 410 may be formed from spring material, e.g., elgiloy or stainless steel, that may have greater rigidity than the implant 110.

Other configurations of stents or implants may be provided that may be secured relative to the ligament ALL or other tissue structure. For example, a helical stent may be threaded through or behind the ligament ALL, which may wrap circumferentially around the oropharyngeal region one or more times. FIGS. 18A-18F show additional alternative embodiments of implants 1610A-1610F that may be placed at least partially through or behind the ligament ALL, e.g., to secure and/or stabilize the implants.

In addition or alternatively, an implant or multiple component implant may be screwed into the ligament in a "key ring" fashion. Rotating the implant with the ligament at its center would allow the implant to screw in securely to the ligament. Some of the advantages of this type of insertion method are that no incisions may be required and the depth of penetration of the implant may be consistent for physicians and patients. In the multiple component implant configuration, a foundation or first implant component may be screwed into the ligament region and, once in place, a second implant component may be attached to the first implant component, e.g., by an interference fit, mating detents, magnets, and the like, as described above.

Figure 28A:
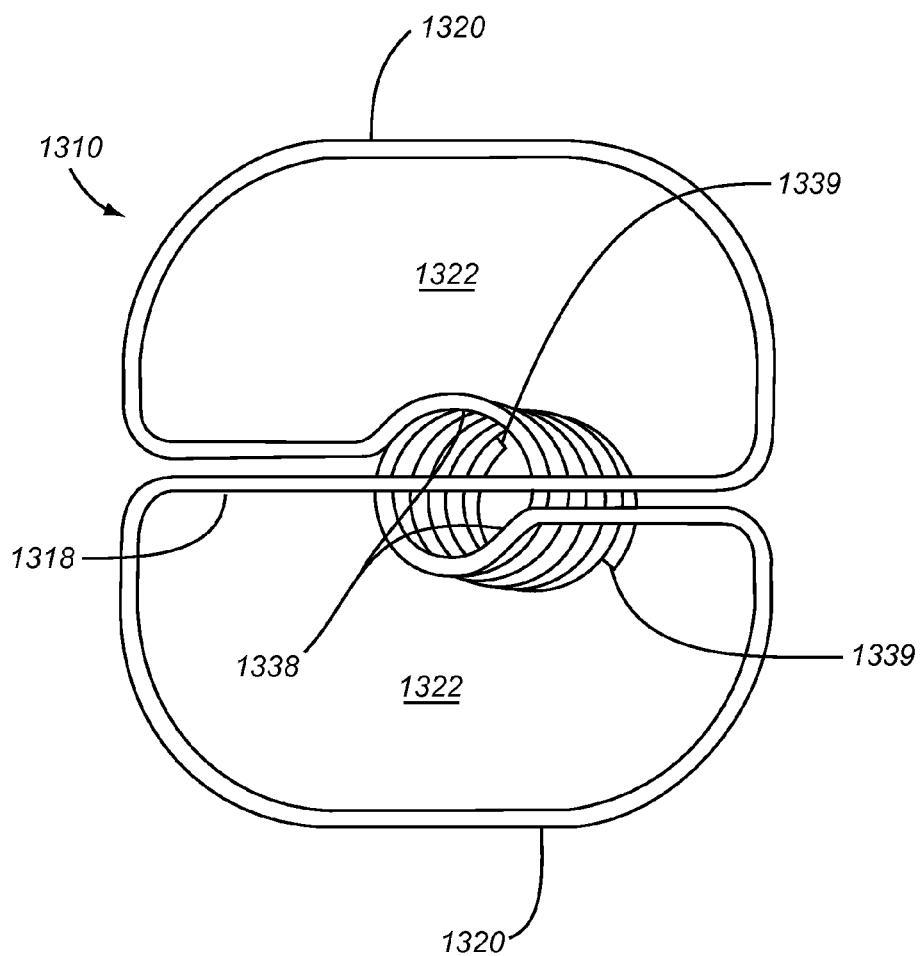
FIGS. 28A and 28B are perspective views of still another embodiment of an implant for treating apnea, snoring, and/or other breathing disorders that includes coiled tines extending from a planar support region for securing the implant to tissue.
Figure 28B:
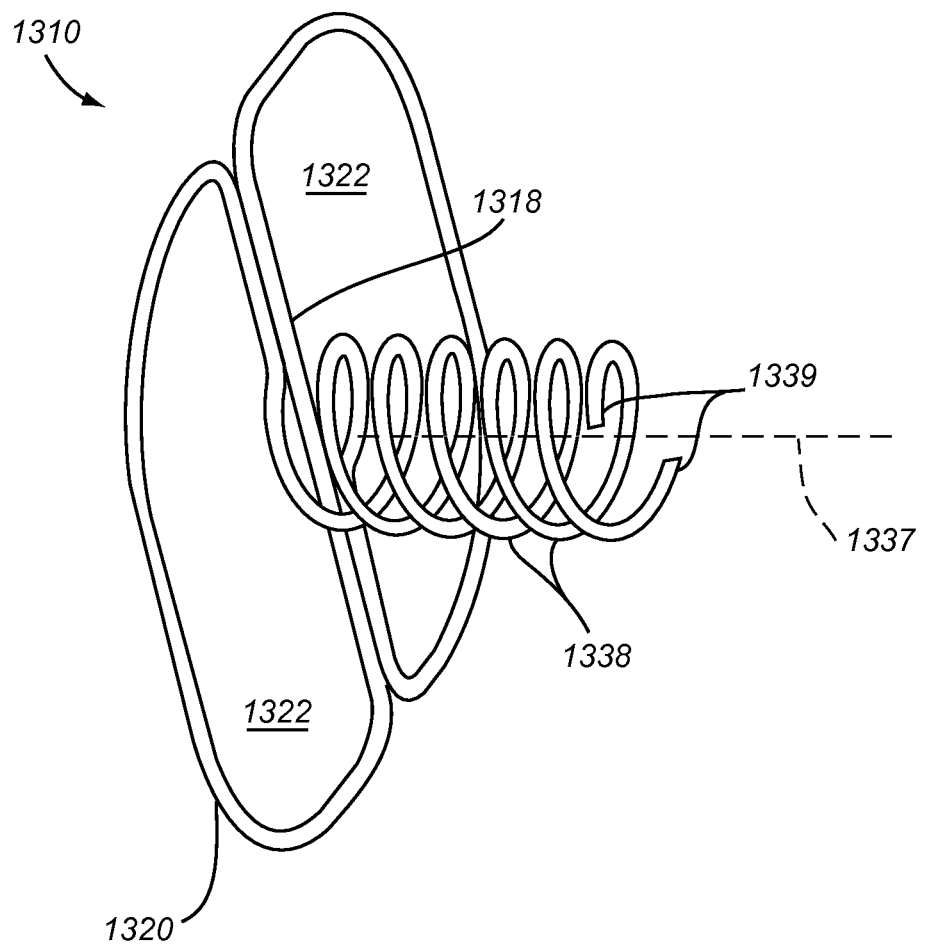

Turning to FIGS. 28A and 28B, still another embodiment of an implant 1310 is shown that includes a pair of lobes 1320 extending from a central region 1318 of the implant 1310 to define a substantially planar or flat configuration in a relaxed state. For example, similar to other embodiments herein, each lobe 1320 may include a wire or other structure disposed in a loop around an open interior space 1322, thereby substantially defining a flat configuration within a plane. As shown, a pair of lobes 1320 may be provided that extend away from one another and/or the central region 1318 within the plane. The lobes 1320 may be sufficiently flexible to be rolled, folded, or otherwise directed into a "C" shape or other curved configuration to facilitate introduction and/or implantation within an oropharyngeal region, similar to other embodiments herein. Alternatively, the lobes 1320 may define a curved configuration in the relaxed state, e.g., defining a curved "plane" or surface having a radius larger than the radius of curvature of an oropharyngeal region within which the implant 1310 may be introduced, similar to other embodiments herein.

One or more tines or coils 1338 may extend from the central region 1318, e.g., out of the plane of the lobes 1320. In the embodiment shown in FIGS. 28A and 28B, a pair of coiled tines 1338 may be provided that extend helically around an insertion axis 1337, e.g., extending substantially perpendicular or otherwise transverse to the plane defined by the lobes 1320. The tines 1338 may be in phase with one another, e.g., both extending clockwise away from the central region 1318 as shown in FIG. 28A (or alternatively counter clockwise, not shown). The turns of the tines 1338 may alternate along a length of the coil such that the tines 1338 are nested together. Each tine 1338 may terminate in a sharpened, pointed, or other tip 1339, e.g., including barbs or other features (not shown), which may be disposed opposite one another or otherwise configured to facilitate threading or otherwise delivering the tines 1338 into tissue. Alternatively, as shown in FIGS. 29A and 29B, a single tine or coil 1338', 1338" may be provided rather than the pair of tines 1338 shown in FIGS. 28A and 28B.

In an exemplary embodiment, the implant 1310 may be formed from a single continuous length of wire, e.g., wound, bent, or otherwise formed into the desired shape for the implant 1310. For example, a central section of the wire may define the central region 1318 of the implant 1310, and opposite sections of the wire may define opposite lobes 1320 and tines 1338. For example, a length of wire may be wound or bent to define the outer periphery of each lobe 1320 and then inwardly adjacent the central section of the wire, and then wound helically to define each tine 1338.

Figure 29A:
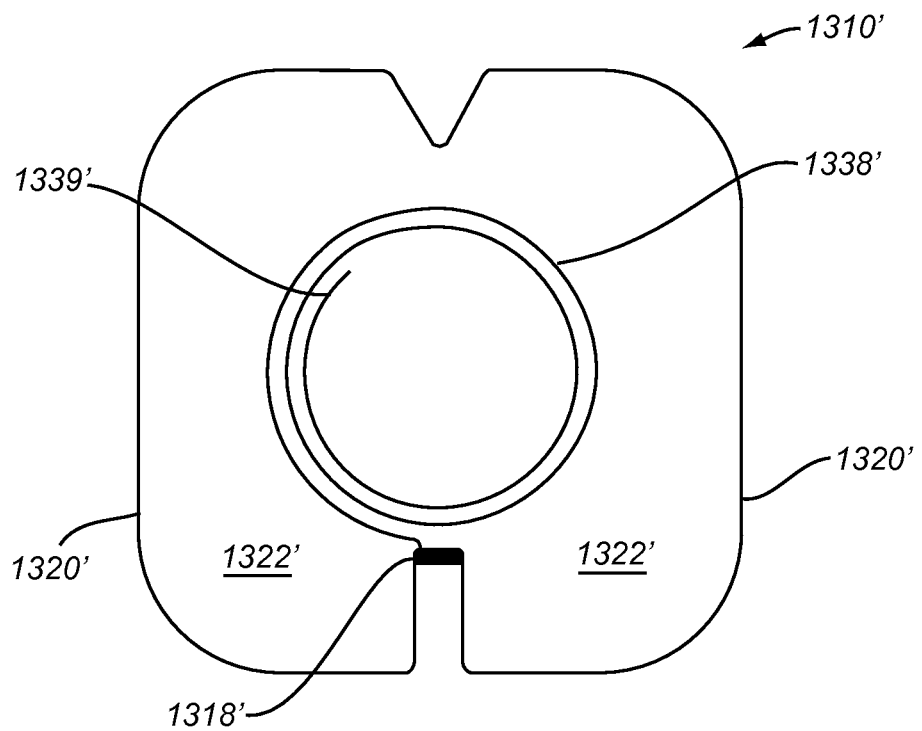
FIGS. 29A and 29B are front views of alternative embodiments of the implant of FIGS. 28A and 28B including a single coiled tine extending from a planar support region of the implant.
Figure 29B:
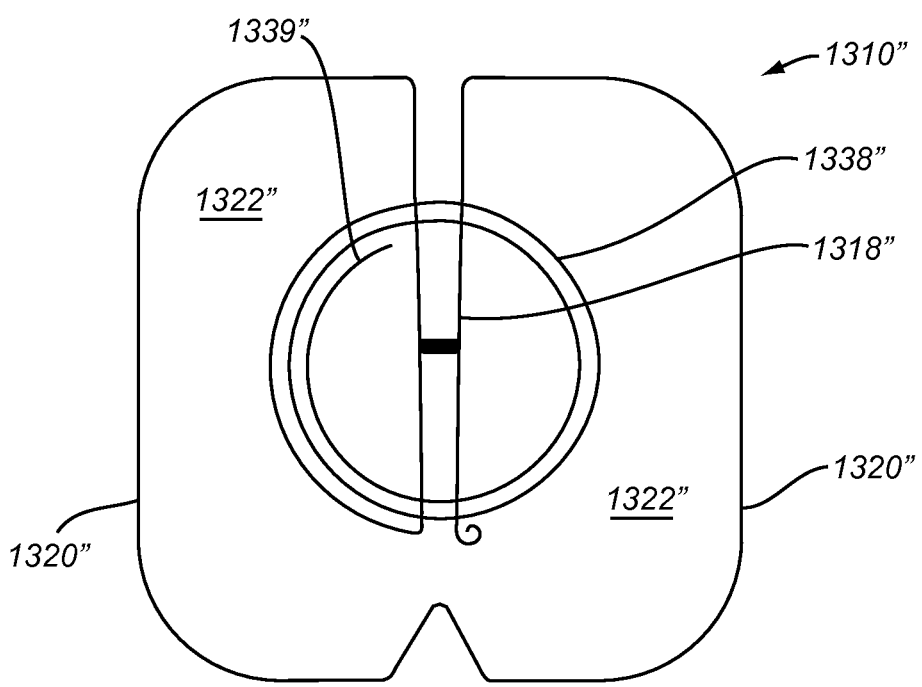

In the alternative embodiments shown in FIGS. 29A and 29B, the implant 1310', 1310" may be formed from a single length of wire with a first section wound to define both lobes 1320', 1320" of the implant 1310', 1310" and a second section would to define the helical tine or coil 1338', 1338". The end of the first section may be secured to the second section, e.g., by welding, fusing, sonic welding, bonding with adhesive, and the like, for example, adjacent the central region 1318', 1318".

Alternatively, the implant 1310 (and similarly the implants 1310', 1310") may be formed from multiple sections of wire attached together, e.g., by butt or lap welding, fusing, and the like. In a further alternative, the implant 1310 may be formed from a sheet or other body of material, e.g., by laser, mechanically or otherwise cutting the desired elements from the sheet and then bending, winding, or forming the elements into the desired configuration.

Figure 29C:
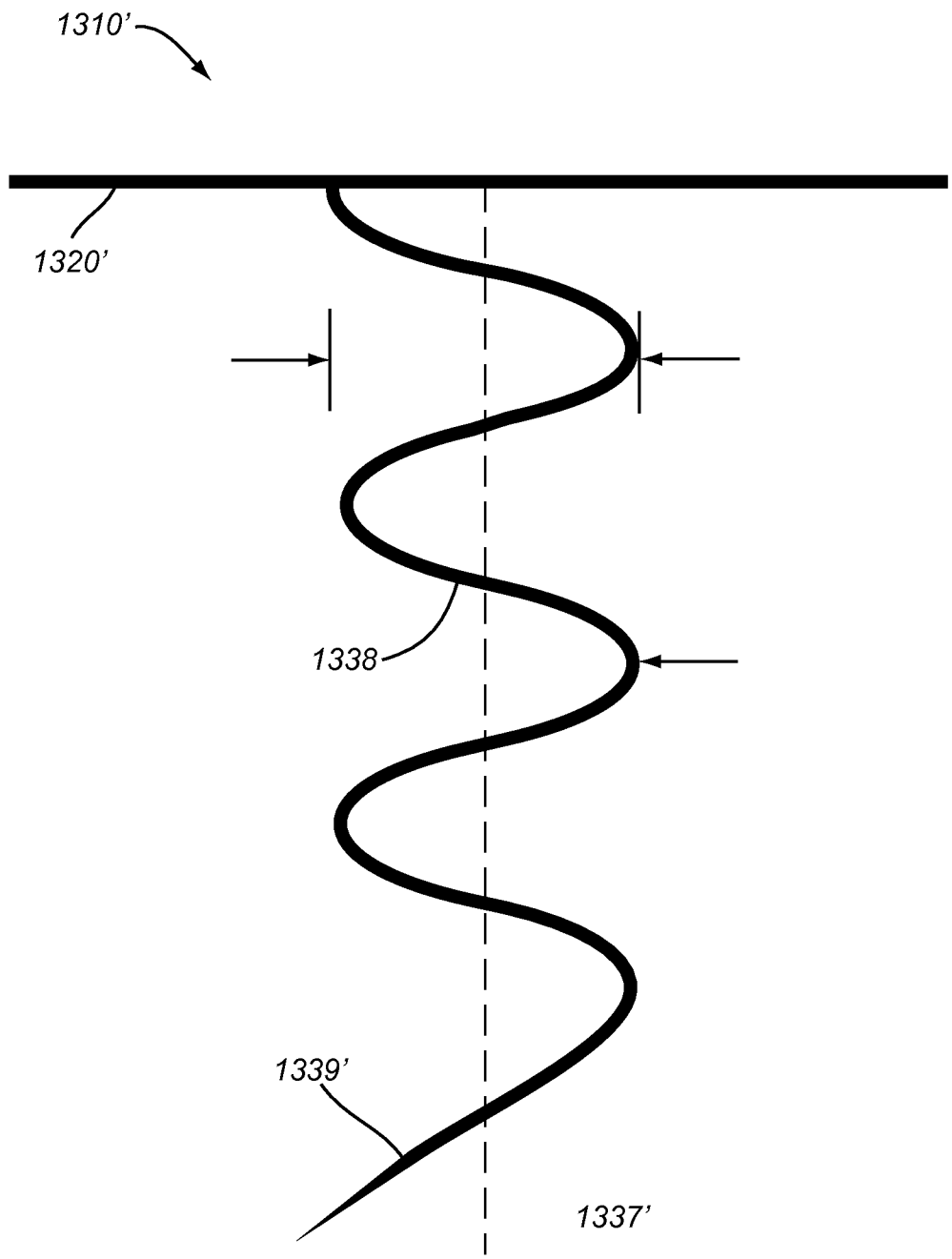
FIG. 29C is a side view of the implants of FIGS. 29A and 29B.

The material of the implant 1310 may be heat treated and/or otherwise processed to provide the desired mechanical characteristics for the implant 1310. For example, the material of the lobes 1322 may be heat treated to be biased to the planar configuration, yet capable of being elastically or resiliently deflected to the curved configuration. The tines 1338 may be biased to the helical configuration, e.g., as shown in FIG. 29C, and sufficiently rigid to substantially retain their shape and allow the tines 1338 to be directed into and through tissue.

During use, the lobes 1320 may be directed to a curved configuration, e.g., curved away from the tines 1338 such that the tines 1338 may be oriented towards the posterior wall of an oropharyngeal region into which the implant 1310 is introduced. The tips 1339 may be directed into the tissue adjacent the posterior wall, and then the implant 1310 may be rotated to thread the tines 1338 into the tissue, e.g., into the anterior longitudinal ligament and/or a vertebra adjacent the oropharyngeal region. Before the lobes 1320 are released, the implant 1310 may be oriented in a desired orientation, e.g., such that the lobes 1320 are aligned around the lateral and/or anterior walls of the oropharyngeal region. The lobes 1320 may then be released, whereupon the implant 1310 may support the walls of the oropharyngeal region, similar to other embodiments herein.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A method for treating an oropharyngeal region of a patient comprising:
   directing an implant comprising first and second outer regions separated by a central region into the oropharyngeal region in a curved configuration;
   positioning the central region adjacent a posterior wall of the oropharyngeal region;
   directing one or more fasteners through the central region into tissue adjacent the posterior wall into the anterior longitudinal ligament of the patient; and
   releasing the implant within the oropharyngeal region such that the outer regions apply a force to dilate tissue adjacent the oropharyngeal region.

2. The method of claim 1, wherein directing one or more fasteners comprises directing first and second fasteners through the central region into tissue adjacent the posterior wall.

3. The method of claim 2, wherein the fasteners are aligned along an axis extending substantially parallel to the anterior longitudinal ligament of the patient.

4. The method of claim 1, wherein the first outer region comprises a first loop, the second outer region comprises a second loop and the central region comprises one or more struts extending between the first and second loops.

5. The method of claim 4, wherein the central region comprises a pair of tabs on the one or more struts, and wherein directing one or more fasteners through the central region comprises directing a fastener through an aperture in each of the tabs into tissue adjacent the posterior wall.

6. The method of claim 1, wherein the central region is positioned adjacent the posterior wall such that the outer regions are oriented towards opposite lateral walls of the oropharyngeal region, and wherein, when the implant is released, the outer regions contact the opposite lateral walls to apply the force to dilate tissue adjacent the oropharyngeal region.

7. The method of claim 1, wherein the one or more fasteners comprise one or more screws, clips, staples, or sutures.

8. The method of claim 1, wherein the one or more fasteners are directed into a vertebra of the patient.

9. A system for implantation within an oropharyngeal region, comprising:
   an implant comprising a central region between first and second outer regions generally defining a plane in a substantially flat configuration, the outer regions defining lobes surrounding respective open interior spaces on either side of the central region, the outer regions displaceable out of the plane such that the implant defines a curved configuration, the central region comprising one or more apertures; and
   one or more screws, each receivable through one of the one or more apertures in the central region for securing the central region to tissue adjacent the oropharyngeal region, wherein the central region comprises a strut extending between the first and second outer regions, and a pair of tabs extending from the strut, each tab comprising an aperture therethrough for receiving a respective screw therethrough.

10. The system of claim 9, wherein the one or more apertures extend through the central region substantially perpendicular to the plane and are sized for receiving a shaft of the one or more screws.

11. The system of claim 10, wherein the one or more apertures comprise an enclosed opening or a slot.

12. The system of claim 9, wherein each of the first and second outer regions comprises a loop enclosing the interior open space.

13. An implant for implantation within an oropharyngeal region adjacent a ligament, comprising:
   a first loop surrounding and enclosing a first interior open space;
   a second loop surrounding and enclosing a second interior open space;
   a first strut extending between the first and second loops thereby defining a major axis between the first and second loops; and
   a pair of tabs extending from the strut and comprising apertures therethrough aligned along a minor axis orthogonal to the major axis, the apertures sized to receive respective fasteners therethrough,
   wherein the first and second loops are deflectable to a curved configuration to apply a force to dilate tissue adjacent the oropharyngeal region when the implant is disposed within the oropharyngeal region and fasteners are directed through the apertures to secure the strut within the oropharyngeal region.

14. The implant of claim 13, further comprising a pair of screws sized for introduction through the apertures.

15. The implant of claim 13, wherein the first strut is the only strut extending between the first and second loops.

* * * * *